United States Patent
Bishop et al.

(10) Patent No.: US 11,447,533 B2
(45) Date of Patent: Sep. 20, 2022

(54) ANTIMICROBIAL AND ANTICANCER PEPTIDES AND CONJUGATES AND COMPOSITIONS, METHODS, ARTICLES AND KITS RELATING THERETO

(71) Applicant: George Mason Research Foundation, Inc., Fairfax, VA (US)

(72) Inventors: Barney Bishop, Annandale, VA (US); Saswata K. Sahoo, Silver Spring, MD (US); Justin Davis, Suffolk, VA (US)

(73) Assignee: GEORGE MASON RESEARCH FOUNDATION, INC., Fairfax, VA (US)

( * ) Notice: Subject to any disclaimer, the term of this patent is extended or adjusted under 35 U.S.C. 154(b) by 116 days.

(21) Appl. No.: 16/710,921

(22) Filed: Dec. 11, 2019

(65) Prior Publication Data

US 2020/0190156 A1    Jun. 18, 2020

Related U.S. Application Data

(60) Provisional application No. 62/778,964, filed on Dec. 13, 2018.

(51) Int. Cl.

| C07K 14/01 | (2006.01) |
|---|---|
| C07K 14/47 | (2006.01) |
| C07K 14/00 | (2006.01) |
| A61K 47/65 | (2017.01) |
| C12Q 1/04 | (2006.01) |
| A61K 38/00 | (2006.01) |

(52) U.S. Cl.
CPC .......... *C07K 14/4723* (2013.01); *A61K 47/65* (2017.08); *C07K 14/001* (2013.01); *C12Q 1/04* (2013.01); *A61K 38/00* (2013.01)

(58) Field of Classification Search
None
See application file for complete search history.

(56) References Cited

U.S. PATENT DOCUMENTS

| 8,404,636 B2 | 3/2013 | Bishop et al. | |
| 10,174,081 B2 * | 1/2019 | Bishop | ............ C12Q 1/18 |
| 2014/0128313 A1 | 5/2014 | Bishop et al. | |
| 2015/0050351 A1 * | 2/2015 | Gonzalez | ............ C07K 7/06 424/491 |

FOREIGN PATENT DOCUMENTS

WO    WO2016044683    *    3/2016

OTHER PUBLICATIONS

Blast search results for SEQ ID No. 11 (retrieved from https://blast.ncbi.nlm.nih.gov/Blast.cgi on Jan. 5, 2021, 14 pages) (Year: 2021).*
Blast search results for SEQ ID No. 13 (retrieved from https://blast.ncbi.nlm.nih.gov/Blast.cgi on Jun. 30, 2021, 16 pages) (Year: 2021).*
De Latour et al., "Antimicrobial activity of the Naja atra cathelicidin and related small peptides", Biochemical and Biophysical Research Communications, 2010, vol. 396, pp. 825-830.
Lung et al., "Discovery of potent antimicrobial peptide analogs of txosin-B", Bioorganic & Medicinal Chemistry Letters, 2012, vol. 22, pp. 4185-4188.
Pérez-Peinado et al., "Mechanisms of bacterial membrane permeabilization by crotalicidin (Ctn) and its fragment Ctn[15-34], antimicrobial peptides from rattlesnake venom", The American Society for Biochemistry and Molecular Biology, Inc., 2017, pp. 1-28.

* cited by examiner

*Primary Examiner* — Ronald T Niebauer
(74) *Attorney, Agent, or Firm* — Saul Ewing Arnstein & Lehr LLP; Alireza Behrooz

(57) ABSTRACT

Peptides and conjugates are described herein, including peptides having antimicrobial and/or anticancer properties, as are compositions, articles, and kits comprising such peptides and conjugates, and methods for using the peptides and conjugates.

6 Claims, 14 Drawing Sheets

Specification includes a Sequence Listing.

SEQUENCE LISTING

<160> NUMBER OF SEQ ID NOS: 53

<210> SEQ ID NO 1
<211> LENGTH: 11
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE

```
<222> LOCATION: (1)..(1)
<223> OTHER INFORMATION: Lys or Arg
<220> FEATURE:
<221> NAME/KEY: MISC_FEATURE
<222> LOCATION: (2)..(2)
<223> OTHER INFORMATION: Lys or Arg
<220> FEATURE:
<221> NAME/KEY: MISC_FEATURE
<222> LOCATION: (3)..(3)
<223> OTHER INFORMATION: Phe, Ala, or Trp
<220> FEATURE:
<221> NAME/KEY: MISC_FEATURE
<222> LOCATION: (4)..(4)
<223> OTHER INFORMATION: Lys or Arg
<220> FEATURE:
<221> NAME/KEY: MISC_FEATURE
<222> LOCATION: (5)..(5)
<223> OTHER INFORMATION: Lys or Arg
<220> FEATURE:
<221> NAME/KEY: MISC_FEATURE
<222> LOCATION: (6)..(6)
<223> OTHER INFORMATION: Phe or Trp
<220> FEATURE:
<221> NAME/KEY: MISC_FEATURE
<222> LOCATION: (7)..(7)
<223> OTHER INFORMATION: Phe or Trp
<220> FEATURE:
<221> NAME/KEY: MISC_FEATURE
<222> LOCATION: (8)..(8)
<223> OTHER INFORMATION: Lys or Arg
<220> FEATURE:
<221> NAME/KEY: MISC_FEATURE
<222> LOCATION: (9)..(9)
<223> OTHER INFORMATION: Lys or Arg
<220> FEATURE:
<221> NAME/KEY: MISC_FEATURE
<222> LOCATION: (10)..(10)
<223> OTHER INFORMATION: Leu, Phe, or Trp
<220> FEATURE:
<221> NAME/KEY: MISC_FEATURE
<222> LOCATION: (11)..(11)
<223> OTHER INFORMATION: Lys or Arg

<400> SEQUENCE: 1

Xaa Xaa Xaa Xaa Xaa Xaa Xaa Xaa Xaa Xaa Xaa
1               5                   10

<210> SEQ ID NO 2
<211> LENGTH: 11
<212> TYPE: PRT
<213> ORGANISM: Artificial Sequence
<220> FEATURE:
<223> OTHER INFORMATION: Peptide

<400> SEQUENCE: 2

Lys Arg Phe Lys Lys Phe Phe Lys Lys Leu Lys
1               5                   10

<210> SEQ ID NO 3
<211> LENGTH: 11
<212> TYPE: PRT
<213> ORGANISM: Artificial Sequence
<220> FEATURE:
<223> OTHER INFORMATION: Peptide

<400> SEQUENCE: 3

Lys Arg Ala Lys Lys Phe Phe Lys Lys Pro Lys
1               5                   10

<210> SEQ ID NO 4
<211> LENGTH: 11
<212> TYPE: PRT
<213> ORGANISM: Artificial Sequence
```

```
<220> FEATURE:
<223> OTHER INFORMATION: Peptide

<400> SEQUENCE: 4

Lys Arg Ala Lys Lys Phe Phe Lys Lys Leu Lys
1               5                   10

<210> SEQ ID NO 5
<211> LENGTH: 11
<212> TYPE: PRT
<213> ORGANISM: Artificial Sequence
<220> FEATURE:
<223> OTHER INFORMATION: Peptide

<400> SEQUENCE: 5

Lys Lys Ala Lys Lys Phe Phe Lys Lys Leu Lys
1               5                   10

<210> SEQ ID NO 6
<211> LENGTH: 11
<212> TYPE: PRT
<213> ORGANISM: Artificial Sequence
<220> FEATURE:
<223> OTHER INFORMATION: Peptide

<400> SEQUENCE: 6

Lys Arg Ala Lys Lys Phe Phe Lys Arg Leu Lys
1               5                   10

<210> SEQ ID NO 7
<211> LENGTH: 11
<212> TYPE: PRT
<213> ORGANISM: Artificial Sequence
<220> FEATURE:
<223> OTHER INFORMATION: Peptide

<400> SEQUENCE: 7

Lys Arg Ala Lys Arg Phe Phe Lys Arg Leu Lys
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Peptide

<400> SEQUENCE: 8

Arg Arg Ala Lys Arg Phe Phe Lys Arg Leu Lys
1               5                   10

<210> SEQ ID NO 9
<211> LENGTH: 11
<212> TYPE: PRT
<213> ORGANISM: Artificial Sequence
<220> FEATURE:
<223> OTHER INFORMATION: Peptide

<400> SEQUENCE: 9

Arg Arg Phe Lys Arg Phe Phe Lys Arg Leu Lys
1               5                   10

<210> SEQ ID NO 10
<211> LENGTH: 11
<212> TYPE: PRT
<213> ORGANISM: Artificial Sequence
<220> FEATURE:
```

<223> OTHER INFORMATION: Peptide

<400> SEQUENCE: 10

Arg Arg Phe Arg Arg Phe Phe Arg Arg Leu Arg
1               5                   10

<210> SEQ ID NO 11
<211> LENGTH: 11
<212> TYPE: PRT
<213> ORGANISM: Artificial Sequence
<220> FEATURE:
<223> OTHER INFORMATION: Peptide

<400> SEQUENCE: 11

Lys Arg Phe Lys Lys Phe Phe Lys Lys Phe Lys
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Peptide

<400> SEQUENCE: 12

Lys Arg Trp Lys Lys Phe Phe Lys Lys Trp Lys
1               5                   10

<210> SEQ ID NO 13
<211> LENGTH: 11
<212> TYPE: PRT
<213> ORGANISM: Artificial Sequence
<220> FEATURE:
<223> OTHER INFORMATION: Peptide

<400> SEQUENCE: 13

Lys Arg Trp Lys Lys Trp Phe Lys Lys Trp Lys
1               5                   10

<210> SEQ ID NO 14
<211> LENGTH: 11
<212> TYPE: PRT
<213> ORGANISM: Artificial Sequence
<220> FEATURE:
<223> OTHER INFORMATION: Peptide

<400> SEQUENCE: 14

Lys Arg Trp Lys Lys Trp Trp Lys Lys Trp Lys
1               5                   10

<210> SEQ ID NO 15
<211> LENGTH: 11
<212> TYPE: PRT
<213> ORGANISM: Artificial Sequence
<220> FEATURE:
<223> OTHER INFORMATION: Peptide

<400> SEQUENCE: 15

Arg Arg Trp Lys Arg Phe Phe Lys Arg Trp Lys
1               5                   10

<210> SEQ ID NO 16
<211> LENGTH: 8
<212> TYPE: PRT
<213> ORGANISM: Artificial Sequence
<220> FEATURE:
<223> OTHER INFORMATION: Peptide

```
<220> FEATURE:
<221> NAME/KEY: MISC_FEATURE
<222> LOCATION: (1)..(1)
<223> OTHER INFORMATION: absent or Gly
<220> FEATURE:
<221> NAME/KEY: MISC_FEATURE
<222> LOCATION: (2)..(2)
<223> OTHER INFORMATION: absent or Gly
<220> FEATURE:
<221> NAME/KEY: MISC_FEATURE
<222> LOCATION: (3)..(3)
<223> OTHER INFORMATION: absent, a hydrophobic amino acid, Arg, or
      Citrulline
<220> FEATURE:
<221> NAME/KEY: MISC_FEATURE
<222> LOCATION: (4)..(4)
<223> OTHER INFORMATION: a hydrophobic amino acid, Arg, or Citrulline
<220> FEATURE:
<221> NAME/KEY: MISC_FEATURE
<222> LOCATION: (5)..(5)
<223> OTHER INFORMATION: a hydrophobic amino acid, Arg, or Citrulline
<220> FEATURE:
<221> NAME/KEY: MISC_FEATURE
<222> LOCATION: (6)..(6)
<223> OTHER INFORMATION: a hydrophobic amino acid, Arg, or Citrulline
<220> FEATURE:
<221> NAME/KEY: MISC_FEATURE
<222> LOCATION: (7)..(7)
<223> OTHER INFORMATION: a hydrophobic amino acid, Arg, or Citrulline
<220> FEATURE:
<221> NAME/KEY: MISC_FEATURE
<222> LOCATION: (8)..(8)
<223> OTHER INFORMATION: a hydrophobic amino acid, Arg, or Citrulline
<220> FEATURE:
<221> NAME/KEY: MISC_FEATURE
<222> LOCATION: (9)..(9)
<223> OTHER INFORMATION: a hydrophobic amino acid, Arg, Citrulline, or
      Tyr
<220> FEATURE:
<221> NAME/KEY: MISC_FEATURE
<222> LOCATION: (10)..(10)
<223> OTHER INFORMATION: absent, a hydrophobic amino acid, Arg, or
      Citrulline

<400> SEQUENCE: 16

Xaa Xaa Xaa Xaa Xaa Xaa Xaa Xaa
1               5

<210> SEQ ID NO 17
<211> LENGTH: 8
<212> TYPE: PRT
<213> ORGANISM: Artificial Sequence
<220> FEATURE:
<223> OTHER INFORMATION: Peptide

<400> SEQUENCE: 17

Val Ile Gly Val Thr Phe Pro Phe
1               5

<210> SEQ ID NO 18
<211> LENGTH: 8
<212> TYPE: PRT
<213> ORGANISM: Artificial Sequence
<220> FEATURE:
<223> OTHER INFORMATION: Peptide

<400> SEQUENCE: 18

Val Ile Gly Val Ser Ile Pro Phe
1               5

<210> SEQ ID NO 19
<211> LENGTH: 8
<212> TYPE: PRT
```

```
<213> ORGANISM: Artificial Sequence
<220> FEATURE:
<223> OTHER INFORMATION: Peptide

<400> SEQUENCE: 19

Val Ile Gly Val Thr Ile Pro Phe
1               5

<210> SEQ ID NO 20
<211> LENGTH: 10
<212> TYPE: PRT
<213> ORGANISM: Artificial Sequence
<220> FEATURE:
<223> OTHER INFORMATION: Peptide

<400> SEQUENCE: 20

Gly Gly Val Ile Gly Val Thr Phe Pro Phe
1               5                   10

<210> SEQ ID NO 21
<211> LENGTH: 10
<212> TYPE: PRT
<213> ORGANISM: Artificial Sequence
<220> FEATURE:
<223> OTHER INFORMATION: Peptide

<400> SEQUENCE: 21

Gly Gly Val Ile Gly Val Ser Ile Pro Phe
1               5                   10

<210> SEQ ID NO 22
<211> LENGTH: 10
<212> TYPE: PRT
<213> ORGANISM: Artificial Sequence
<220> FEATURE:
<223> OTHER INFORMATION: Peptide

<400> SEQUENCE: 22

Gly Gly Val Ile Gly Val Thr Ile Pro Phe
1               5                   10

<210> SEQ ID NO 23
<211> LENGTH: 4
<212> TYPE: PRT
<213> ORGANISM: Artificial Sequence
<220> FEATURE:
<223> OTHER INFORMATION: Peptide

<400> SEQUENCE: 23

Gly Gly Gly Gly
1

<210> SEQ ID NO 24
<211> LENGTH: 6
<212> TYPE: PRT
<213> ORGANISM: Artificial Sequence
<220> FEATURE:
<223> OTHER INFORMATION: Peptide

<400> SEQUENCE: 24

Gly Gly Gly Gly Gly Gly
1               5

<210> SEQ ID NO 25
<211> LENGTH: 5
<212> TYPE: PRT
<213> ORGANISM: Artificial Sequence
```

```
<220> FEATURE:
<223> OTHER INFORMATION: Peptide

<400> SEQUENCE: 25

Gly Pro Asn Gly Gly
1               5

<210> SEQ ID NO 26
<211> LENGTH: 6
<212> TYPE: PRT
<213> ORGANISM: Artificial Sequence
<220> FEATURE:
<223> OTHER INFORMATION: Peptide

<400> SEQUENCE: 26

Gly Gly Ser Gly Gly Ser
1               5

<210> SEQ ID NO 27
<211> LENGTH: 5
<212> TYPE: PRT
<213> ORGANISM: Artificial Sequence
<220> FEATURE:
<223> OTHER INFORMATION: Peptide

<400> SEQUENCE: 27

Pro Ser Pro Ser Pro
1               5

<210> SEQ ID NO 28
<211> LENGTH: 5
<212> TYPE: PRT
<213> ORGANISM: Artificial Sequence
<220> FEATURE:
<223> OTHER INFORMATION: Peptide

<400> SEQUENCE: 28

Ala Ser Ala Ser Ala
1               5

<210> SEQ ID NO 29
<211> LENGTH: 7
<212> TYPE: PRT
<213> ORGANISM: Artificial Sequence
<220> FEATURE:
<223> OTHER INFORMATION: Peptide

<400> SEQUENCE: 29

Pro Ser Pro Ser Pro Ser Pro
1               5

<210> SEQ ID NO 30
<211> LENGTH: 4
<212> TYPE: PRT
<213> ORGANISM: Artificial Sequence
<220> FEATURE:
<223> OTHER INFORMATION: Peptide

<400> SEQUENCE: 30

Lys Lys Lys Lys
1

<210> SEQ ID NO 31
<211> LENGTH: 4
<212> TYPE: PRT
<213> ORGANISM: Artificial Sequence
<220> FEATURE:
```

<223> OTHER INFORMATION: Peptide

<400> SEQUENCE: 31

Arg Arg Arg Arg
1

<210> SEQ ID NO 32
<211> LENGTH: 15
<212> TYPE: PRT
<213> ORGANISM: Artificial Sequence
<220> FEATURE:
<223> OTHER INFORMATION: Peptide

<400> SEQUENCE: 32

Gly Gly Gly Gly Ser Gly Gly Gly Gly Ser Gly Gly Gly Gly Ser
1               5                   10                  15

<210> SEQ ID NO 33
<211> LENGTH: 5
<212> TYPE: PRT
<213> ORGANISM: Artificial Sequence
<220> FEATURE:
<223> OTHER INFORMATION: Peptide

<400> SEQUENCE: 33

Gly Gly Gly Gly Ser
1               5

<210> SEQ ID NO 34
<211> LENGTH: 10
<212> TYPE: PRT
<213> ORGANISM: Artificial Sequence
<220> FEATURE:
<223> OTHER INFORMATION: Peptide

<400> SEQUENCE: 34

Gly Gly Gly Gly Ser Gly Gly Gly Gly Ser
1               5                   10

<210> SEQ ID NO 35
<211> LENGTH: 20
<212> TYPE: PRT
<213> ORGANISM: Artificial Sequence
<220> FEATURE:
<223> OTHER INFORMATION: Peptide

<400> SEQUENCE: 35

Gly Gly Gly Gly Ser Gly Gly Gly Gly Ser Gly Gly Gly Gly Ser Gly
1               5                   10                  15

Gly Gly Gly Ser
            20

<210> SEQ ID NO 36
<211> LENGTH: 25
<212> TYPE: PRT
<213> ORGANISM: Artificial Sequence
<220> FEATURE:
<223> OTHER INFORMATION: Peptide

<400> SEQUENCE: 36

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

```
<210> SEQ ID NO 37
<211> LENGTH: 30
<212> TYPE: PRT
<213> ORGANISM: Artificial Sequence
<220> FEATURE:
<223> OTHER INFORMATION: Peptide

<400> SEQUENCE: 37

Gly Gly Gly Gly Ser Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 38
<211> LENGTH: 21
<212> TYPE: PRT
<213> ORGANISM: Artificial Sequence
<220> FEATURE:
<223> OTHER INFORMATION: Peptide

<400> SEQUENCE: 38

Lys Arg Phe Lys Lys Phe Phe Lys Lys Leu Lys Gly Gly Val Ile Gly
1               5                   10                  15

Val Thr Phe Pro Phe
            20

<210> SEQ ID NO 39
<211> LENGTH: 21
<212> TYPE: PRT
<213> ORGANISM: Artificial Sequence
<220> FEATURE:
<223> OTHER INFORMATION: Peptide

<400> SEQUENCE: 39

Lys Arg Ala Lys Lys Phe Phe Lys Lys Leu Lys Gly Gly Val Ile Gly
1               5                   10                  15

Val Thr Phe Pro Phe
            20

<210> SEQ ID NO 40
<211> LENGTH: 21
<212> TYPE: PRT
<213> ORGANISM: Artificial Sequence
<220> FEATURE:
<223> OTHER INFORMATION: Peptide

<400> SEQUENCE: 40

Lys Lys Ala Lys Lys Phe Phe Lys Lys Leu Lys Gly Gly Val Ile Gly
1               5                   10                  15

Val Thr Phe Pro Phe
            20

<210> SEQ ID NO 41
<211> LENGTH: 21
<212> TYPE: PRT
<213> ORGANISM: Artificial Sequence
<220> FEATURE:
<223> OTHER INFORMATION: Peptide

<400> SEQUENCE: 41

Lys Arg Ala Lys Lys Phe Phe Lys Arg Leu Lys Gly Gly Val Ile Gly
1               5                   10                  15

Val Thr Phe Pro Phe
            20
```

<210> SEQ ID NO 42
<211> LENGTH: 21
<212> TYPE: PRT
<213> ORGANISM: Artificial Sequence
<220> FEATURE:
<223> OTHER INFORMATION: Peptide

<400> SEQUENCE: 42

```
Lys Arg Ala Lys Arg Phe Phe Lys Arg Leu Lys Gly Gly Val Ile Gly
1               5                   10                  15

Val Thr Phe Pro Phe
            20
```

<210> SEQ ID NO 43
<211> LENGTH: 21
<212> TYPE: PRT
<213> ORGANISM: Artificial Sequence
<220> FEATURE:
<223> OTHER INFORMATION: Peptide

<400> SEQUENCE: 43

```
Arg Arg Ala Lys Arg Phe Phe Lys Arg Leu Lys Gly Gly Val Ile Gly
1               5                   10                  15

Val Thr Phe Pro Phe
            20
```

<210> SEQ ID NO 44
<211> LENGTH: 21
<212> TYPE: PRT
<213> ORGANISM: Artificial Sequence
<220> FEATURE:
<223> OTHER INFORMATION: Peptide

<400> SEQUENCE: 44

```
Arg Arg Phe Lys Arg Phe Phe Lys Arg Leu Lys Gly Gly Val Ile Gly
1               5                   10                  15

Val Thr Phe Pro Phe
            20
```

<210> SEQ ID NO 45
<211> LENGTH: 21
<212> TYPE: PRT
<213> ORGANISM: Artificial Sequence
<220> FEATURE:
<223> OTHER INFORMATION: Peptide

<400> SEQUENCE: 45

```
Arg Arg Phe Arg Arg Phe Phe Arg Arg Leu Arg Gly Gly Val Ile Gly
1               5                   10                  15

Val Thr Phe Pro Phe
            20
```

<210> SEQ ID NO 46
<211> LENGTH: 21
<212> TYPE: PRT
<213> ORGANISM: Artificial Sequence
<220> FEATURE:
<223> OTHER INFORMATION: Peptide

<400> SEQUENCE: 46

```
Lys Arg Phe Lys Lys Phe Phe Lys Lys Phe Lys Gly Gly Val Ile Gly
1               5                   10                  15

Val Thr Phe Pro Phe
            20
```

<210> SEQ ID NO 47
<211> LENGTH: 21
<212> TYPE: PRT
<213> ORGANISM: Artificial Sequence
<220> FEATURE:
<223> OTHER INFORMATION: Peptide

<400> SEQUENCE: 47

Lys Arg Trp Lys Lys Phe Phe Lys Lys Trp Lys Gly Gly Val Ile Gly
1               5                   10                  15

Val Thr Phe Pro Phe
            20

<210> SEQ ID NO 48
<211> LENGTH: 21
<212> TYPE: PRT
<213> ORGANISM: Artificial Sequence
<220> FEATURE:
<223> OTHER INFORMATION: Peptide

<400> SEQUENCE: 48

Lys Arg Trp Lys Lys Trp Phe Lys Lys Trp Lys Gly Gly Val Ile Gly
1               5                   10                  15

Val Thr Phe Pro Phe
            20

<210> SEQ ID NO 49
<211> LENGTH: 21
<212> TYPE: PRT
<213> ORGANISM: Artificial Sequence
<220> FEATURE:
<223> OTHER INFORMATION: Peptide

<400> SEQUENCE: 49

Lys Arg Trp Lys Lys Trp Trp Lys Lys Trp Lys Gly Gly Val Ile Gly
1               5                   10                  15

Val Thr Phe Pro Phe
            20

<210> SEQ ID NO 50
<211> LENGTH: 21
<212> TYPE: PRT
<213> ORGANISM: Artificial Sequence
<220> FEATURE:
<223> OTHER INFORMATION: Peptide

<400> SEQUENCE: 50

Arg Arg Trp Lys Arg Phe Phe Lys Arg Trp Lys Gly Gly Val Ile Gly
1               5                   10                  15

Val Thr Phe Pro Phe
            20

<210> SEQ ID NO 51
<211> LENGTH: 34
<212> TYPE: PRT
<213> ORGANISM: Naja atra

<400> SEQUENCE: 51

Lys Arg Phe Lys Lys Phe Phe Lys Lys Leu Lys Asn Ser Val Lys Lys
1               5                   10                  15

Arg Ala Lys Lys Phe Phe Lys Lys Pro Lys Val Ile Gly Val Thr Phe
            20                  25                  30

```
Pro Phe

<210> SEQ ID NO 52
<211> LENGTH: 34
<212> TYPE: PRT
<213> ORGANISM: Artificial Sequence
<220> FEATURE:
<223> OTHER INFORMATION: Peptide

<400> SEQUENCE: 52

Lys Arg Phe Lys Lys Phe Phe Lys Lys Val Lys Lys Ser Val Lys Lys
1               5                   10                  15

Arg Leu Lys Lys Ile Phe Lys Lys Pro Met Val Ile Gly Val Thr Ile
            20                  25                  30

Pro Phe

<210> SEQ ID NO 53
<211> LENGTH: 26
<212> TYPE: PRT
<213> ORGANISM: Artificial Sequence
<220> FEATURE:
<223> OTHER INFORMATION: Peptide

<400> SEQUENCE: 53

Lys Arg Phe Lys Lys Phe Phe Lys Lys Leu Lys Asn Ser Val Lys Lys
1               5                   10                  15

Arg Ala Lys Lys Phe Phe Lys Lys Pro Lys
            20                  25
```

ANTIMICROBIAL AND ANTICANCER PEPTIDES AND CONJUGATES AND COMPOSITIONS, METHODS, ARTICLES AND KITS RELATING THERETO

CROSS-REFERENCE TO RELATED APPLICATION

This non-provisional application claims the benefit under 35 U.S.C. § 119(e) to U.S. Provisional Application No. 62/778,964, filed on Dec. 13, 2018, which is hereby expressly incorporated by reference into the present application.

GOVERNMENT INTERESTS

This invention was made with government support under Grant No. HDTRA1-12-C-0039 awarded by the Defense Threat Reduction Agency. The government has certain rights in the invention.

REFERENCE TO SEQUENCE LISTING

The Sequence Listing concurrently submitted herewith as a text file named "381789_7000US1_Sequence_Listing.txt," created on Apr. 16, 2021 and having a size of 13,647 bytes is herein incorporated by reference pursuant to 37 C.F.R. § 1.52(e)(5).

FIELD OF THE INVENTION

The present invention relates to peptides and conjugates including peptides and conjugates comprising antimicrobial and/or anticancer properties, to compositions, kits, and articles of manufacture comprising such peptides and conjugates, as well as to methods for using the peptides and conjugates.

BACKGROUND

While a diverse range of therapeutic strategies have been explored including for the delivery of antimicrobial and/or anticancer agents, such strategies often show toxic effect on normal cells. For example, constructs based on chlorine conjugated to polylysines of varied lengths and varied degrees of substitution have been investigated against representative gram-negative and gram-positive bacteria for the intracellular delivery of the photosensitizer (chlorine). In these studies, cells were treated with the conjugate and then exposed to 660 nm light, which triggers the generation of singlet oxygen and free radicals leading to cell death. Polylysine conjugates are generally not well suited for systemic administration. They tend to provide limited specificity in their delivery of attached drug moieties by entering host cells, as well as invading microbes. Similar polylysine peptides have been used for the transduction of proteins across the membranes of mammalian cells.

There is a need for new and effective antimicrobial and/or anticancer agents as well as therapeutic, prophylactic, and/or diagnostic methods and strategies that target microbial organisms and/or cancerous cells.

SUMMARY OF THE INVENTION

In one aspect, the present invention provides a peptide comprising:
(a) the amino acid sequence set forth in Formula (I) (SEQ ID NO:1):

$$X_{aa1}\ X_{aa2}\ X_{aa3}\ X_{aa4}\ X_{aa5}\ X_{aa6}\ X_{aa7}\ X_{aa8}\ X_{aa9}\ X_{aa10}\ X_{aa11}$$

wherein independently of each other:
$X_{aa1}$ is Lys or Arg,
$X_{aa2}$ is Lys or Arg,
$X_{aa3}$ is Phe, Ala, or Trp,
$X_{aa4}$ is Lys or Arg,
$X_{aa5}$ is Lys or Arg,
$X_{aa6}$ is Phe or Trp,
$X_{aa7}$ is Phe or Trp,
$X_{aa8}$ is Lys or Arg,
$X_{aa9}$ is Lys or Arg,
$X_{aa10}$ is Leu, Phe, or Trp, and
$X_{aa11}$ is Lys or Arg; or
(b) the amino acid sequence set forth in Formula (I) (SEQ ID NO:1) with one substitution, insertion, addition, or deletion.

In another aspect, the present invention provides a polynucleotide encoding the peptide of Formula (I) (SEQ ID NO:1).

In other aspects, the present invention provides a composition comprising the peptide of Formula (I) (SEQ ID NO:1) or the polynucleotide encoding the peptide of Formula (I) (SEQ ID NO:1).

In some aspects, the present invention provides an article of manufacture comprising the peptide of Formula (I) (SEQ ID NO:1).

In one aspect, the present invention provides a kit comprising the peptide of Formula (I) (SEQ ID NO:1) or the polynucleotide encoding the peptide of Formula (I) (SEQ ID NO:1).

In another aspect, the present invention provides a method for treating infection by a microbial organism in a subject. The method comprises administering to the subject the peptide of Formula (I) (SEQ ID NO:1) or the polynucleotide encoding the peptide of Formula (I) (SEQ ID NO:1).

In other aspects, the present invention provides a method for preventing, reducing or inhibiting growth of a microbial organism or biofilm on a surface. The method comprises contacting the surface with a composition comprising the peptide of Formula (I) (SEQ ID NO:1).

In some aspects, the present invention provides a method for promoting wound healing in a subject. The method comprises administering to the subject the peptide of Formula (I) (SEQ ID NO:1) or the polynucleotide encoding the peptide of Formula (I) (SEQ ID NO:1).

In one aspect, the present invention provides a method for treating or preventing endotoxemia in a subject. The method comprises administering to the subject an amount of the peptide of Formula (I) (SEQ ID NO:1) effective to treat or prevent endotoxemia in the subject.

In another aspect, the present invention provides a method for determining an lipopolysaccharide (LPS) or an lipoteichoic acid (LTA) in a sample. The method comprises contacting the sample with the peptide of Formula (I) (SEQ ID NO:1) under a condition such that the LPS or the LTA binds to the peptide to form a complex; and detecting the complex.

In some aspects, the present invention provides a method for diagnosing an LPS- or an LTA-associated disorder in a subject. The method comprises forming a complex between an LPS or an LTA and the peptide of Formula (I) (SEQ ID NO:1) under a condition such that the LPS or the LTA binds to the peptide to form the complex; and detecting the complex.

In other aspects, the present invention provides a method for treating a composition comprising an LPS or an LTA. The method comprises contacting the composition with the peptide of Formula (I) (SEQ ID NO:1) under a condition such that the LPS or the LTA binds to the peptide to form a complex; and separating the complex from the composition, thereby reducing or eliminating the LPS or the LTA from the composition.

In some aspects, the present provides a method for determining the presence of bacteria in a sample. The method comprises contacting the sample with the peptide of Formula (I) (SEQ ID NO:1) under a condition such that the bacteria bind to the peptide to form a complex; and detecting the complex. The peptide may be in free form or conjugated to an agent or bound to another solid phase.

In other aspects, the present provides a method for isolating bacteria from a sample. The method comprises contacting the sample with the peptide of Formula (I) (SEQ ID NO:1) under a condition such that the bacteria bind to the peptide to form a complex; and isolating the complex. The peptide may be in free form or conjugated to an agent or bound to another solid phase.

In one aspect, the present invention provides a method for treating or preventing a cancer in a subject in need thereof. The method comprises administering to the subject a therapeutically or prophylactically effective amount of the peptide of Formula (I) (SEQ ID NO:1), or a composition comprising the peptide or a polynucleotide encoding the peptide.

In one aspect, the present invention provides a conjugate comprising the peptide of Formula (I) (SEQ ID NO:1) conjugated to an agent, wherein the peptide is connected to the agent directly or through a linker segment, the agent being connected to the peptide or the linker segment through a stable or cleavable bond, wherein the conjugate carries and facilitates the delivery of the conjugated agent to a microbe or a cancer cell.

In one aspect, the present invention provides a method for targeting delivery of an agent to a cell in a subject, the method comprising administering to the subject the conjugate provided herein.

In some aspects, the present provides a method for determining the presence of tumor cells in a sample. The method comprises contacting the sample with the peptide of Formula (I) (SEQ ID NO:1) under a condition such that the tumor cell binds to the peptide to form a complex; and detecting the complex. The peptide may be in free form or conjugated to an agent or bound to another solid phase.

In other aspects, the present provides a method for isolating tumor cell from a sample. The method comprises contacting the sample with the peptide of Formula (I) (SEQ ID NO:1) under a condition such that the tumor cell binds to the peptide to form a complex; and isolating the complex. The peptide may be in free form or conjugated to an agent or bound to another solid phase.

In one aspect, the present invention provides a method for increasing the transferability across cell-membrane of an agent to be delivered to a cell present in a subject the method comprising administering to the subject the conjugate provided herein.

In other aspects, the present invention provides a method for increasing the transferability across cell-membrane of an agent to be delivered to a cell ex vivo, the method comprising contacting the cell with the conjugate provided herein.

DETAILED DESCRIPTION OF THE INVENTION

Figure 1:
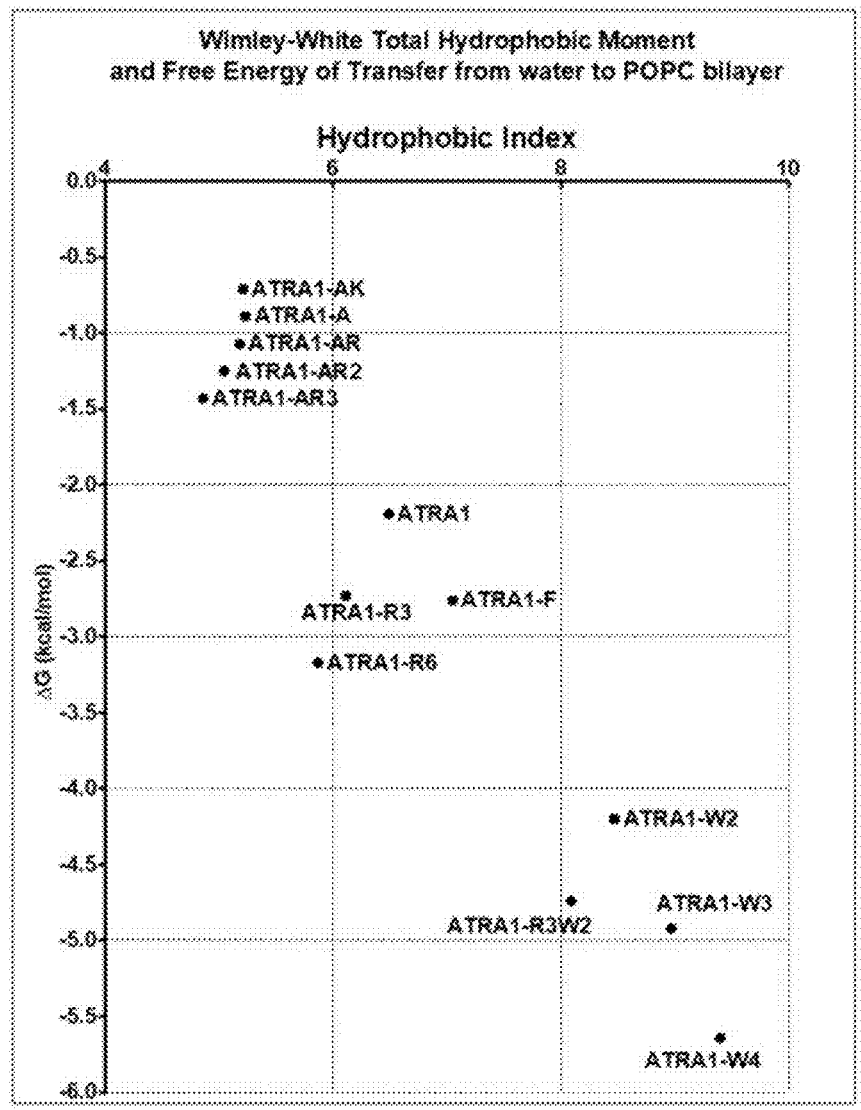
FIG. 1 is a Wimley-White Plot of Hydrophobic Index and Free Energy of Transfer. The figure depicts how the likeness of the peptide to translocate from water to POPC membrane interfaces depends on the specific sequence. The Total Hydrophobic Moment is on the x-axis and Free Energy of Transfer is on the y-axis.

Disclosed herein are peptides, as well as compositions, conjugates, methods, articles, and kits related to peptides, including antimicrobial peptides (AMPS) and anti-cancer peptides/constructs, and strategies for leveraging the therapeutic and/or prophylactic potential thereof. According to various aspects and embodiments, the peptides, conjugates, compositions, methods, articles, and kits provided herein can be used, among other things, for targeting a cell (e.g., a microbe, a cancer or tumor cell, a cell containing membranes differing from a normal healthy cell, cells with distinct membranes including, for example, cysts and cystic fibrosis), including for targeting a cell for therapeutic and/or prophylactic treatment and/or prevention of cancers and/or of infections, wounds and/or biofilms, including infections, wounds and/or biofilms that involve a microbial organism including, but not limited to, a microbial organism that may be classified or otherwise characterized as a biodefense and/or drug- or multidrug-resistant/tolerant pathogen.

In some embodiments, the microbial organism is a bacterial strain, virus, fungus, or protozoa.

In one embodiment, the bacterial strain is a Gram-negative or Gram-positive bacterial strain.

In another embodiment, the bacterial strain is of the genus *Francisela, Acinetobacter, Pseudomonas, Klebsiella, Escherichia, Haemophilus, Proteus, Enterobacter, Serratia, Burkholderia, Stenotrophomonas, Alcaligenes, Mycobacterium, Legionella, Neisseria, Yersinia, Shigella, Vibrio*, or *Salmonella*.

In other embodiments, the bacterial strain is *Francisela tularensis, Acinetobacter baumannii, Pseudomonas aeruginosa, Klebsiella pneumoniae, Klebsiella oxytoca, Escherichia coli, Haemophilus influenzae, Proteus mirabilis, Enterobacter species, Serratia marcescens, Burkholderia cepacia, Stenotrophomonas maltophilia, Alcaligenes xylosoxidans, Mycobacterium tuberculosis, Neisseria gonorrhoeae, Yersinia pestis, Shigella dysenteriae, Vibrio cholera*, or *Salmonella typhi*.

In one embodiment, the bacterial strain is *Francisela tularensis, Francisela novicida, Francisela hispaniensis, Francisela noatunensis, Francisela philomiragia, Francisela halioticida, Francisela endociliophora, Francisela guangzhouensis*, or *Francisela piscicida*.

In another embodiment, the bacterial strain is *Francisela tularensis*.

In other embodiments, the bacterial strain is of the genus *Staphylococcus, Bacillus, Rhodococcus, Actinobacteria, Lactobacillus, Actinomyces, Clostridium*, or *Streptococcus*.

In some embodiments, the bacterial strain is *Staphylococcus aureus, Bacillus anthracis, Streptococcus mutans* or *Streptococcus sanguinis*.

In other embodiments, viruses include but are not limited to influenza virus, parainfluenza virus, respiratory syncytial virus, human metapneumovirus, corona virus family members, human immunodeficiency virus, herpes simplex virus, cytomegalovirus, SARS (Severe Acute Respiratory Syndrome) virus, and Epstein-Barr virus.

In some embodiments, fungi include but are not limited to *Histoplasma capsulatum, Coccidioides immitis, Blastomyces dermatitidis, Paracoccidioides brasiliensis, Candida* sp., *Aspergillus* sp., *Mucor* sp., *Cryptococcus neoformans*.

In other embodiments, protozoa include but are not limited to *Entamoeba, Acanthamoeba, Balamuthia, Leishmania, Trypanosoma, Trichomonas, Lophomonas, Cryptosporidium, Cyclospora, Toxoplasma, Plasmodium, Babesia, Encephalitozoon, Enterocytozoon* and *Balantidium*.

Some non-limiting examples of cancer include carcinoma, melanoma, lymphoma, blastoma, sarcoma, germ cell tumors, and leukemia or lymphoid malignancies. Non-limiting examples of cancers that fall within these broad categories include squamous cell cancer (e.g., epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including lung cancer, gastrointestinal cancer, pancreatic cancer, glioblastoma, cervical cancer, ovarian cancer, liver cancer, bladder cancer, cancer of the urinary tract, hepatoma, breast cancer, rectal cancer, colon cancer, colorectal cancer, endometrial or uterine carcinoma, salivary gland carcinoma, kidney or renal cancer, prostate cancer, vulval cancer, thyroid cancer, hepatic carcinoma, anal carcinoma, melanoma, multiple myeloma and B-cell lymphoma, brain, as well as head and neck cancer, and associated metastases.

In other embodiments, cancer also encompasses cell proliferative disorders which are associated with some degree of abnormal cell proliferation and includes, but not limited to, tumors, which include neoplasms or neoplastic cell growth and proliferation, whether malignant or benign, and all pre-cancerous and cancerous cells and tissues. In one embodiment, the cancer is a lung cancer. In some embodiments, the lung cancer is an adenocarcinoma, a squamous cell carcinoma, a large cell carcinoma, a small cell lung cancer, an adenosquamous carcinoma, or a sarcomatoid carcinoma.

In another embodiment, a cell can be a cell containing membranes differing from normal healthy cells. In some embodiments, a cell can be a cell with a distinct membrane including, but not limited to, cysts, cystic fibrosis cells, tumor and cancer cells. In other embodiments, the cell comprises a cell membrane having a net-negative charge characteristic.

Subjects that can be administered or otherwise benefit from the peptides, compositions, methods, articles, and kits provided herein include vertebrates such as, without limitation, mammals. A mammal can be a human or animal including livestock and companion animals. Companion animals include but are not limited to animals kept as pets. Examples of companion animals include cats, dogs, and horses, as well as birds, such as parrots and parakeets. Livestock refers to animals reared or raised in an agricultural setting to make products such as food or fiber, or for its labor. In some embodiments, livestock are suitable for consumption by mammals, for example humans. Examples of livestock animals include mammals, such as cattle, goats, horses, pigs, sheep, including lambs, and rabbits, as well as birds, such as chickens, ducks and turkeys.

In some embodiments, the subject is a human. In another embodiment, the subject is a non-human mammal.

In other embodiments, the subject can be a human who is a medical patient (e.g., a diabetes patient, or a patient in a hospital, clinic), a member of the armed services or law enforcement, a fire fighter, or a worker in the gas, oil, or chemical industry. In one embodiment, the subject is an animal that is a veterinarian subject/patient (e.g., livestock or companion animal).

Absent an express indication of the N-terminus and/or C-terminus of a peptide set forth herein, the peptide is to be read from the N-terminus to C-terminus. In some embodiments, individual residues are indicated by the identity of the amino acid using a standard one- and/or three-letter code known to one of ordinary skill in the art.

In some aspects, the sequence of a peptide of the present invention can be based on the sequence or portion of the 34-residue Naja atra cathelicidin (NA-CATH) peptide, which corresponds to a helical cathelicidin identified in cDNA from the venom gland of the elapid snake, Naja atra (Zhao et al., Peptides 29(10):1685-1691 (2008)). NA-CATH has the sequence KRFKKFFKKLKNSVK KRAKKFFKKPKVIGVTFPF (SEQ ID NO:51) and includes two 11 amino acid repeats (underlined) that differ from one another at the third and tenth positions (WO 2012/145680; de Latour, F. et al., Biochemical and Biophysical Research Communications 396:825-830 (2010)).

In some embodiments, the peptides provided herein can be shorter and/or variant versions of the NA-CATH peptide, including peptides having one or more substitutions, insertions, and/or deletions relative to the NA-CATH peptide sequence or a portion thereof. In other embodiments, the peptides have one or more biological activities (e.g., antimicrobial and/or anticancer and/or bacteria-binding and/or tumor cell-binding).

In some embodiments, the peptides provided herein can include one or more (e.g., one, two, three, four, five or more) substitutions, insertions, deletions, and/or additions (and combinations thereof) as compared to the NA-CATH sequence set forth in SEQ ID NO:51.

Amino acid substitutions can be conservative or non-conservative amino acid substitutions. Conservative amino acid substitutions can be, for example, aspartic-glutamic as acidic amino acids; lysine/arginine/histidine as basic amino acids; leucine/isoleucine, methionine/valine, alanine/valine as hydrophobic amino acids; serine/glycine/alanine/threonine as hydrophilic amino acids. Conservative amino acid substitutions also include groupings based on side chains. For example, amino acids having aliphatic side chains such as glycine, alanine, valine, leucine, and isoleucine; amino acids having aliphatic-hydroxyl side chains such as serine and threonine; amino acids having amide-containing side chains such as asparagine, glutamine and citrulline; amino acids having aromatic side chains such as phenylalanine, tyrosine, and tryptophan; amino acids having basic side chains such as lysine, arginine, and histidine; and amino acids having sulfur-containing side chains such as cysteine and methionine. Non-conservative amino acid substitutions typically entail exchanging a member of one of the classes described above for a member of another class. After making an amino acid substitution, insertion, deletion, and/or addition, the activity of a peptide containing the amino acid substitution, insertion, deletion, or addition can be assessed using the assays described herein.

In some embodiment, a C-terminal amide, or other C-terminal capping moiety can be present in peptides described herein. In one embodiment, a peptide described herein is amidated at the C-terminal.

In other aspects, the present invention provides a peptide comprising:

(a) the amino acid sequence set forth in Formula (I) (SEQ ID NO:1):

$$X_{aa1}\ X_{aa2}\ X_{aa3}\ X_{aa4}\ X_{aa5}\ X_{aa6}\ X_{aa7}\ X_{aa8}\ X_{aa9}\ X_{aa10}\ X_{aa11}$$

wherein independently of each other:
$X_{aa1}$ is Lys or Arg,
$X_{aa2}$ is Lys or Arg,
$X_{aa3}$ is Phe, Ala, or Trp,
$X_{aa4}$ is Lys or Arg,
$X_{aa5}$ is Lys or Arg,
$X_{aa6}$ is Phe or Trp,
$X_{aa7}$ is Phe or Trp,
$X_{aa8}$ is Lys or Arg,
$X_{aa9}$ is Lys or Arg,
$X_{aa10}$ is Leu, Phe, or Trp, and
$X_{aa11}$ is Lys or Arg; or (b) the amino acid sequence set forth in Formula (I) (SEQ ID NO:1) with one or more substitutions, insertions, additions, or deletions.

In one embodiment, the peptide comprises:

(a) the amino acid sequence set forth in Formula (I) (SEQ ID NO:1); or (b) the amino acid sequence set forth in Formula (I) (SEQ ID NO:1) with one or more substitutions, insertions, additions, or deletions;

with the proviso that the amino acid sequence is not KRFKKFFKKLK (SEQ ID NO:2), KRAKKFFKKPK (SEQ ID NO:3), or KRAKKFFKKLK (SEQ ID NO:4).

In another embodiment, the peptide comprises the amino acid sequence KKAKKFFKKLK (SEQ ID NO:5) with one, two, three, four, or five substitutions, insertions, additions, or deletions, with the proviso that the amino acid sequence is not the sequence set forth in SEQ ID NO:2, 3, or 4. In one embodiment, the peptide comprises the amino acid sequence set forth in SEQ ID NO:5.

In some embodiments, the peptide comprises the amino acid sequence KRAKKFFKRLK (SEQ ID NO:6) with one, two, three, four, or five substitutions, insertions, additions, or deletions, with the proviso that the amino acid sequence is not the sequence set forth in SEQ ID NO:2, 3, or 4. In other embodiments, the peptide comprises the amino acid sequence set forth in SEQ ID NO:6.

In one embodiment, the peptide comprises the amino acid sequence KRAKRFFKRLK (SEQ ID NO:7) with one, two, three, four, or five substitutions, insertions, additions, or deletions, with the proviso that the amino acid sequence is not the sequence set forth in SEQ ID NO:2, 3, or 4. In another embodiment, the peptide comprises the amino acid sequence set forth in SEQ ID NO:7.

In some embodiments, the peptide comprises the amino acid sequence RRAKRFFKRLK (SEQ ID NO:8) with one, two, three, four, or five substitutions, insertions, additions, or deletions, with the proviso that the amino acid sequence is not the sequence set forth in SEQ ID NO:2, 3, or 4. In other embodiments, the peptide comprises the amino acid sequence set forth in SEQ ID NO:8.

In one embodiment, the peptide comprises the amino acid sequence RRFKRFFKRLK (SEQ ID NO:9) with one, two, three, four, or five substitutions, insertions, additions, or deletions, with the proviso that the amino acid sequence is not the sequence set forth in SEQ ID NO:2, 3, or 4. In another embodiment, the peptide comprises the amino acid sequence set forth in SEQ ID NO:9.

In some embodiments, the peptide comprises the amino acid sequence RRFRRFFRRLR (SEQ ID NO:10) with one, two, three, four, or five substitutions, insertions, additions, or deletions, with the proviso that the amino acid sequence is not the sequence set forth in SEQ ID NO:2, 3, or 4. In other embodiments, the peptide comprises the amino acid sequence set forth in SEQ ID NO:10.

In one embodiment, the peptide comprises the amino acid sequence KRFKKFFKKFK (SEQ ID NO:11) with one, two, three, four, or five substitutions, insertions, additions, or deletions, with the proviso that the amino acid sequence is not the sequence set forth in SEQ ID NO:2, 3, or 4. In another embodiment, the peptide comprises the amino acid sequence set forth in SEQ ID NO:11.

In some embodiments, the peptide comprises the amino acid sequence KRWKKFFKKWK (SEQ ID NO:12) with one, two, three, four, or five substitutions, insertions, additions, or deletions, with the proviso that the amino acid sequence is not the sequence set forth in SEQ ID NO:2, 3, or 4. In other embodiments, the peptide comprises the amino acid sequence set forth in SEQ ID NO:12.

In one embodiment, the peptide comprises the amino acid sequence KRWKKWFKKWK (SEQ ID NO:13) with one, two, three, four, or five substitutions, insertions, additions, or deletions, with the proviso that the amino acid sequence is not the sequence set forth in SEQ ID NO:2, 3, or 4. In another embodiment, the peptide comprises the amino acid sequence set forth in SEQ ID NO:13.

In some embodiments, the peptide comprises the amino acid sequence KRWKKWWKKWK (SEQ ID NO:14) with one, two, three, four, or five substitutions, insertions, additions, or deletions, with the proviso that the amino acid sequence is not the sequence set forth in SEQ ID NO:2, 3, or 4. In other embodiments, the peptide comprises the amino acid sequence set forth in SEQ ID NO:14.

In one embodiment, the peptide comprises the amino acid sequence RRWKRFFKRWK (SEQ ID NO:15) with one, two, three, four, or five substitutions, insertions, additions, or deletions, with the proviso that the amino acid sequence is not the sequence set forth in SEQ ID NO:2, 3, or 4. In another embodiment, the peptide comprises the amino acid sequence set forth in SEQ ID NO:15.

In one embodiment, the peptide is amidated at the C-terminal.

In some embodiments, the peptide further comprises a linked segment. In one embodiment, the linked segment is a C-terminal tail of the peptide.

In one embodiment, the linked segment is a hydrophobic segment comprising one or more hydrophobic moieties such as, for example, one or more hydrophobic amino acids, etc.

In another embodiment, the linked segment comprises a second amino acid sequence comprising one or more hydrophobic amino acids, for example one or more of glycine (Gly), alanine (Ala), valine (Val), leucine (Leu), isoleucine (Ile), proline (Pro), phenylalanine (Phe), methionine (Met), and/or tryptophan (Trp) and combinations thereof.

In other embodiments, the linked segment is capable of adopting a random coil structure. For example, in one embodiment, the linked segment adopts a random coil structure in the presence of an anionic lipid or liposome.

For example, the last 8-residues of NA-CATH are hydrophobic and adopt random coil structures in the presence of anionic liposomes. Without wishing to be bound by any particular theory, it is believed that the presence of unstructured C-terminal tails had demonstrated enhancement of anti-microbial and anti-endotoxin activities in some partially helical peptides.

In one embodiment, the linked segment has a linked segment amino acid sequence set forth in Formula (II) (SEQ ID NO:16): $X_{aa1} X_{aa2} X_{aa3} X_{aa4} X_{aa5} X_{aa6} X_{aa7} X_{aa8}$ wherein independently of each other:

$X_{aa1}$ is absent or Gly;

$X_{aa2}$ is absent or Gly;

$X_{aa3}$ is absent, a hydrophobic amino acid, Arg, or citrulline, $X_{aa4}$ is a hydrophobic amino acid, Arg, or citrulline, $X_{aa5}$ is a hydrophobic amino acid, Arg, or citrulline, $X_{aa6}$ is a hydrophobic amino acid, Arg, or citrulline, $X_{aa7}$ is a hydrophobic amino acid, Arg, or citrulline, $X_{aa8}$ is a hydrophobic amino acid, Arg, or citrulline, $X_{aa9}$ is a hydrophobic amino acid, Arg, citrulline, or Tyr, and $X_{aa10}$ is absent, a hydrophobic amino acid, Arg, or citrulline.

In some embodiments, the linked segment has the linked segment sequence set forth in (SEQ ID NO:16), wherein each of $X_{aa3}$-$X_{aa10}$ is a hydrophobic amino acid.

In other embodiments, the linked segment has the linked segment sequence VIGVTFPF (SEQ ID NO:17).

In another embodiment, the linked segment has the linked segment sequence VIGVSIPF (SEQ ID NO:18).

In one embodiment, the linked segment has the linked segment sequence VIGVTIPF (SEQ ID NO:19).

In other embodiments, the linked segment has the linked segment sequence GGVIGVTFPF (SEQ ID NO:20).

In another embodiment, the linked segment has the linked segment sequence GGVIGVSIPF (SEQ ID NO:21).

In one embodiment, the linked segment has the linked segment sequence GGVIGVTIPF (SEQ ID NO:22).

In some embodiments, the peptide comprises the amino acid sequence set forth in any one of SEQ ID NOs:5-15, wherein the peptide further comprises the linked segment sequence as set forth in VIGVTFPF (SEQ ID NO:17).

In other embodiments, the peptide comprises the amino acid sequence set forth in any one of SEQ ID NOs:5-15, wherein the peptide further comprises the linked segment sequence as set forth in VIGVSIPF (SEQ ID NO:18).

In other embodiments, the peptide comprises the amino acid sequence set forth in any one of SEQ ID NOs:5-15, wherein the peptide further comprises the linked segment sequence as set forth in VIGVTIPF (SEQ ID NO:19).

In some embodiments, the peptide comprises the amino acid sequence set forth in any one of SEQ ID NOs:5-15, wherein the peptide further comprises the linked segment sequence as set forth in GGVIGVTFPF (SEQ II) NO:20).

In other embodiments, the peptide comprises the amino acid sequence set forth in any one of SEQ ID NOs:5-15, wherein the peptide further comprises the linked segment sequence as set forth in GGVIGVSIPF (SEQ ID NO:21).

In other embodiments, the peptide comprises the amino acid sequence set forth in any one of SEQ ID NOs:5-15, wherein the peptide further comprises the linked segment sequence as set forth in GGVIGVTIPF (SEQ ID NO:22).

In one embodiment, a peptide described herein is amidated at the C-terminal.

In other aspects, the present invention provides peptide conjugates comprising other peptides conjugated to a linked segment described herein. In one embodiment, the linked segment is a C-terminal tail of the conjugate. In some embodiments, the linked segment comprises a linked segment sequence set forth in Formula (II) (SEQ ID NO:16). In other embodiments, the linked segment sequence comprises SEQ ID NO:17, 18, 19, 20, 21, or 22. In one embodiment, the linked segment sequence comprises SEQ ID NO:20, 21, or 22.

In one embodiment, the peptide conjugate is amidated at the C-terminal.

In another embodiment, the linked segment is covalently bonded in the peptide through a linker. In some embodiments, a linker is optional. In other embodiments, peptides are provided further having a linker as described herein, covalently linking the linked segment with the amino acid sequence of the rest of the peptide.

In some embodiments, the linker is a bond.

In one embodiment, the linker is a peptide linker.

In various embodiments, the peptide linker is a short, flexible bridging segment.

In some embodiments, the peptide linker is less than about 30 amino acids, preferably less than about 10 amino acids and more preferably about 2, 3, 4, or 5 amino acids. In one embodiment, the peptide linker comprises 2 amino acids.

In one embodiment, the linker includes from 1 to 30 or less amino acids linked by peptide bonds. The amino acids can be selected from the 20 naturally occurring (i.e., physiological) amino acids. Alternatively, non-natural amino acids can be incorporated either by chemical synthesis, post-translational chemical modification or by in vivo incorporation by recombinant expression in a host cell. Some of these amino acids may be glycosylated. In another embodiment, the 1 to 30 or less amino acids are selected from glycine, alanine, proline, asparagine, glutamine, and lysine, and further from aspartate and glutamate.

Peptide linkers include, without limitation, (shown in single-letter code): GG; GGG; GGGG (SEQ ID NO:23); GGGGGG (SEQ ID NO:24); GPNGG (SEQ ID NO:25); SGG; GGSGGS (SEQ ID NO:26); SAT; PVP; PSPSP (SEQ ID NO:27); AAA; ASA; ASASA (SEQ ID NO:28); PSPSPSP (SEQ ID NO:29); KKKK (SEQ ID NO:30); RRRR (SEQ ID NO:31); $(G_4S)_3$ (SEQ ID NO:32); GGGGS (SEQ ID NO:33); GGGGSGGGGS (SEQ ID NO:34); GGGGSGGGGSGGGGSGGGGS (SEQ ID NO:35); GGGGSGGGGSGGGGSGGGGSGGGGS (SEQ ID NO:36); and GGGGSGGGGSGGGGSGGGGSGGGGSGGGGS (SEQ ID NO:37).

In other embodiments, charged linkers may be used. Such charges linkers may contain a significant number of acidic residues (e.g., Asp, Glu, and the like), or may contain a significant number of basic residues (e.g., Lys, Arg, and the like), such that the linker has a pI (isoelectric point) lower than 7 or greater than 7, respectively. As understood by one of ordinary skill in the art, and all other things being equal, the greater the relative amount of acidic or basic residues in a given linker, the lower or higher, respectively, the pI of that linker will be. Such linkers may impart advantageous properties to the peptides disclosed herein, such as modifying the peptides pI, which can in turn improve solubility and/or stability characteristics of such peptides at a particular pH, such as at physiological pH (e.g., between pH 7.2 and pH 7.6, inclusive), or in a pharmaceutical composition including such peptides. As is known to one of ordinary skill in the art, solubility for a peptide may be improved by formulation in a composition having a pH that is at least or more than plus or minus one pH unit from the pI of the peptide.

Amino acid-based linkers can be L form, D form, combinations of L and D forms, β-form, PEG backbone, and the like.

In one embodiment, the linker comprises a diglycine (i.e., GG).

In another embodiment, the linker is a nonpeptide linker.

Nonpeptide linkers include, without limitation, PEG of any chain length (e.g., $-(CH_2-CH_2-O)_n-$ wherein n is such that the PEG linker can have a molecular weight (MW) of about 50 to about 5000 kD, or about 50 to about 500 kD, or about 50 to about 100 kD); 2-nitrobenzene or O-nitrobenzyl; nitropyridyl disulfide; dioleoylphosphatidylethanolamine (DOPE); S-acetylmercaptosuccinic acid; 1,4,7,10-tetraazacyclododecane-1,4,7,10-tetracetic acid (DOTA); β-glucuronide and β-glucuronide variants; poly(alkylacrylic acid); benzene-based linkers (for example, 2,5-Bis(hexyloxy)-1,4-bis[2,5-bis(hexyloxy)-4-formyl-phenylenevinylene]benzene) and like molecules; disulfide linkages; poly (amidoamine); carbon nanotubes; hydrazone and hydrazone variant linkers; succinate, formate, acetate butyrate, other like organic acids; aldols, alcohols, or enols; peroxides; alkane or alkene groups of any chain length; one or more porphyrin or dye molecules containing free amide and carboxylic acid groups; one or more DNA or RNA nucleotides, including polyamine and polycarboxyl-containing variants; inulin, sucrose, glucose, or other single, di or polysaccharides; linoleic acid or other polyunsaturated fatty acids; and variants of any of the aforementioned containing halogen or thiol groups.

In some embodiments, the peptide further comprising the linker and the linked segment can be chemically synthesized or recombinantly expressed as a fusion protein (i.e., a chimeric fusion protein). One of ordinary skill in the art knows how to chemically synthesize and/or recombinantly express a fusion peptide or protein.

In other embodiments, the peptide includes the linked segment at the C-terminal, and a linker that is N-terminal to the linked segment, wherein the amino acid sequence set forth in any one of SEQ ID NOs:1-15 corresponds to the N-terminal portion of the peptide. In one embodiment, expressly excluded are peptides in which the linked segment is linked directly to any one of SEQ ID NOs:1 and 5-15 without a linker.

In some embodiments, the peptide comprises the sequence KRFKKFFKKLKGGVIGVTFPF (SEQ ID NO:38), with one, two, three, four, or five substitutions, insertions, additions, or deletions, with the proviso that the amino acid sequence is not the sequence set forth in SEQ ID NO:2, 3, or 4. In one embodiment, the peptide comprises the sequence KRFKKFFKKLKGGVIGVTFPF (SEQ ID NO:38).

In other embodiments, the peptide comprises the sequence KRAKKFFKKLKGGVIGVTFPF (SEQ ID NO:39), with one, two, three, four, or five substitutions, insertions, additions, or deletions, with the proviso that the amino acid sequence is not the sequence set forth in SEQ ID NO:2, 3, or 4. In other embodiments, the peptide comprises the sequence KRAKKFFKKLKGGVIGVTFPF (SEQ ID NO:39).

In one embodiment, the peptide comprises the sequence KKAKKFFKKLKGGVIGVTFPF (SEQ ID NO:40), with one, two, three, four, or five substitutions, insertions, additions, or deletions, with the proviso that the amino acid sequence is not the sequence set forth in SEQ ID NO:2, 3, or 4. In one embodiment, the peptide comprises the sequence KKAKKFFKKLKGGVIGVTFPF (SEQ ID NO:40).

In another embodiment, the peptide comprises the sequence KRAKKFFKRLKGGVIGVTFPF (SEQ ID NO:41), with one, two, three, four, or five substitutions, insertions, additions, or deletions, with the proviso that the amino acid sequence is not the sequence set forth in SEQ ID NO:2, 3, or 4. In another embodiment, the peptide comprises the sequence KRAKKFFKRLKGGVIGVTFPF (SEQ ID NO:41).

In some embodiments, the peptide comprises the sequence KRAKRFFKRLKGGVIGVTFPF (SEQ ID NO:42), with one, two, three, four, or five substitutions, insertions, additions, or deletions, with the proviso that the amino acid sequence is not the sequence set forth in SEQ ID NO:2, 3, or 4. In some embodiments, the peptide comprises the sequence KRAKRFFKRLKGGVIGVTFPF (SEQ ID NO:42).

In other embodiments, the peptide comprises the sequence RRAKRFFKRLKGGVIGVTFPF (SEQ ID NO:43), with one, two, three, four, or five substitutions, insertions, additions, or deletions, with the proviso that the amino acid sequence is not the sequence set forth in SEQ ID NO:2, 3, or 4. In other embodiments, the peptide comprises the sequence RRAKRFFKRLKGGVIGVTFPF (SEQ ID NO:43).

In one embodiment, the peptide comprises the sequence RRFKRFFKRLKGGVIGVTFPF (SEQ ID NO:44), with one, two, three, four, or five substitutions, insertions, additions, or deletions, with the proviso that the amino acid sequence is not the sequence set forth in SEQ ID NO:2, 3, or 4. In one embodiment, the peptide comprises the sequence RRFKRFFKRLKGGVIGVTFPF (SEQ ID NO:44).

In another embodiment, the peptide comprises the sequence RRFRRFFRRLRGGVIGVTFPF (SEQ ID NO:45), with one, two, three, four, or five substitutions, insertions, additions, or deletions, with the proviso that the amino acid sequence is not the sequence set forth in SEQ ID NO:2, 3, or 4. In another embodiment, the peptide comprises the sequence RRFRRFFRRLRGGVIGVTFPF (SEQ ID NO:45).

In some embodiments, the peptide comprises the sequence KRFKKFFKKFKGGVIGVTFPF (SEQ ID NO:46), with one, two, three, four, or five substitutions, insertions, additions, or deletions, with the proviso that the amino acid sequence is not the sequence set forth in SEQ ID NO:2, 3, or 4. In some embodiments, the peptide comprises the sequence KRFKKFFKKFKGGVIGVTFPF (SEQ ID NO:46).

In other embodiments, the peptide comprises the sequence KRWKKFFKKWKGGVIGVTFPF (SEQ ID NO:47), with one, two, three, four, or five substitutions, insertions, additions, or deletions, with the proviso that the amino acid sequence is not the sequence set forth in SEQ ID NO:2, 3, or 4. In other embodiments, the peptide comprises the sequence KRWKKFFKKWKGGVIGVTFPF (SEQ ID NO:47).

In one embodiment, the peptide comprises the sequence KRWKKWFKKWKGGVIGVTFPF (SEQ ID NO:48), with one, two, three, four, or five substitutions, insertions, additions, or deletions, with the proviso that the amino acid sequence is not the sequence set forth in SEQ ID NO:2, 3, or 4. In one embodiment, the peptide comprises the sequence KRWKKWFKKWKGGVIGVTFPF (SEQ ID NO:48).

In another embodiment, the peptide comprises the sequence KRWKKWWKKWKGGVIGVTFPF (SEQ ID NO:49), with one, two, three, four, or five substitutions, insertions, additions, or deletions, with the proviso that the amino acid sequence is not the sequence set forth in SEQ ID NO:2, 3, or 4. In another embodiment, the peptide comprises the sequence KRWKKWWKKWKGGVIGVTFPF (SEQ ID NO:49).

In some embodiments, the peptide comprises the sequence RRWKRFFKRWKGGVIGVTFPF (SEQ ID NO:50), with one, two, three, four, or five substitutions, insertions, additions, or deletions, with the proviso that the amino acid sequence is not the sequence set forth in SEQ ID NO:2, 3, or 4. In some embodiments, the peptide comprises the sequence RRWKRFFKRWKGGVIGVTFPF (SEQ ID NO:50).

In one embodiment, the peptide of any one of SEQ ID NOs:44-56 is C-terminal amidated. In other embodiments, the peptides provided herein have a length of about 10 amino acids to about 50 amino acids. For example, in some embodiments, a peptide has a length of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids. In other embodiments, a peptide can have a length of, without limitation, about 10 to about 15 amino acids, about 15 to about 20 amino acids, about 20 to about 25 amino acids, about 25 to about 30 amino acids, about 30 to about 35 amino acids, about 35 to about 40 amino acids, about 40 to about 45 amino acids, about 45 to about 50 amino acids, about 10 to about 20 amino acids, about 20 to about 30 amino acids, about 30 to about 40 amino acids, or about 40 to about 50 amino acids.

In some embodiments, a C-terminal amide, or other C-terminal capping moiety can be present in peptides described herein. In one embodiment, a peptide as provided herein has a C-terminus that is amidated.

The term "amino acid" as used herein refers to natural amino acids, unnatural amino acids, and amino acid analogs, all in their various stereoisomers (e.g., D and L stereoisomers or other allostereomers if their structures so allow). Natural (or "naturally-occurring") amino acids include the 20 "standard" amino acids that are encoded by the codons of the universal genetic code (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine), as well as other "non-standard" amino acids that occur naturally but are not encoded by the codons of the universal genetic code (e.g., hydroxyproline, selenomethionine, and norleucine). Amino acids that are non-standard and/or non-naturally occurring include, without limitation, azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, 2,4-diaminoisobutyric acid, desmosine, 2,2'-diaminopimelic acid, 2,3-diaminopropionic acid, N-ethylglycine, N-ethylasparagine, hydroxylysine, allo-hydroxylysine, 3-hydroxyproline, 4-hydroxyproline, isodesmosine, allo-isoleucine, N-methylglycine, N-methylisoleucine, N-methylvaline, norvaline, norleucine, ornithine, and pipecolic acid.

An "analog" is a chemical compound that is structurally similar to another but differs slightly in composition (as in the replacement of one atom by an atom of a different element or in the presence of a particular functional group). An "amino acid analog" therefore is structurally similar to a naturally occurring amino acid molecule as is typically found in native peptides but differs in composition such that either the C-terminal carboxy group, the N-terminal amino group, or the side-chain functional group has been chemically modified or replaced with another functional group. Amino acid analogs include natural and unnatural amino acids that are chemically blocked, reversibly or irreversibly, or modified on their N-terminal amino group or their side-chain groups, and include, for example, methionine sulfoxide, methionine sulfone, S-(carboxymethyl)-cysteine, S-(carboxymethyl)-cysteine sulfoxide and S-(carboxymethyl)-cysteine sulfone. Amino acid analogs may be naturally occurring or can be synthetically prepared. Non-limiting examples of amino acid analogs include 5-Hydroxytrpophan (5-HTP), aspartic acid-(beta-methyl ester), an analog of aspartic acid; N-ethylglycine, an analog of glycine; and alanine carboxamide, an analog of alanine. Other examples of amino acids and amino acids analogs are listed in Gross and Meienhofer, The Peptides: Analysis, Synthesis, Biology, Academic Press, Inc., New York (1983).

The stereochemistry of a peptide can be described in terms of the topochemical arrangement of the side chains of the amino acid residues about the peptide backbone, which is defined by the peptide bonds between the amino acid residues and the I-carbon atoms of the bonded residues. In addition, peptide backbones have distinct termini and thus direction. The majority of naturally occurring amino acids are L-amino acids (including the 20 standard amino acids as well as a number of other naturally-occurring, non-standard amino acids), and naturally occurring, ribosomally-produced peptides are largely comprised of L-amino acids. D-amino acids are the enantiomers of L-amino acids. Assembling peptides out of D-amino acids, which are not recognized by proteases, can enable evasion from digestion and remain intact until reaching membranes (Wade et al., Proc Natl Acad Sci USA 87(12):4761-4765, 1990).

The peptides provided herein can be made up of L-amino acids, D-amino acids, or a combination thereof. For example, in some embodiments, a peptide can have an amino acid composition in which at least about 10% (e.g., at least about 10%, at least about 20%, at least about 25%, at least about 30%, at least about 40%, at least about 50%, at least about 60%, at least about 70%, at least about 75%, at least about 80%, at least about 85%, at least about 90%, at least about 95%) of the amino acids are D-amino acids. It is to be noted that some amino acid residues have more than one stereocenter, and the peptides provided herein can, in some embodiments, include diastereomers of these amino acids that differ from each other only in the configuration of one of their stereocenters.

In one embodiment, the peptide comprises one or more D-amino acid residues. In some embodiments, at least about 25 percent, illustratively, about 25 to 100 percent, about 50 to about 55 percent, and about 60 to about 75 percent of the amino acids in the peptide can be D-amino acids. In one embodiment, at least about 25 percent of the amino acids in the peptide can be D-amino acids. In another embodiment, 50 percent of the amino acids in the peptide can be D-amino acids. In one embodiment, at least about 75 percent of the amino acids in the peptide can be D-amino acids. In another embodiment, 100 percent of the amino acids in the peptide can be D-amino acids.

In some embodiments, peptidomimetic compounds can be used in place of the peptides provided herein. As used herein, the term "peptidomimetic" refers to compounds that are synthetic, non-peptide compounds having a three-dimensional conformation (a "peptide motif") that is substantially the same as the three-dimensional conformation of a selected peptide; a peptidomimetic compound therefore can essentially reproduce elements of amino acid structural properties and can confer the same or similar function as the selected peptide. As compared to a selected peptide, a peptidomimetic compound includes non-naturally occurring modifications, such as an altered backbone and/or non-natural amino acids. In some embodiments, for example, peptidomimetics can include beta-amino acids, peptoids, and/or N-methyl amino acids.

Peptidomimetic compounds can include amide ("peptide") or non-amide ("non-peptide") bonds in their backbone structure or can include a combination of peptide and non-peptide bonds in their backbone structure. Peptidomimetic compounds that are protease resistant or that have additional characteristics that enhance therapeutic utility, such as increased cell permeability and prolonged biological half-life, can be particularly useful. Such compounds typically have a backbone that is partially or completely non-peptide, but with side groups that are identical or similar to the side groups of the amino acid residues that occur in the peptide upon which the peptidomimetic compound is based. Several types of chemical bonds (e.g., ester, thioester, thioamide, retroamide, sulfonamide, reduced carbonyl, dimethylene and ketomethylene) can be useful substitutes for peptide bonds in the construction of peptidomimetic compounds. In some embodiments, the compounds provided herein include hybrids that contain one or more peptide portions and one or more peptidomimetic portions. Such hybrid peptides can incorporate a combination of natural amino acids and mimetic amino acids (e.g., standard amino acids and peptoids) in the same molecule.

The peptides provided herein can be obtained by any of a number of methods, including those known in the art. In some embodiments, a peptide can be obtained by extraction from a natural source (e.g., from isolated cells, tissues or bodily fluids), or can be produced by expression of a recombinant nucleic acid encoding the peptide, or by chemical synthesis (e.g., using solid phase peptide synthesis methods or a peptide synthesizer such as an ABI Peptide Synthesizer; Applied Biosystems; Foster City, Calif.). For example, standard recombinant technology using an expression vector encoding a peptide provided herein can be used. The resulting peptide then can be purified using, for example, affinity chromatographic techniques and HPLC. The extent of purification can be measured by any appropriate method, including but not limited to: column chromatography, polyacrylamide gel electrophoresis, or high-performance liquid chromatography. In some embodiments, a peptide can be designed or engineered to contain a tag sequence that allows the peptide to be purified (e.g., captured onto an affinity matrix). For example, a tag such as c-myc, hemagglutinin, polyhistidine, or FLAG™ tag (Kodak) can be used to aid peptide purification. Such tags can be inserted anywhere within the peptide, including at either the carboxyl or amino terminus. Other fusions that can be used include enzymes that aid in the detection of the peptide, such as alkaline phosphatase. In some embodiments, a peptide can be amidated at its carboxy terminus.

In some embodiments, a peptide provided herein can be isolated or purified. A "purified peptide" is a peptide that either has no naturally occurring counterpart (e.g., a peptidomimetic), or has been chemically synthesized and is thus uncontaminated by other peptides, or has been recombinantly produced and has been separated from components of the cell in which it was produced, or that has been separated or purified from other cellular components by which it is naturally accompanied (e.g., other cellular proteins, polynucleotides, or cellular components). Typically, a peptide is considered "purified" when it is at least 70%, by dry weight, free from the proteins and other molecules with which it naturally associates. A preparation of a purified peptide therefore can be, for example, at least about 80%, at least about 90%, or at least about 99%, by dry weight, the peptide. Suitable methods for purifying peptides can include, for example, affinity chromatography, immunoprecipitation, size exclusion chromatography, and ion exchange chromatography. The extent of purification can be measured by any appropriate method, including but not limited to: column chromatography, polyacrylamide gel electrophoresis, or high-performance liquid chromatography.

In one aspect, the present invention provides a polynucleotide encoding a peptide provided herein, or a nucleic acid molecule (e.g., expression vector, plasmid, etc.) comprising the polynucleotide encoding the peptide.

In other aspects, the activities of the peptides provided herein can be tested using any of a number of suitable methods, including those described in the Examples herein.

An activity of a peptide against bacteria, for example, can be tested by culturing the bacteria in a suitable liquid medium until cells reach a desired density (e.g., $OD_{600}$ of 0.8 to 1.1), and then diluting the cells to a suitable concentration in buffer containing varying concentrations of one or more selected peptides. Peptide concentrations used in the assays can range from 0 µg/ml to about 100 µg/ml with intermediate concentrations (e.g., about 0.01 µg/ml, about 0.05 µg/ml, about 0.1 µg/ml, about 0.5 µg/ml, about 1 µg/ml, about 2.5 µg/ml, about 5 µg/ml, about 7.5 µg/ml, about 10 µg/ml, about 25 µg/ml, about 50 µg/ml, 75 µg/ml, about 0.01 µg/ml to about 0.1 µg/ml, about 0.05 µg/ml to about 0.5 µg/ml, about 0.1 to about 1 µg/ml, about 0.5 µg/ml to about 5 µg/ml, about 2.5 µg/ml to about 10 µg/ml, or any other range between about 0.01 µg/ml and about 100 µg/ml) that vary for each peptide in order to maximize the number of data points. Assay cultures can be incubated for a desired length of time (e.g., about two hours), and serial dilutions of each sample can be prepared and plated. After a suitable length of incubation, colonies can be counted to determine the effectiveness of the peptide(s).

Bacterial survival at each peptide concentration can be calculated according to the ratio of the number of colonies on the plates corresponding to the peptide concentration and the average number of colonies observed for assay cultures lacking peptide. The peptide concentration required to kill about 50% of the viable cells in the assay cultures ($EC_{50}$) can be determined by plotting percent survival as a function of the log of peptide concentration (log µg/ml) and fitting the data to Equation (1) using, for example, GraphPad Prism (GraphPad Software, Inc., San Diego, Calif.), which describes a sigmoidal dose-response.

$$S = S_B + ((S_T - S_B)/(1 + 10^{(LogEC50-X)H})) \qquad (1)$$

In Equation (1), S is percent survival, $S_T$ and $S_B$ represent the upper and lower survival boundaries, X is the log of the peptide concentration, and H is the Hill slope of the transition region. Another form for Equation (1) is:

$$Y = \text{Bottom} + ((\text{Top}-\text{Bottom})/(1+10^{[(logEC50-X)*Hill\ Slope)]})) \qquad (1)$$

where Y corresponds to bacterial survival (in percentage) at a given peptide concentration (µg/ml), with X being the logarithm of that concentration. In the equation, "Top" and "Bottom" refer to the upper and lower boundaries and were constrained to values <100% and >0%, respectively.

The effect of a peptide on biofilm production can be assessed by, for example, incubating a biofilm-forming bacteria or other microbe with varying concentrations of one or more peptides for a certain length of time (e.g., 24 hours at 37° C.). Optical density of the cultures (e.g., at $OD_{600}$ nm) can be measured to assess microbial growth, and cultures then can be stained with crystal violet to assess biofilm production. See, e.g., Durham-Colleran et al., *Microb Ecol* 59(3):457-465, 2010.

An endotoxin neutralizing activity of a peptide can be assessed by, for example, the ability of the peptide to inhibit *E. coli* LPS in a rabbit pyrogenicity test or to increase the lethal dose 50 ($LD_{50}$) of *E. coli* LPS in mouse (e.g., CD1 mouse).

In other aspects, the peptides of the invention may be associated with one or more moieties. In some embodiments, the association is covalent. In other embodiments, the association is non-covalent. In one embodiment, the association is via a terminal (e.g., N-terminus, C-terminus, or both) linker (e.g., an amino acid linker such as e.g., Lys or Cys) or a chemical coupling agent. In another embodiment, the one or more moieties can be, e.g., a chemical tag, a solid material (e.g., nano- or micro-particles), a detectable label, a fusion partner (such as a chemical compound or a peptide), or a substrate e.g., a solid or semi-solid carrier, support or surface, including a bead (e.g. a microwell plate, nitrocellulose membrane, beads (e.g., latex, polystyrene)). In some embodiments, the association can be facilitated by a moiety that has a high affinity to a component attached to the substrate, e.g., the peptide can be associated with a biotin moiety, and the component associated with a surface can be avidin.

In other embodiments, the peptides of the invention are associated with (e.g., covalently or non-covalently attached to) a chemical tag or a solid material (e.g., nano- or micro-particles). In one embodiment, the chemical tag-peptide conjugate or particle-peptide conjugate can associate with membranes of microbial (e.g., bacterial) or tumor cells when brought in contact with a sample comprising the cells and form a complex, wherein the formation of the complex can be utilized to diagnose, image, isolate and/or determine microbial or tumor cells.

In some embodiments, the peptides of the invention may be conjugated to a detectable label (e.g., dye). In some embodiments, the detectable label is a fluorescent label (e.g., fluorescent dye, phosphorescent dye).

In one embodiment, the peptides of the invention may be associated with a molecule or reporter group that is masked such that it can be activated (i.e. unmasked), for example using light or a chemical agent.

In other embodiments, the peptides of the invention may be associated with a fusion partner that can be used to e.g., improve purification, to enhance expression of the peptide in a host cell, to aid in detection, to stabilize the peptide, and the like. Examples of suitable compounds for fusion partners include, but are not limited to, polyethylene glycol (PEG), Glutathione-S-transferase, and/or histidine tag.

In another aspect, the present invention provides a composition comprising a peptide, or a polynucleotide encoding the peptide, provided herein. In some embodiments, the peptides described herein may be formulated with pharmaceutically acceptable carriers or diluents as well as any other known adjuvants and excipients in accordance with conventional techniques such as those disclosed in e.g., Remington: The Science and Practice of Pharmacy, 19$^{th}$ Ed. (Easton, Pa.: Mack Publishing Company, 1995); Remington's Pharmaceutical Sciences, 18$^{th}$ Ed. (1990, Mack Publishing Co., Easton, Pa. 18042); Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999).

For example, peptides as provided herein can be formulated in compositions by admixture with one or more pharmaceutically acceptable, non-toxic excipients or carriers. Such compositions can be used to treat or prevent microbial infection, for example. In some embodiments, a composition can include one particular peptide, while in other embodiments a composition can include two or more different peptides (e.g., peptides having different sequences or different amounts of D- and L-amino acids). In some embodiments, the compositions provided herein can contain one or more peptides at a concentration of about 0.001 µg/ml to about 100 µg/ml (e.g., about 0.001 µg/ml to about 0.01 µg/ml, about 0.005 µg/ml to about 0.05 µg/ml, about 0.01 µg/ml to about 1 µg/ml, about 0.01 µg/ml to about 10 µg/ml, about 0.05 µg/ml to about 5 µg/ml, about 0.05 µg/ml to about 25 µg/ml, about 0.1 µg/ml to about 10 µg/ml, about 0.5 µg/ml to about 50 µg/ml, about 1 µg/ml to about 100 µg/ml, or about 10 µg/ml to about 100 µg/ml.

In some embodiments, the composition further comprises an excipient. Excipients (also referred to as pharmaceutically acceptable carriers) can be liquid or solid and can be selected with the planned manner of administration in mind so as to provide for the desired bulk, consistency, and other pertinent transport and chemical properties, when combined with one or more of peptides and any other components of a given composition. Common excipients include, without limitation, sterile water, saline, polyalkylene glycols such as polyethylene glycol, oils of vegetable origin, hydrogenated naphthalenes, binding agents (e.g., polyvinylpyrrolidone or hydroxypropyl methylcellulose), fillers (e.g., lactose and other sugars, gelatin, or calcium sulfate), lubricants (e.g., starch, polyethylene glycol, or sodium acetate), disintegrates (e.g., starch or sodium starch glycolate), and wetting agents (e.g., sodium lauryl sulfate). In some embodiments, biocompatible, biodegradable lactide polymer, lactide/glycolide copolymer, polyoxethylene-polyoxypropylene copolymers, or combinations thereof can be used as excipients for controlling the release of a peptide in vivo.

In other embodiments, a composition can include a peptide and one or more molecular crowding agents such as, by way of example and not limitation, FICOLL™ (e.g., FICOLL™ 70), polyethylene glycol (PEG), and dextran. FICOLL™ is a neutral, highly branched, high-mass, hydrophilic polysaccharide that dissolves readily in aqueous solutions. PEG is a polymer of ethylene oxide and is commercially available over a wide range of molecular weights from 300 g/mol to 10,000,000 g/mol. Dextran is a complex, branched polysaccharide made of glucose molecules. Without being bound by a particular mechanism, such agents may help to mimic the natural cellular environment, which may enhance the activity of the peptide. Such agents can be included in the compositions in amounts from about 5% to about 50% wt/vol (e.g., about 5%, about 10%, about 15%, about 20%, about 25%, about 30%, about 35%, about 40%, about 45%, or about 50% wt/vol, or any range there between, including about 5% to about 10%, about 10% to about 20%, about 20% to about 25%, about 25% to about 30%, about 30% to about 40%, or about 40% to about 50%).

In some embodiments, pharmaceutical formulations contemplated for use in the methods, articles, and kits of the invention may include about 0.01 to 1.0% (w/v), in certain embodiments about 0.05 to about 1.0%, of the peptide, about 0.02 to about 0.5% (w/v) of an acetate, phosphate, citrate or glutamate buffer allowing a pH of the final composition of from about 3.0 to about 7.0; about 1.0 to 10% (w/v) of a carbohydrate or polyhydric alcohol tonicifier and, optionally, about 0.005 to 1.0% (w/v) of a preservative selected from the group of m-cresol, benzyl alcohol, methyl, ethyl, propyl and butyl parabens and phenol. In another embodiment, such a preservative may be included if the formulated peptide is to be included in a multiple use product.

In still further embodiments, a pharmaceutical formulation of the present peptides may contain a range of concentrations of the peptide(s), e.g., between about 0.01% to about 98% w/w, or between about 1 to about 98% w/w, or preferably between 80% and 90% w/w, or preferably between about 0.01% to about 50% w/w, or more preferably between about 10% to about 25% w/w in these embodiments. A sufficient amount of water for injection may be used to obtain the desired concentration of solution.

In some embodiments, compositions can further include one or more other peptides, wherein each of the one or more other peptides has one or more biological activities (e.g., antimicrobial activity). In one embodiment, the one or more other peptides include, but are not limited to, one or more cathelicidins. Cathelicidins are known to one of ordinary skill in the art to refer to a large and diverse collection of cationic antimicrobial peptides, for example as described in U.S. Patent Publication No. 2012-0149631 A1, which is herein incorporated by reference in its entirety.

In one embodiment, compositions also can include one or more conventional antibiotics (e.g., amoxicillin, cephalexin, bacteriocin, neomycin, and/or polymyxin) and/or active ingredients from wound dressings or wound treatment compositions (e.g., NEOSPORIN®, bacitracin, and silver sulfadiazine).

Compositions can be prepared for topical (e.g., transdermal, sublingual, ophthalmic, or intranasal) administration, parenteral administration (e.g., by subcutaneous, intrathecal, intraventricular, intramuscular, or intraperitoneal injection, or by intravenous drip, in the form of liquid solutions or suspensions in aqueous physiological buffer solutions), for oral administration (e.g., in the form of tablets or capsules), or for intranasal administration (e.g., in the form of powders, nasal drops, or aerosols), depending on whether local or systemic treatment is desired and on the area to be treated. Administration can be rapid (e.g., by injection) or can occur over a period of time (e.g., by slow infusion or administration of slow release formulations). Compositions for other routes of administration also can be prepared as desired using appropriate methods. In addition, compositions can be prepared for in vitro use (e.g., for use on environmental surfaces or on medical devices).

Formulations for topical administration of peptides include, for example, sterile and non-sterile aqueous solutions, non-aqueous solutions in common solvents such as alcohols, or solutions in liquid or solid oil bases. Such solutions also can contain buffers, diluents and other suitable additives. Pharmaceutical compositions and formulations for topical administration can include transdermal patches, ointments, lotions, creams, gels, drops, suppositories, sprays, liquids, and powders. Nasal sprays also can be useful, and can be administered by, for example, a nebulizer, an inhaler, or another nasal spray device. Conventional pharmaceutical carriers, aqueous, powder or oily bases, thickeners and the like may be useful.

Compositions and formulations for oral administration include, for example, powders or granules, suspensions or solutions in water or non-aqueous media, capsules, sachets, or tablets. Such compositions also can incorporate thickeners, flavoring agents, diluents, emulsifiers, dispersing aids, or binders.

Compositions and formulations for parenteral, intrathecal or intraventricular administration can include sterile aqueous solutions, which also can contain buffers, diluents and other suitable additives (e.g., penetration enhancers, carrier compounds and other pharmaceutically acceptable carriers).

In other embodiments, the composition is a pharmaceutical composition.

In some embodiments, pharmaceutical compositions can include, but are not limited to, solutions, emulsions, aqueous suspensions, and liposome-containing formulations. These compositions can be generated from a variety of components that include, for example, preformed liquids, self-emulsifying solids and self-emulsifying semisolids. Emulsions are often biphasic systems comprising of two immiscible liquid phases intimately mixed and dispersed with each other; in general, emulsions are either of the water-in-oil (w/o) or oil-in-water (o/w) variety. Emulsion formulations can be useful for oral delivery of therapeutics due to their ease of formulation and efficacy of solubilization, absorption, and bioavailability.

Liposomes are vesicles that have a membrane formed from a lipophilic material and an aqueous interior that can contain the composition to be delivered. Liposomes can be particularly useful due to their specificity and the duration of action they offer from the standpoint of drug delivery. Liposome compositions can be formed, for example, from phosphatidylcholine, dimyristoyl phosphatidylcholine, dipalmitoyl phosphatidyl-choline, dimyristoyl phosphatidylglycerol, or dioleoyl phosphatidylethanolamine. Numerous lipophilic agents are commercially available, including LIPOFECTIN® (Invitrogen/Life Technologies, Carlsbad, Calif.) and EFFECTENE™ (Qiagen, Valencia, Calif.).

The peptides provided herein further encompass pharmaceutically acceptable salts, esters, or salts of such esters, or any other compound which, upon administration to an animal including a human, is capable of providing (directly or indirectly) the biologically active metabolite or residue thereof. Accordingly, for example, provided herein are pharmaceutically acceptable salts of peptides, prodrugs and pharmaceutically acceptable salts of such prodrugs, and other bioequivalents. The term "prodrug" indicates a therapeutic agent that is prepared in an inactive form and is converted to an active form (i.e., drug) within the body or cells thereof by the action of endogenous enzymes or other chemicals and/or conditions. The term "pharmaceutically acceptable salts" refers to physiologically and pharmaceutically acceptable salts of the peptides described herein (i.e., salts that retain the desired biological activity of the parent peptide without imparting undesired toxicological effects). Examples of pharmaceutically acceptable salts include, without limitation, salts formed with cations (e.g., sodium, potassium, calcium, or polyamines such as spermine), acid addition salts formed with inorganic acids (e.g., hydrochloric acid, hydrobromic acid, sulfuric acid, phosphoric acid, or nitric acid), and salts formed with organic acids (e.g., acetic acid, citric acid, oxalic acid, palmitic acid, or fumaric acid).

Compositions additionally can contain other adjunct components such as, for example, lubricants, preservatives, stabilizers, wetting agents, emulsifiers, salts for influencing osmotic pressure, buffers, colorings, flavorings, and aromatic substances. When added, however, such materials should not unduly interfere with the biological activities of the peptide components within the compositions provided herein. The formulations can be sterilized if desired.

Dosing of compositions for administration to a subject typically is dependent on the severity and responsiveness of the condition to be treated, with the course of treatment lasting, in some embodiments, from several days to several months, or in other embodiments until a cure is affected or a diminution of the condition is achieved. Persons of ordinary skill in the art routinely determine optimum dosages, dosing methodologies and repetition rates. Optimum dosages can vary depending on the relative potency of individual peptides and can generally be estimated based on $EC_{50}$ found to be effective in in vitro and in vivo animal models.

In some embodiments, dosage is about 0.01 µg to about 100 g per kg of body weight, and may be given once or more daily, biweekly, weekly, monthly, or even less often. Following successful treatment, it may be desirable to have the patient undergo maintenance therapy to prevent the recurrence of the disease state.

In some embodiments, a preliminary dosage for human infection can be inferred using guidelines put forth by the FDA (Guidance for Industry: Estimating the Maximum Safe Starting Dose in Initial Clinical Trials for Therapeutics in Adult Healthy Volunteers F.a.D. Administration, Editor. 2005 (Rockville, Md.), which is herein incorporated by reference in its entirety).

In one embodiment, dosage is at least about 0.01 mg per kg of body weight, illustratively, about 0.01 mg to about 100 mg per kg of body weight, about 0.05 mg to about 50 mg per kg of body weight, about 0.1 mg to about 10 mg per kg of body weight, about 0.4 mg to about 5 mg per kg of body weight, and may be given once or more daily, biweekly, weekly, monthly, or even less often.

In some embodiments, dosage is about 0.4 mg to about 5 mg per kg of body weight, and may be given once or more daily, biweekly, weekly, monthly, or even less often.

In other embodiments, a dose of at least about 0.01 µg is given, illustratively, about 0.01 µg to about 1 g, about 0.1 µg to about 0.1 g, about 1 µg to about 24 mg, and may be given once or more daily, biweekly, weekly, monthly, or even less often.

In other embodiments, treatments may differ if a subject is resistant or suspected of being resistant to certain antibiotics. For example, if a subject has an infection that is resistant to antibiotics, the dose may be increased, or the treatment may include two or more different peptides.

In other embodiments, one or more peptides can be admixed, encapsulated, conjugated or otherwise associated with other molecules, molecular structures, conventional antibiotics, or mixtures of compounds such as, for example, liposomes, polyethylene glycol, receptor targeted molecules, or oral, topical or other formulations, for assisting in uptake, distribution, absorption, or activity.

In still another aspect, the present invention provides an article of manufacture comprising a peptide as provided herein. In one embodiment, the article is a hygiene product (e.g., a personal hygiene product including but not limited to mouthwash and body wash). In another embodiment, the article is a wound dressing.

In some embodiments, the article is an invasive device, wherein the peptide is covalently or non-covalently attached onto a surface of the device. Covalent and non-covalent methods for attaching peptides to various surfaces are known in the art. In one embodiment, the device is a surgical tool. In another embodiment, the device is an implant. In other embodiments, the device is a catheter, a staple, a suture, an implant, or a tubing.

In still other aspects, the present invention provides a kit comprising a peptide provided herein or a polynucleotide encoding the peptide. In one embodiment, the kit further comprises instructions for using the components contained therein.

In another aspect, the present invention provides a method for treating infection by a microbial organism in a subject. The method comprises administering to the subject a peptide provided herein or a polynucleotide encoding the peptide. In one embodiment, the peptide comprises the amino acid sequence of Formula (I) (SEQ ID NO:1). In another embodiment, the peptide comprises the amino acid sequence of Formula (I) (SEQ ID NO:1) with one or more substitutions, insertions, additions, or deletions. In some embodiments, the peptide comprises the amino acid sequence of Formula (I) (SEQ ID NO:1) with one or more substitutions, insertions, additions, or deletions and with the proviso that the amino acid sequence is not the sequence set forth in SEQ ID NO:2, 3, or 4. In other embodiments, the peptide comprises the amino acid sequence of Formula (I) (SEQ ID NO:1) with the proviso that the amino acid sequence is not the sequence set forth in SEQ ID NO:2, 3, or 4. In one embodiment, the peptide comprises SEQ ID NO:5, 6, 7, 8, 9, 10, 11, 12, 13, 14, 15, 38, 39, 40, 41, 42, 43, 44, 45, 46, 47, 48, 49, or 50.

In some embodiments, the infection includes but is not limited to infections of the gastrointestinal tract, respiratory system, circulatory system, lymphatic system, urinary system, muscular system, skeletal system, nervous system, and reproductive system.

In another embodiment, a method for treating an infection by a microbial organism is provided, where the method includes contacting the microbial organism with a peptide or composition as provided herein. In other embodiments, after the contacting step, growth of the microbial organism can be reduced by at least about 5 percent, illustratively, about 5 percent to 100 percent, about 10 percent to about 99.99 percent, about 20 percent to about 95 percent, about 30 percent to about 80 percent, about 40 percent to about 70 percent, and about 50 to about 60 percent when measured in an assay to measure colony formation. In some embodiments, after the contacting, growth of the microbial organism can be reduced by at least about 50 percent when measured in an assay to measure colony formation directly or indirectly.

In other embodiments, the infection can be a polymicrobial infection.

In some embodiments, for example, a peptide or a composition comprising the peptide as described herein can be used to treat a subject having a microbial (e.g., bacterial or fungal) infection, such as in a wound that is in or on a subject (e.g., a mammal such as, without limitation, a human). Wounds can result from accidental occurrences, or can result from, for example, medical procedures.

In some embodiments, the subject can be a human who is a medical patient (e.g., a diabetes patient, or a patient in a hospital, clinic, or veterinary setting), a member of the armed services or law enforcement, a fire fighter, or a worker in the gas, oil, or chemical industry. In one embodiment, the subject is an animal suitable to be treated by a veterinarian including, but not limited to pets and livestock/farm animals.

In other aspects, the present invention provides a method for preventing, reducing or inhibiting growth of a microbial organism or biofilm on a surface. The method comprises contacting the surface with a composition comprising a peptide provided herein. In one embodiment, the peptide comprises the amino acid sequence of Formula (I) (SEQ ID NO:1). In another embodiment, the peptide comprises the amino acid sequence of Formula (I) (SEQ ID NO:1) with one or more substitutions, insertions, additions, or deletions. In some embodiments, the peptide comprises the amino acid sequence of Formula (I) (SEQ ID NO:1) with one or more substitutions, insertions, additions, or deletions and with the proviso that the amino acid sequence is not the sequence set forth in SEQ ID NO:2, 3, or 4. In other embodiments, the peptide comprises the amino acid sequence of Formula (I) (SEQ ID NO:1) with the proviso that the amino acid sequence is not the sequence set forth in SEQ ID NO:2, 3, or 4. In one embodiment, the peptide comprises SEQ ID NO:5, 6, 7, 8, 9, 10, 11, 12, 13, 14, 15, 38, 39, 40, 41, 42, 43, 44, 45, 46, 47, 48, 49, or 50.

In one embodiment, the surface is an environmental surface. In another embodiment, the surface is on a prosthetic or an implant. In other embodiments, the surface is in a living organism (e.g., a human or a non-human animal). In some embodiments, the peptides and compositions described herein are used in surface coatings for medical devices (e.g., catheters, prosthetics, implants, and other indwelling devices), or in dressings to be applied to a wound on or in a patient.

Biofilms are aggregates of microorganisms in which cells adhere to each other on a surface. Without wishing to be bound by any particular theory, it is believed that the adherent cells frequently are embedded in a self-produced matrix of extracellular polymeric substance (EPS) that generally is composed of extracellular DNA, proteins, and polysaccharides. Biofilms are ubiquitous, and can form on virtually any non-shedding, living or non-living surface in a non-sterile aqueous (or very humid) environment. Biofilms can be found, for example, in natural, industrial, hospital, and veterinary settings. Biofilms can be involved in a wide variety of microbial infections in the body, including common problems such as urinary tract infections, catheter infections, ear infections, formation of dental plaque, gingivitis, coating contact lenses, and less common but more serious conditions such as endocarditis, infections in cystic fibrosis, and infections of permanent indwelling devices such as joint prostheses and heart valves. Bacterial biofilms also can impair cutaneous wound healing and reduce topical antibacterial efficiency in healing or treating infected skin wounds.

Chronic opportunistic infections in immunocompromised patients and the aging population are a major challenge for medical professionals, as traditional antibiotic therapies usually are not sufficient to eradicate the infections. One reason for their persistence seems to be the capability of the bacteria to grow within biofilms that protect them from adverse environmental factors. *Pseudomonas aeruginosa* is an example of an opportunistic pathogen and a causative agent of emerging nosocomial infections. Other examples of microbes that can form medically relevant biofilms include, without limitation, *Streptococcus mutans* and *Streptococcus sanguinis*, which are involved in formation of dental plaque, *Legionella* bacteria, and *Neisseria gonorrhoeae*, which can form biofilms on human cervical epithelial cells.

In some embodiments, after the contacting, growth of the biofilm can be reduced by at least about 5 percent, compared to a control, when measured in an assay to measure optical density. In other embodiments, after the contacting, growth of the biofilm is reduced by at least about 25 percent, compared to a control when measured in an assay to measure optical density.

In other aspects, the present invention provides a method for promoting wound healing in a subject. The method comprises administering to the subject a peptide or a polynucleotide encoding the peptide. In one embodiment, the peptide comprises the amino acid sequence of Formula (I) (SEQ ID NO:1). In another embodiment, the peptide comprises the amino acid sequence of Formula (I) (SEQ ID NO:1) with one or more substitutions, insertions, additions, or deletions. In some embodiments, the peptide comprises the amino acid sequence of Formula (I) (SEQ ID NO:1) with one or more substitutions, insertions, additions, or deletions and with the proviso that the amino acid sequence is not the sequence set forth in SEQ ID NO:2, 3, or 4. In other embodiments, the peptide comprises the amino acid sequence of Formula (I) (SEQ ID NO:1) with the proviso that the amino acid sequence is not the sequence set forth in SEQ ID NO:2, 3, or 4. In one embodiment, the peptide comprises SEQ ID NO:5, 6, 7, 8, 9, 10, 11, 12, 13, 14, 15, 38, 39, 40, 41, 42, 43, 44, 45, 46, 47, 48, 49, or 50.

In some embodiments, the peptides and compositions described herein can be used in methods for promoting healing of wounds that are not infected (or that show no evidence of infection). For example, in some embodiments, a peptide or composition comprising one or more peptides described herein can be useful for treating an uninfected wound in a subject (e.g., a vertebrate such as a human), for example such that the wound has increased numbers of keratinocytes, shrinks in size more rapidly, and/or heals more quickly than it would without administration of the peptide or composition. In some embodiments, treatment of an uninfected wound with a peptide or composition can be considered effective if the wound size is reduced by at least about 5% (e.g., at least about 10%, at least about 20%, at least about 25%, at least about 30%, at least about 40%, at least about 50%, at least about 60%, at least about 70%, at least about 75%, at least about 80%, at least about 90%, or at least about 95%) during or after treatment, as compared to a control (e.g., a time point before or earlier in the treatment).

In one aspect, the peptides and compositions also can be used in methods that include determining whether a subject having a microbial infection is resistant to one or more conventional antibiotics (e.g., methicillin), or is suspected of being resistant to one or more conventional antibiotics. If the subject is determined to be resistant to the one or more conventional antibiotics or is suspected of being resistant to the one or more conventional antibiotics, the subject can be treated with a peptide or composition provided herein. In contrast, if the subject is determined not to be resistant to the one or more conventional antibiotics or is not suspected of being resistant to the one or more conventional antibiotics, the subject can be treated with the one or more conventional antibiotics. In such methods, the subject can be monitored to determine whether the treatment is effective, and the treatment can be adjusted accordingly. For example, if the subject is treated with one or more conventional antibiotics but is subsequently determined to be resistant to the conventional antibiotic(s), the subject can be treated with a peptide or composition as provided herein. In some embodiments, the subject can be treated with one or more AMPs and conventional antibiotics contemporaneously (e.g., in cases of severe infection insufficient time to try one or the other treatments).

In another aspect, the peptides and compositions provided herein can be used in methods for improving the effectiveness of treatment for microbial infection. For example, a method can include administering to a subject an amount of a peptide or composition that is sub-anti-microbial but is effective to reduce biofilm levels or inhibit biofilm formation or administering a peptide under conditions that are sub-anti-microbial but are effective to reduce biofilm levels or inhibit biofilm formation. For example, a peptide may be less effective as an anti-microbial agent under high salt conditions (e.g., about 125 to about 150 mM salt, including about 130 mM, about 135 mM, about 140 mM, or about 145 mM salt), but can retain effectiveness as an anti-biofilm agent under such conditions. After one or more sub-anti-microbial treatments, the subject can be treated with an anti-microbial amount of the peptide or composition, with the peptide under conditions that are anti-microbial, or with one or more conventional antibiotics. The sub-anti-microbial and anti-microbial treatments can be separated by any length of time, ranging from an hour or less to several hours to a day or more (e.g., about 0.5 hour, about one hour, about two hours, about three hours, about four hours, about six hours, about 12 hours, about 1 day, or more than 1 day). Treatments can be repeated as needed or desired.

The effectiveness of a peptide or composition containing one or more peptides as described herein can be determined by assessing microbial growth or biofilm growth before, during, and/or after treatment. In some embodiments, for example, samples can be obtained from a subject before treatment, and at one or more different time points during or after treatment with a peptide or composition as provided herein, and microbial growth can be measured by counting the number of colonies that grow up from the samples after they are plated on a solid medium or a method which is a quantitative indication of microbial growth Biofilm growth can be measured based on optical density (e.g., at 600 nm) and/or staining with crystal violet, for example. Treatment with a peptide or composition can be considered effective if microbial growth or biofilm formation is reduced by at least about 5% (e.g., at least about 10%, at least about 20%, at least about 25%, at least about 30%, at least about 40%, at least about 50%, at least about 60%, at least about 70%, at least about 75%, at least about 80%, at least about 90%, or at least about 95%) during or after treatment, as compared to a control (e.g., a time point before or earlier in the treatment).

Lipopolysaccharide (LPS) is a major structural component of the Gram-negative bacterial outer membrane and is believed to protect bacteria from antimicrobial compounds. LPS from *E. coli* and other Gram-negative bacteria is the endotoxin and, for example, may activate innate immunity through binding TLR4 receptors. Administration of parenteral products contaminated with pyrogens including LPS may lead to, for example, development of fever, induction of inflammatory response, shock, organ failure and death in humans or animals.

Also, the outer leaflet of outer membranes of Gram-positive bacteria contain a special lipid called lipoteichoic acid (LTA).

Without wishing to be bound by any particular theory, it is believed that the overall positive charge on certain antimicrobial peptides may assist them to form strong electrostatic interactions with the negatively charged LPS or other anionic lipids and anionic components e.g., in the membrane of Gram-negative bacteria neutralizing the overall negative charge. For example, the binding of such peptides with LPS of Gram-negative bacteria can have a major effect on the stability of bacterial membranes. Several cationic antimicrobial peptides including LL-37, SMAP-29, and CAP18 can bind LPS. Some antimicrobial peptides can reduce the host immune response to LPS by binding and sequestering it.

In one aspect, the present invention provides a method for treating or preventing endotoxemia in a subject. The method comprises administering to the subject an amount of a peptide effective to bind to an endotoxin so as to treat or prevent endotoxemia in the subject. In one embodiment, the peptide comprises the amino acid sequence of Formula (I) (SEQ ID NO:1). In another embodiment, the peptide comprises the amino acid sequence of Formula (I) (SEQ ID NO:1) with one or more substitutions, insertions, additions, or deletions. In some embodiments, the peptide comprises the amino acid sequence of Formula (I) (SEQ ID NO:1) with one or more substitutions, insertions, additions, or deletions and with the proviso that the amino acid sequence is not the sequence set forth in SEQ ID NO:2, 3, or 4. In other embodiments, the peptide comprises the amino acid sequence of Formula (I) (SEQ ID NO:1) with the proviso that the amino acid sequence is not the sequence set forth in SEQ ID NO:2, 3, or 4. In one embodiment, the peptide comprises SEQ ID NO:5, 6, 7, 8, 9, 10, 11, 12, 13, 14, 15, 38, 39, 40, 41, 42, 43, 44, 45, 46, 47, 48, 49, or 50.

In some embodiments, the endotoxemia is associated with endotoxin related shock including, but not limited to, septic shock, bacteremia-induced shock, and circulatory shock induced by endotoxin.

In other embodiments, the peptide binds to the endotoxin it encounters in the subject, thereby forming a conjugate that has reduced toxicity and pathogenicity relative to unconjugated endotoxin.

In one embodiment, the peptide binds to the endotoxin it encounters in the subject but does not cause bacterial lysis so as to prevent endotoxin-induced lethality.

In other embodiments, the peptide is covalently or non-covalently attached onto a surface of an invasive device, wherein the endotoxin contacts the peptide on the surface of the device during or following an invasive procedure carried out on the subject.

In one embodiment, the device is a surgical tool.

In another embodiment, the device is an implant.

In other embodiments, the device is a catheter, a staple, a suture, an implant, or a tubing.

In some embodiments, the endotoxin is an LPS of a Gram-negative bacterial strain.

In another embodiment, the bacterial strain is of the genus *Francisela, Acinetobacter, Pseudomonas, Klebsiella, Escherichia, Haemophilus, Proteus, Enterobacter, Serratia, Burkholderia, Stenotrophomonas, Alcaligenes, Mycobacterium, Legionella, Neisseria, Yersinia, Shigella, Vibrio,* or *Salmonella.*

In other embodiments, the bacterial strain is of the species *Francisela tularensis, Acinetobacter baumannii, Pseudomonas aeruginosa, Klebsiella pneumoniae, Klebsiella oxytoca, Escherichia coli, Haemophilus influenzae, Proteus mirabilis, Enterobacter species, Serratia marcescens, Burkholderia cepacia, Stenotrophomonas maltophilia, Alcaligenes xylosoxidans, Mycobacterium tuberculosis, Neisseria gonorrhoeae, Yersinia pestis, Shigella dysenteriae, Vibrio cholera,* or *Salmonella typhi.*

In one embodiment, the bacterial strain is of the species *Francisela tularensis, Francisela novicida, Francisela hispaniensis, Francisela noatunensis, Francisela philomiragia, Francisela halioticida, Francisela endociliophora, Francisela guangzhouensis,* or *Francisela piscicida.*

In another embodiment, the bacterial strain is of the species *Francisela tularensis.*

In some embodiments, the endotoxin is an LTA of a Gram-positive bacterial strain.

In other embodiments, the bacterial strain is of the genus *Staphylococcus, Bacillus, Rhodococcus, Actinobacteria, Lactobacillus, Actinomyces, Clostridium,* or *Streptococcus.*

In some embodiments, the bacterial strain is *Staphylococcus aureus, Bacillus anthracis, Streptococcus mutans* or *Streptococcus sanguinis.*

In other aspects, a device coated with a peptide is provided. In one embodiment, the peptide comprises the amino acid sequence of Formula (I) (SEQ ID NO:1). In another embodiment, the peptide comprises the amino acid sequence of Formula (I) (SEQ ID NO:1) with one or more substitutions, insertions, additions, or deletions. In some embodiments, the peptide comprises the amino acid sequence of Formula (I) (SEQ ID NO:1) with one or more substitutions, insertions, additions, or deletions and with the proviso that the amino acid sequence is not the sequence set forth in SEQ ID NO:2, 3, or 4. In other embodiments, the peptide comprises the amino acid sequence of Formula (I) (SEQ ID NO:1) with the proviso that the amino acid sequence is not the sequence set forth in SEQ ID NO:2, 3, or 4. In one embodiment, the peptide comprises SEQ ID NO:5, 6, 7, 8, 9, 10, 11, 12, 13, 14, 15, 38, 39, 40, 41, 42, 43, 44, 45, 46, 47, 48, 49, or 50.

In one embodiment, the device is a surgical tool.

In another embodiment, the device is an implant.

In other embodiments, the device is a catheter, a staple, a suture, an implant, or a tubing.

In another aspect, the present invention provides a method for determining an LPS or an LTA in a sample. The method comprises contacting the sample with a peptide under a condition such that the LPS or the LTS binds to the peptide to form a complex; and detecting the complex. In one embodiment, the peptide comprises the amino acid sequence of Formula (I) (SEQ ID NO:1). In another embodiment, the peptide comprises the amino acid sequence of Formula (I) (SEQ ID NO:1) with one or more substitutions, insertions, additions, or deletions. In some embodiments, the peptide comprises the amino acid sequence of Formula (I) (SEQ ID NO:1) with one or more substitutions, insertions, additions, or deletions and with the proviso that the amino acid sequence is not the sequence set forth in SEQ ID NO:2, 3, or 4. In other embodiments, the peptide comprises the amino acid sequence of Formula (I) (SEQ ID NO:1) with the proviso that the amino acid sequence is not the sequence set forth in SEQ ID NO:2, 3, or 4. In one embodiment, the peptide comprises SEQ ID NO:5, 6, 7, 8, 9, 10, 11, 12, 13, 14, 15, 38, 39, 40, 41, 42, 43, 44, 45, 46, 47, 48, 49, or 50.

In one embodiment, the sample is a biological fluid sample obtained from the subject.

In another embodiment, the sample comprises serum, urine, blood, tissue extract or sputum.

In some embodiments, the sample comprising the LPS or the LTA is transferred onto a suitable support under a condition permitting LPS or the LTA in the sample to attach to the support prior to contacting the sample with the peptide. In another embodiment, the peptide comprises a detectable label.

In some embodiments, the label comprises a fluorescent moiety, a radioactive moiety, or an enzyme.

In other aspects, the present invention provides a method for diagnosing an LPS- or LTA-associated disorder in a subject. The method comprises forming a complex between an LPS or an LTA and a peptide. In one embodiment, the peptide comprises the amino acid sequence of Formula (I) (SEQ ID NO:1). In another embodiment, the peptide comprises the amino acid sequence of Formula (I) (SEQ ID NO:1) with one or more substitutions, insertions, additions, or deletions. In some embodiments, the peptide comprises the amino acid sequence of Formula (I) (SEQ ID NO:1) with one or more substitutions, insertions, additions, or deletions and with the proviso that the amino acid sequence is not the sequence set forth in SEQ ID NO:2, 3, or 4. In other embodiments, the peptide comprises the amino acid sequence of Formula (I) (SEQ ID NO:1) with the proviso that the amino acid sequence is not the sequence set forth in SEQ ID NO:2, 3, or 4. In one embodiment, the peptide comprises SEQ ID NO:5, 6, 7, 8, 9, 10, 11, 12, 13, 14, 15, 38, 39, 40, 41, 42, 43, 44, 45, 46, 47, 48, 49, or 50.

In some embodiments, the endotoxin is an LPS of a Gram-negative bacterial strain.

In another embodiment, the bacterial strain is of the genus *Francisela, Acinetobacter, Pseudomonas, Klebsiella, Escherichia, Haemophilus, Proteus, Enterobacter, Serratia, Burkholderia, Stenotrophomonas, Alcaligenes, Mycobacterium, Legionella, Neisseria, Yersinia, Shigella, Vibrio,* or *Salmonella.*

In other embodiments, the bacterial strain is of the species *Francisela tularensis, Acinetobacter baumannii, Pseudomonas aeruginosa, Klebsiella pneumoniae, Klebsiella oxytoca, Escherichia coli, Haemophilus influenzae, Proteus mirabilis, Enterobacter species, Serratia marcescens, Burkholderia cepacia, Stenotrophomonas maltophilia, Alcaligenes xylosoxidans, Mycobacterium tuberculosis, Neisseria gonorrhoeae, Yersinia pestis, Shigella dysenteriae, Vibrio cholera,* or *Salmonella typhi.*

In one embodiment, the bacterial strain is of the species *Francisela tularensis, Francisela novicida, Francisela hispaniensis, Francisela noatunensis, Francisela philomiragia, Francisela halioticida, Francisela endociliophora, Francisela guangzhouensis,* or *Francisela piscicida.*

In another embodiment, the bacterial strain is *Francisela tularensis.*

In some embodiments, the endotoxin is an LTA of a Gram-positive bacterial strain.

In other embodiments, the bacterial strain is of the genus *Staphylococcus, Bacillus, Rhodococcus, Actinobacteria, Lactobacillus, Actinomyces, Clostridium,* or *Streptococcus.*

In some embodiments, the bacterial strain is *Staphylococcus aureus, Bacillus anthracis, Streptococcus mutans* or *Streptococcus sanguinis.*

In one embodiment, the LPS or the LTA is present in a sample obtained from the subject.

In another embodiment, the method further comprises obtaining a sample from the subject and detecting the complex in the sample.

In one embodiment, the sample is a biological fluid sample obtained from the subject.

In another embodiment, the sample comprises serum, urine, blood, tissue extract or sputum.

In some embodiments, the sample comprising the LPS or the LTA is transferred onto a suitable support under a condition permitting the LPS or the LTA in the sample to attach to the support prior to contacting the sample with the peptide.

In another embodiment, the peptide comprises a detectable label.

In some embodiments, the label comprises a fluorescent moiety, a radioactive moiety, or an enzyme.

In other aspects, the present invention provides a method for treating a composition comprising an LPS or an LTA. The method comprises contacting the composition with a peptide under a condition such that the LPS or the LTA binds to the peptide to form a complex; and separating the complex from the composition, thereby reducing or eliminating the LPS or the LTA from the composition. In one embodiment, the peptide comprises the amino acid sequence of Formula (I) (SEQ ID NO:1). In another embodiment, the peptide comprises the amino acid sequence of Formula (I) (SEQ ID NO:1) with one or more substitutions, insertions, additions, or deletions. In some embodiments, the peptide comprises the amino acid sequence of Formula (I) (SEQ ID NO:1) with one or more substitutions, insertions, additions, or deletions and with the proviso that the amino acid sequence is not the sequence set forth in SEQ ID NO:2, 3, or 4. In other embodiments, the peptide comprises the amino acid sequence of Formula (I) (SEQ ID NO:1) with the proviso that the amino acid sequence is not the sequence set forth in SEQ ID NO:2, 3, or 4. In one embodiment, the peptide comprises SEQ ID NO:5, 6, 7, 8, 9, 10, 11, 12, 13, 14, 15, 38, 39, 40, 41, 42, 43, 44, 45, 46, 47, 48, 49, or 50.

In one embodiment, the composition is for parenteral administration.

In another embodiment, the composition is for oral, intravenous, intramuscular, or subcutaneous administration.

In some embodiments, the composition is a cell culture reagent.

In other embodiments, the composition is blood, plasma, serum, or bone marrow.

In some embodiments, the endotoxin is an LPS of a Gram-negative bacterial strain.

In another embodiment, the bacterial strain is of the genus *Francisela, Acinetobacter, Pseudomonas, Klebsiella, Escherichia, Haemophilus, Proteus, Enterobacter, Serratia, Burkholderia, Stenotrophomonas, Alcaligenes, Mycobacterium, Legionella, Neisseria, Yersinia, Shigella, Vibrio,* or *Salmonella.*

In other embodiments, the bacterial strain is *Francisela tularensis, Acinetobacter baumannii, Pseudomonas aeruginosa, Klebsiella pneumoniae, Klebsiella oxytoca, Escherichia coli, Haemophilus influenzae, Proteus mirabilis, Enterobacter species, Serratia marcescens, Burkholderia cepacia, Stenotrophomonas maltophilia, Alcaligenes xylosoxidans, Mycobacterium tuberculosis, Neisseria gonorrhoeae, Yersinia pestis, Shigella dysenteriae, Vibrio cholera*, or *Salmonella typhi*.

In one embodiment, the bacterial strain is *Francisela tularensis, Francisela novicida, Francisela hispaniensis, Francisela noatunensis, Francisela philomiragia, Francisela halioticida, Francisela endociliophora, Francisela guangzhouensis*, or *Francisela piscicida.*

In another embodiment, the bacterial strain is *Francisela tularensis.*

In some embodiments, the endotoxin is an LTA of a Gram-positive bacterial strain.

In other embodiments, the bacterial strain is of the genus *Staphylococcus, Bacillus, Rhodococcus, Actinobacteria, Lactobacillus, Actinomyces, Clostridium*, or *Streptococcus.*

In some embodiments, the bacterial strain is *Staphylococcus aureus, Bacillus anthracis, Streptococcus mutans* or *Streptococcus sanguinis.*

The surface of cancer cell membranes can possess net negative-charge characteristics, whereas, normal animal cell membrane-surfaces can be largely neutral in charge characteristics. Accordingly, in other aspects, the present invention provides for anticancer therapeutics that are selectively toxic against cancerous cells while relatively less- or non-toxic against normal cells of a subject.

In one aspect, the present invention provides a method for treating or preventing a cancer in a subject in need thereof. The method comprises administering to the subject a therapeutically or prophylactically effective amount of a peptide provided herein, or a composition comprising the peptide or a polynucleotide encoding the peptide. In one embodiment, the peptide comprises the amino acid sequence of Formula (I) (SEQ ID NO:1). In another embodiment, the peptide comprises the amino acid sequence of Formula (I) (SEQ ID NO:1) with one or more substitutions, insertions, additions, or deletions. In some embodiments, the peptide comprises the amino acid sequence of Formula (I) (SEQ ID NO:1) with one or more substitutions, insertions, additions, or deletions and with the proviso that the amino acid sequence is not the sequence set forth in SEQ ID NO:2, 3, or 4. In other embodiments, the peptide comprises the amino acid sequence of Formula (I) (SEQ ID NO:1) with the proviso that the amino acid sequence is not the sequence set forth in SEQ ID NO:2, 3, or 4. In one embodiment, the peptide comprises SEQ ID NO:5, 6, 7, 8, 9, 10, 11, 12, 13, 14, 15, 38, 39, 40, 41, 42, 43, 44, 45, 46, 47, 48, 49, or 50.

As used herein, the term "treating" does not necessarily imply that a subject is treated until total recovery and includes, for example, the amelioration or management of one or more symptoms of the cancer. "Preventing" the cancer should not be taken to necessarily imply that cancer development is completely prevented and includes, without limitation, delay of the cancer development.

In one embodiment, the therapeutically effective amount is an amount sufficient to stop or slow the progression of the cancer. In another embodiment, the therapeutically effective amount is an amount sufficient to reduce the number of viable cancer cells in the subject. Methods for monitoring the proliferation of cancer cells and progress of cancer in a subject (e.g., tumor size, cell counts, biochemical markers, secondary indications, etc.) are known to one of ordinary skill in the art.

In some embodiments, the method for treating is used as a co-therapy such as, for example, administration in conjunction with radiation, surgery, or other chemotherapeutics. In other embodiments, the method includes administration of a therapeutically effective amount of the peptide in combination with an additional anti-cancer agent. A wide variety of anti-cancer (i.e., anti-neoplastic) agents are known in the art and include, for example alkylating agents, antimetabolites, natural antineoplastic agents, hormonal antineoplastic agents, angiogenesis inhibitors, differentiating reagents, RNA inhibitors, antibodies or immunotherapeutic agents, gene therapy agents, small molecule enzymatic inhibitors, biological response modifiers, and anti-metastatic agents.

In still further embodiments, the method for treating can be used an adjuvant therapy such as, for example, administering after surgery or other treatments (e.g., radiation, hormone therapy, or chemotherapy). Accordingly, in such embodiments, the method of adjuvant therapy encompasses administering following a primary or initial treatment, and either alone or in combination with one or more other adjuvant treatments, including, for example surgery, radiation therapy, or systemic therapy (e.g., chemotherapy, immunotherapy, hormone therapy, or biological response modifiers). In other embodiments, the method relates to neoadjuvant therapy, which is administered prior to a primary treatment.

Some non-limiting examples of cancer include carcinoma, melanoma, lymphoma, blastoma, sarcoma, germ cell tumors, and leukemia or lymphoid malignancies. Non-limiting examples of cancers that fall within these broad categories include squamous cell cancer (e.g., epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including lung cancer, gastrointestinal cancer, pancreatic cancer, glioblastoma, cervical cancer, ovarian cancer, liver cancer, bladder cancer, cancer of the urinary tract, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, melanoma, multiple myeloma and B-cell lymphoma, brain, as well as head and neck cancer, and associated metastases.

In other embodiments, cancer also encompasses cell proliferative disorders which are associated with some degree of abnormal cell proliferation and includes tumors, which include neoplasms or neoplastic cell growth and proliferation, whether malignant or benign, and all pre-cancerous and cancerous cells and tissues.

In one embodiment, the cancer is a lung cancer. In some embodiments, the lung cancer is an adenocarcinoma, a squamous cell carcinoma, a large cell carcinoma, a small cell lung cancer, an adenosquamous carcinoma, or a sarcomatoid carcinoma.

In other aspects, a peptide described herein can be used as a vehicle or carrier for the targeted delivery of other agents (e.g., antimicrobial or anticancer agents). Targeted delivery is described by e.g., U.S. Pat. No. 8,404,636 B2, which is incorporated herein by reference in its entirety.

In one aspect, the present invention provides a conjugate comprising a peptide conjugated to an agent, wherein the peptide is connected to the agent directly or through a linker segment, the agent being connected to the peptide or the linker segment through a stable or cleavable bond, wherein the conjugate carries and facilitates the delivery of the conjugated agent to a microbe or a cancer cell. In one embodiment, the peptide comprises the amino acid sequence of Formula (I) (SEQ ID NO:1). In another embodiment, the peptide comprises the amino acid sequence of Formula (I) (SEQ ID NO:1) with one or more substitutions, insertions, additions, or deletions. In some embodiments, the peptide comprises the amino acid sequence of Formula (I) (SEQ ID NO:1) with one or more substitutions, insertions, additions, or deletions and with the proviso that the amino acid sequence is not the sequence set forth in SEQ ID NO:2, 3, or 4. In other embodiments, the peptide comprises the amino acid sequence of Formula (I) (SEQ ID NO:1) with the proviso that the amino acid sequence is not the sequence set forth in SEQ ID NO:2, 3, or 4. In one embodiment, the peptide comprises SEQ ID NO:5, 6, 7, 8, 9, 10, 11, 12, 13, 14, 15, 38, 39, 40, 41, 42, 43, 44, 45, 46, 47, 48, 49, or 50.

In some embodiments, the peptide is amidated at the C-terminus.

In other embodiments, the linker segment affixes the agent to the peptide through acylation of the amino group of the N-terminus of the peptide.

The agent may be any compound desired to be delivered to a cell. Such compounds include, but are not limited to, those which may provide a therapeutic or diagnostic benefit. In some embodiments, the compounds are nucleic acids, peptide nucleic acids, polypeptides (including for example, fusion proteins), carbohydrates, peptidomimetics, small molecule inhibitors, chemotherapeutic drugs, anti-inflammatory drugs, antibodies, single chain Fv fragments (SCFV), lipids, proteoglycans, glycolipids, lipoprotein, glycomimetics, natural products, or fusion proteins.

In one embodiment, the agent is an antimicrobial agent.

In some embodiments, the antimicrobial agent is levofloxacin, chloramphenicol, or a diazeniumdiolate.

In other embodiments, the agent is an anticancer agent.

In one embodiment, the anticancer agent is an alkylating agent, an antimetabolite, a natural antineoplastic agent, a hormonal antineoplastic agent, an angiogenesis inhibitor, a differentiating reagent, a RNA inhibitor, an antibody or immunotherapeutic agent, a gene therapy agent, a small molecule enzymatic inhibitor, a biological response modifier, or an anti-metastatic agent.

In some embodiments, the peptide and the agent to be delivered to a cell are connected to each other to allow the peptide to carry the compound across a cell membrane into a cell. Forms of attachment are known in the art and include, without limitation, bonding, fusion or association between the carrier peptide and the at least one compound (for example, but not limited to, covalent bonding, ionic bonding, hydrogen bonding, aromatic stacking interactions, amide bonds, disulfide bonding, chelation). In some embodiment, the carrier peptide and the agent may be connected in an irreversible or a reversible manner, such that upon entry into a cell the agent is released from the carrier peptide.

In other embodiments, the agent is connected to the carrier peptide at its N-terminus, its C-terminus or at any other location. In one embodiment, the agent is connected to the peptide at its N-terminus. In another embodiment, the agent is connected to the peptide at its C-terminus. In other embodiments, the agent is connected to the peptide via a linker molecule in some embodiment, the linker molecule is a peptide linker.

In other aspects, the invention provides a method for targeting delivery of the agent to a cell, the method comprising administering to a subject a therapeutically or prophylactically amount of a conjugate described herein.

In one embodiment, the cell is a bacterial cell, a fungal cell, or a cancer cell.

In another embodiment, the cells are cancer cells; and the invention provides a method for targeting delivery of the agent to cancer cells, for example in a mixed population of cancer and non-cancer cells. In some embodiments, the targeting delivery provides higher selectivity against and killing of cancer cells over normal cells.

The peptides and/or conjugates (or nucleic acids or vectors encoding same) described herein may be delivered to a cell by a number of different methods known to one of ordinary skill in the art including, but not limited to, in vitro, ex vivo, and/or in vivo methods for delivery.

In another embodiment, a method for targeting delivery of the invention comprises administering the conjugate and/or peptide (or nucleic acids or vectors encoding same) to a subject.

In one embodiment, an in vitro method may comprise bringing the conjugate and/or peptide (or nucleic acids or vectors encoding same) into contact with one or more cells or a composition comprising one or more cells or proteins of interest; for example, contacting the conjugate or peptide (or nucleic acids or vectors encoding same) with a sample, composition or media in which the one or more cells (or proteins of interest in certain embodiments) are contained (such as mixing a composition of the invention with a liquid sample containing one or more cells or proteins).

In another embodiment, an ex vivo method may comprise bringing the conjugate and/or peptide (or nucleic acids or vectors encoding same) into contact with one or more cells or a composition comprising one or more cells or proteins of interest under a condition that takes place outside the subject. For example, in some embodiments, treatment of immune cells ex vivo are performed by exposing such cells to the conjugate and/or peptide in an artificial environment (sterile conditions) outside the subject with the minimum alteration of the natural conditions. In one embodiment, this procedure can involve culturing mononuclear cells that have been isolated from the subject prior to administration back into the same subject. In some embodiments, the targeting delivery ex vivo provides higher selectivity against and killing of cancer cells over normal cells that may be administered back into the subject.

In other aspects, the invention provides a method for delivering the agent to a cell as well as a method for increasing the transferability across cell membrane of the agent to be delivered to the cell, by connecting the agent of interest to a peptide of the invention. In some embodiments, the peptides described herein may be used as carriers to transport agents across a cell membrane into the cell.

In some embodiments, the method provides forming transient pores in the membrane through which the agent enters the cell.

In one embodiment, the peptide comprises the amino acid sequence of Formula (I) (SEQ ID NO:1). In another embodiment, the peptide comprises the amino acid sequence of Formula (I) (SEQ ID NO:1) with one or more substitutions, insertions, additions, or deletions. In some embodiments, the peptide comprises the amino acid sequence of Formula (I) (SEQ ID NO:1) with one or more substitutions, insertions, additions, or deletions and with the proviso that the amino acid sequence is not the sequence set forth in SEQ ID NO:2, 3, or 4. In other embodiments, the peptide comprises the amino acid sequence of Formula (I) (SEQ ID NO:1) with the proviso that the amino acid sequence is not the sequence set forth in SEQ ID NO:2, 3, or 4. In one embodiment, the peptide comprises SEQ ID NO:5, 6, 7, 8, 9, 10, 11, 12, 13, 14, 15, 38, 39, 40, 41, 42, 43, 44, 45, 46, 47, 48, 49, or 50.

In some embodiments, the cell is a eukaryotic cell.

In another embodiment, the cell is a bacterial, a fungal or a cancer cell.

In some embodiments, the cell is present in a subject and the method comprises administering the peptide/agent conjugate/complex to the subject.

In other embodiments, the cell is ex vivo and the method comprises contacting the cell with the peptide/agent conjugate/complex.

The invention will be further described in the following examples, which do not limit the scope of the invention described in the claims.

EXAMPLES

Example 1

Materials and Methods

Bacterial Strains. Bacterial strains (Table 1) were obtained from American Type Culture Collection (ATCC, Manassas, Va.). The bacteria were first grown in the respective recommended media and then selected over cation adjusted Mueller Hinton Broth (MHBII, BD 212322) agar (supplemented with antibiotics for antibiotic-resistant strains) and then grown in MHBII (supplemented with antibiotics for antibiotic-resistant strains). Bacteria were then aliquoted and stored frozen as 20% glycerol stocks at −80° C.

Peptides. Peptides were procured from several vendors: Anaspec, Inc (Fermont, Calif.), ChinaPeptides, Inc (Shanghai, China) and Virongee (USA). All the peptides were at >95% purity according to the manufacturers' reports.

Reagents and Buffers. Three kinds of phosphate buffers were used such as 10 mM Sodium phosphate (Na—$PO_4$), Phosphate Buffered Saline (PBS) without calcium or magnesium and Dulbecco's Phosphate Buffered Saline (DPBS) with calcium and magnesium. All the phosphate buffers were adjusted to pH=7.4 and sterilized by filtration through 0.22 μm PVDF membrane. Resazurin sodium salt, Nitrocefin, ortho-Nitrophenyl-β-galactoside (ONPG), all the inorganic salts along with Hexadecyltrimethylammonium bromide (HCMAB), Lipopolysaccharides from *Escherichia coli* 0111:B4, Lipo-teichoic acid (LTA) from *Staphylococcus aureus*, Polymyxin B (PMB), (Greiner Bio-one) polypropylene 96 well plates were purchased from Sigma.

Instrumentation and Software. Gemini EM (Molecular Devices) fluorescence plate reader was used to conduct all the fluorescence reading. Absorbances were measured in (BioTek) Eon. Circular Dichroism studies were conducted using Jasco J-1500 spectropolarimeter (Jasco, Easton, Md.). Data were pre-analyzed with Excel software before plotting and results were generated using Graphpad Prism 5 (GraphPad Software, Inc.).

Bio Informatics. ATRA1 and WG12 sequences were manually aligned. Secondary structures of the ATRA1 variants and NA-CATH derived sequences were predicted by I-TASSER (Iterative Threading ASSEmbly Refinement) using the deposited NMR structures of crotalicidin as template-sequence. The resulting co-ordinate files (in .pdb format) were visualized by the programs such as Chimera and Pymol (The PyMOL Molecular Graphics System, Version 2.0 Schrödinger, LLC).

Co-ordinates of LPS were obtained from pdb accession code 1QFG and for ATRA1, the predicted structure were used.

Endotoxin Binding. The binding of endotoxin (LPS/LTA) was evaluated using a fluorogenic conjugateBODIPY TR-Cadaverine (BC). BC binds endotoxin loses its fluorescence. The peptide competitively displaces BC from endotoxin and the fluorescence is reestablished. Competitive inhibition of endotoxin-BC binding was utilized due to presence of peptides already in complexion with endotoxin. 25 μL of 20 μM of peptides in 10 mM Na—$PO_4$ buffer were incubated with 25 μL of LPS (40 μg/mL) or LTA (40 μg/mL) for 15 min and then added with 50 μL of BC (20 uM). Peptides bind to LPS or LTA and competitively prevents BC bind to the endotoxin. BC loses its fluorescence on binding to endotoxin. The fluorescence intensity of the unbound BC was measured at excitation=580 nm and emission=620 nm.

Circular Dichroism (CD). CD was performed by allowing the samples were allowed to equilibrate for 5 min at 25° C. in a 1 mm path length quartz cuvette (Jasco) prior to collecting the spectra. Scans were performed from 200 to 250 nm at 0.2 nm intervals, with a data integration time of 4 s and 1 nm bandwidth. Each test was performed once, and mean residue ellipticity (MRE), [θ], was calculated from the average of four scans. Equation 1:

$$[\theta](deg \cdot cm^2 \cdot dmol^{-1}) = \frac{Ellipticity(mdeg) \cdot 10^6}{Pathlength(mm) \cdot [Peptide](\mu M) \cdot (n-1)}$$

where, n=number of residues in the peptide.

The peptides were analyzed at a concentration of 30 μM in 10 mM Na-$PO_4$, 50% (v/v) trifluoroethanol (TFE) in 10 mM Na-$PO_4$, 17.6 mM sodium dodecyl sulfate (SDS) in Na—$PO_4$ buffer. Some of the peptides were also analyzed in presence of LPS micelles in both 10 mM Na—$PO_4$ and DPBS at a peptide: lipid ratio of 1:4.2.

Tryptophan Fluorescence Studies. The binding interactions of the peptides with LPS were determined by using the intrinsic fluorescence of Trp at excitation wavelength of 280 nm and emission in the range of 300-400 nm (Trp Blue Shift). 5 μM of peptides, which contained Trp, were titrated with increasing concentrations of LPS (0-20 μM). A standard single-site binding curve fitted to equation (1) was used to calculate the binding constants (equilibrium dissociation constant, $K_D$).

$$f = B_{max} * L * (K_D + L)^{-1} \qquad \text{Equation 2:}$$

where, f=fractional saturation of the peptide with respect to LPS expressed in terms of difference in wavelength, $\Delta\lambda_{max} = \lambda_{max} - \lambda(0)_{max}$, $\lambda_{max}$=emission maxima of the peptide on successive addition of LPS in nm, $\lambda(0)_{max}$=emission maxima of the peptide without addition of LPS in nm, L=ligand (LPS) concentration (μM), and $K_D$=equilibrium dissociation constant (μM).

The fluorescence of Trp was quenched by addition of acrylamide (0-0.2 M) to peptides (10 μM) in both free and in LPS (25 μM) bound states in DPBS. Stern-Volmer's constant ($K_{sv}$) was calculated using equation (2), where $F_0$=fluorescence intensity in the absence of a quencher, F=fluorescence intensity in the presence of a quencher at each titration, and [Q]=concentration of quencher in molarity.

$$F_0/F = 1 + K_{sv}[Q] \qquad \text{Equation 3:}$$

Antimicrobial Studies. The phosphate buffers used for antimicrobial assays were supplemented with non-nitrogenous energy source, 0.1% (w/v) glucose. To conduct antimicrobial assays, bacterial strains were first suspended in respective buffers. E. coli (ATCC 25922) and B. cereus (ATCC 11778) were grown in MHB II up to $OD_{600\ nm}$~1 and stored as frozen stock in 20% glycerol at −80° C. Occasionally they were thawed and enumerated by serial dilution and spreading on MHB II agar plates. The concentrations of the frozen stocks of E. coli and B. cereus strains were 1.0-1.1*$10^8$ CFU/mL with $OD_{600\ nm}$~0.8. In case of other bacterial strains, they were grown on the days of experiment up to $OD_{600\ nm}$~1-1.5 and then adjusted to $OD_{600\ nm}$~0.8. The growth media of the drug-resistant bacterial strains were supplemented with few of the respective antibiotics against which they are resistant. 200 µL of the 0.8 $OD_{600\ nm}$ culture were added to 10 mL of the respective buffer to obtain a suspension which was used to incubate with equal volumes of peptide solution in the same buffer. The bacterial strain and the media conditions used to culture the bacteria for antimicrobial testing are shown in Table 1.

TABLE 1

List of Microbial Strains and growth conditions
(X = no supplementation)

| Bacteria | Strain (ATCC ID) | Growth Media | Supplements | Temp. (° C.) |
|---|---|---|---|---|
| Escherichia coli | 25922 | MHB-II | X | 35 |
| Escherichia coli | 51659 | MHB-II | 50 µg/mL of each of Streptomycin and Tetracycline | 37 |
| Bacillus cereus | 11778 | MHB-II | X | 30 |
| Staphylococcus aureus | BAA-1718 | MHB-II | X | 37 |
| Acinetobacter baumannii | 9955 | MHB-II | X | 37 |
| Acinetobacter baumannii | BAA-1795 | MHB-II | 10 µg/mL of each of Ampicillin, Ceftazidime, Gentamycin, Norfloxacin, and 1 µg/mL of Levofloxacin | 37 |
| Klebsiella pneumoniae | 33495 | MHB-II | X | 37 |
| Klebsiella pneumoniae | BAA-1705 | MHB-II | 10 µg/mL of each of Ampicillin, Ceftazidime, and Levofloxacin | 37 |
| Pseudomonas aeruginosa | 9027 | MHB-II | X | 37 |
| Candida albicans | MYA-2876 | YM broth | X | 37 |

Antimicrobial assays in different phosphate buffers and serum were conducted by adapting, with necessary modifications a fast high-throughput method based on Virtual Colony Count technique and later modified by incorporating the use of resazurin. At first serial dilution of a microbial strain in respective buffer was poured in the wells of 96 well polypropylene microplate and was then added with same volume of 2× MHB II supplemented with 80 µg/mL resazurin and incubated at 35° C. in a Gemini EM Microplate Reader (Molecular Devices) overnight with intermittent shaking. As the microbe grows it reduces non-fluorescent resazurin to fluorescent resorufin and the fluorescent intensity of each well were measured (excitation=570 nm, emission=590 nm) each 5 min for 15 hours. The time (t, min) to reach a certain fluorescence (RFU=20000 with respect to the starting fluorescence) was correlated with the initial bacterial concentration (in CFU/mL) in the particular well to obtain a calibration plot of the form:

$$\text{Log}([Bacteria], CFU/mL) = b + m*t \quad \text{Equation 4:}$$

where b and m are the intercept and the slope of the correlation dependent on the specific bacterial strain and the buffer used.

To obtain antimicrobial efficacy of the peptides, 50 µL of serially diluted peptide in a buffer was incubated with 50 µL microbial suspension in the same buffer for 3 hours in black polypropylene 96 well plate. After incubation the wells were added with 100 µL of 2× MHB II supplemented with 80 µg/mL resazurin and then incubated with continuous fluorescence reading for overnight time period as described earlier. The surviving microbial population (CFU/mL) in each well were calculated by first finding the time to reach a fluorescence of RFU=20000 and the correlation (4) for the specific microbial strain and buffer. % Survival represents the proportion of viable cells in peptide treated cells relative to cells treated with the respective buffer alone. Equation 5:

$$(\% \text{ Microbial survival})_{[peptide]} = \frac{\text{Surviving population after incubation with the [peptide]}}{\text{Surviving population after incubation with no [peptide]}} * 100$$

Finally, the antimicrobial effectiveness of each peptide against the particular microbial strain in the specific buffer was determined by plotting % microbial survival as a function of the log of the concentration of the peptide and fitting the resulting data to a variable-slope sigmoidal regression model (equation 6). In this equation, $\log(EC_{50})$ represents the log of the concentration of the peptide required to kill half of the microbial population, where $S_{min}$ and $S_{max}$ correspond to the minimal and maximal microbial survival values (respectively), and H, Hill slope, is the parameter defining the steepness of the transition slopes of sigmoidal survival curves.

$$\% \text{ Microbial survival} = S_{min} + (S_{max} - S_{min})/(1 + 10^{\log(EC_{50}) - \log[peptide]*H}) \quad \text{Equation 6:}$$

Interactions with Bacterial Membranes. Interaction of the peptides with bacterial membranes in different phosphate buffers were evaluated using E. coli ML35p, constructed in our laboratory. At first, competent cells of E. coli ML35 were produced by conventional competent cell preparation method, then transformed with pBR322 plasmid. Transformed colonies were selected after growing on Luria-agar containing 50 µg/mL ampicillin. A single transformed colony was grown in presence of ampicillin first in Luria broth and then in MHBII and stored as 20% glycerol stock at −80° C. This frozen stock, on the day of the experiment, was thawed and grown in MHBII containing ampicillin up to $OD_{600\ nm}$=0.8-0.9, washed with PBS and then suspended in the respective buffer up to the required $OD_{600\ nm}$ for use.

NPN Assay. The outer membrane perturbation of bacteria was evaluated by incubating E. coli ML35p with peptides in presence of NPN. 100 mM NPN in acetone was supplemented proportionately to a bacterial suspension of $OD_{600\ nm}$~0.5 to achieve a final concentration of 20 µM of NPN and the mixture was equilibrated for 30 mins. Then, 90 µL of the bacterial suspension containing 20 µM NPN was added with 10 µL of 250 µM peptide (10×) solution in water and scanned for fluorescence intensity (excitation=350 nm, emission=420 nm). The % Perturbation was calculated by considering PMB to be causing 100% Perturbation and water (without peptide) as 0% Perturbation. Each peptide was tested in triplicate in each of the three phosphate buffers used.

Membrane Disruptions. The outer and the inner membrane disruptions by the peptides were evaluated by incubating bacterial suspension with peptides and then measuring the activity of enzymes leaked out of the cells. 100 µL of 10× concentration of peptide in water was incubated with 900 µL bacterial suspension ($OD_{600\,nm}$~0.1) in respective buffer for 3 hours at room temperature with gentle rotation. Then the cells and debris were separated by centrifugation (10000 r.p.m. for 30 mins) and the supernatant was collected and tested for activity of enzymes that had leaked out of the bacterial cells. HCMAB was used as a positive control to cause 100% membrane disruption and water as a negative causing 0% disruption.

The outer membrane disruption was tested by using the activity of beta-lactamase present in the periplasmic space of *E. coli* ML35p. Peptides when disrupt the outer membrane enough to cause beta-lactamase to come out, the degree of disruption can be measured by the virtue of the kinetics of the enzyme and using a chromogenic cephalosporin substrate called nitrocefin. β-lactamase mediated hydrolyzed product of nitrocefin has an absorbance $\alpha_{max}$=486 nm. Supernatant collected from the incubation of peptide with bacteria was added with nitrocefin solution in DPBS and incubated at 35° C. and continuous absorbance readings. The slope of the linear section of the absorbance curve (absorbance vs time), was used as a measure of membrane disruption and the % Disruption was calculated as: Equation 7:

$$\% \text{ Outer-Membrane Disruption} = \frac{\text{Slope for Nitrocefin hydrolysis for the test peptide}}{\text{Slope for Nitrocefin hydrolysis for } HCMAB} * 100$$

The inner membrane disruption was tested by using the activity of β-galactosidase present in the periplasmic space of *E. coli* ML35p, which lacks lactose-permease. Peptides when disrupt the inner membrane enough to cause β-galactosidase to come out, the degree of disruption can be measured by the virtue of the kinetics of the enzyme and using a substrate called ortho-Nitrophenyl-β-galactoside (ONPG). β-galactosidase mediated hydrolyzed product of ONPG has an absorbance λmax=420 nm. Supernatant collected from the incubation of peptide with bacteria was added with ONPG solution in DPBS and incubated at 35° C. and continuous absorbance readings. The slope of the linear section of the absorbance curve (absorbance vs time), was used as a measure of membrane disruption and the % Disruption was calculated as: Equation 8:

$$\% \text{ Inner-Membrane Disruption} = \frac{\text{Slope for } ONPG \text{ hydrolysis for the test peptide}}{\text{Slope for } ONPG \text{ hydrolysis for } HCMAB} * 100\%$$

Hemolysis. To measure the in-vitro hemolysis activity of the peptides, sheep blood was suspended in DPBS and washed with two times with same buffer and finally diluted to 20% suspension. Peptides were incubated at 125 µM against 10% suspension of sheep blood cells in DPBS for 1 hour at 37° C. where DPBS alone served as negative control and 1% TritonX-100 served as 100% lysis. After incubation, the cells were pelleted by centrifugation (1000 r.p.m, 5 min) and the supernatant was transferred to a microplate and read at 540 nm absorbance. Each peptide was tested in triplicate. % Hemolysis was expressed as: Equation 9:

$$\% \text{ Hemolysis} = \frac{(\text{Absorbance})_{peptide} - (\text{Absorbance})_{no\text{-}peptide}}{(\text{Absorbance})_{TritonX\text{-}100} - (\text{Absorbance})_{no\text{-}peptide}} * 100\%$$

Cytotoxicity. Cells were seeded in complete growth medium (Minimal Essential Medium, MEMα, supplemented with 10% Fetal Bovine Serum) into a culture-treated 96-well plate at a density of 25000 cells per well. After 24 hours, culture media was aspirated and replaced with media containing the selected peptide. No-serum experiments were conducted in Opti-MEM I reduced serum media (ThermoFisher, 31985062) and 10% serum experiments were performed in complete growth medium. In all cases, DBPS was used as a vehicle only control and buffer to serially dilute the peptides. After exposure to the peptides or vehicle-alone for the defined period, Alamar blue dye (resazurin) was added directly to the media and allowed to incubate for two hours. Following incubation, A570/A600 measurements were made to calculate reduction of resazurin dye to resorufin. A ratio of reduction in treated versus untreated cells was calculated in order to determine overall cell viability. The human cells were always maintained in a 37° C. incubator under 5% $CO_2$.

Example 2

Peptide Design and Properties

Sequence, Hydrophobic Moment and Wimley-White Transfer Energies. Table 2 shows primary sequences of the peptides, their molecular weights, Total Hydrophobic Moment and Free Energy of Transfer to phosphatidylcholine membrane interfaces. Putative helix-forming sequences are bold-faced. The moments and the free energies were calculated using MPEx by presetting % α-helix=64%, N-terminal protonated, C-terminal amidated for every peptide and are plotted in FIG. 1.

TABLE 2

Sequences and physio-chemical properties of peptides

| | | | Calculated | |
|---|---|---|---|---|
| Peptide | C-terminal amidated sequence Sequence | MW (g/mol) | Wimley-White Total Hydrophobic Moment | Wimley-White Transfer free energies (kcal/mol) |
| ATRA1 | KRFKKFFKKLK (SEQ ID NO: 2) | 1496.9 | 6.49 | -2.19 |
| ATRA1-A | KRAKKFFKKLK (SEQ ID NO: 4) | 1420.8 | 5.23 | -0.89 |
| ATRA1-AK | KKAKKFFKKLK (SEQ ID NO: 5) | 1392.8 | 5.21 | -0.71 |

TABLE 2-continued

Sequences and physio-chemical properties of peptides

| Peptide | C-terminal amidated sequence | Calculated | | |
|---|---|---|---|---|
| | | MW (g/mol) | Wimley-White Total Hydrophobic Moment | Wimley-White Transfer free energies (kcal/mol) |
| ATRA1-AR | KRAKKFFKRLK (SEQ ID NO: 6) | 1448.9 | 5.18 | -1.07 |
| ATRA1-AR2 | KRAKRFFKRLK (SEQ ID NO: 7) | 1476.9 | 5.04 | -1.25 |
| ATRA1-AR3 | RRAKRFFKRLK (SEQ ID NO: 8) | 1504.9 | 4.86 | -1.43 |
| ATRA1-R3 | RRFKRFFKRLK (SEQ ID NO: 9) | 1581.0 | 6.11 | -2.73 |
| ATRA1-R6 | RRFRRFFRRLR (SEQ ID NO: 10) | 1665.0 | 5.87 | -3.17 |
| ATRA1-F | KRFKKFFKKFK (SEQ ID NO: 11) | 1530.9 | 7.05 | -2.76 |
| ATRA1-W2 | KRWKKFFKKWK (SEQ ID NO: 12) | 1609.0 | 8.47 | -4.20 |
| ATRA1-W3 | KRWKKWFKKWK (SEQ ID NO: 13) | 1648.1 | 8.97 | -4.92 |
| ATRA1-W4 | KRWKKWWKKWK (SEQ ID NO: 14) | 1687.1 | 9.40 | -5.64 |
| ATRA1-R3W2 | RRWKRFFKRWK (SEQ ID NO: 15) | 1693.1 | 8.09 | -4.74 |

Example 3

Endotoxin Binding

The outer leaflet of the outer membrane of Gram-negative bacteria is largely composed of LPS, a glycolipid. On the other hand, the thick peptidoglycan layer on the plasma-membrane of Gram-positive bacteria contains LTA. Both LPS and LTA can trigger massive immune responses in the form of septic shock in animals and thus act as endotoxins.

Figure 2A:
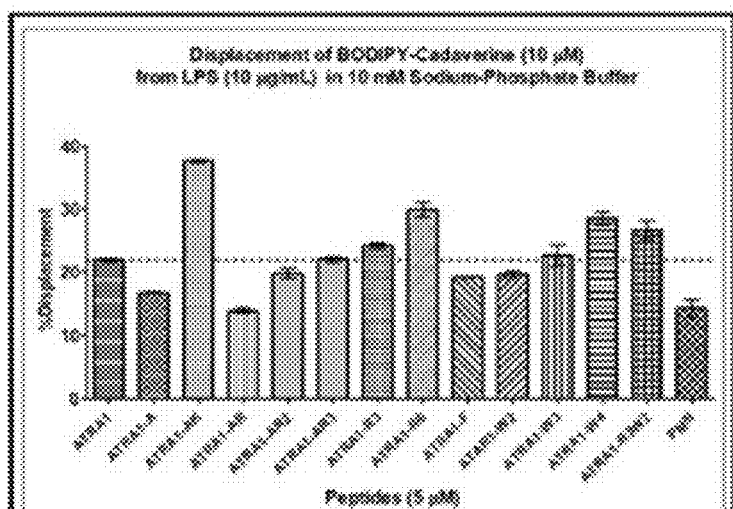
FIGS. 2A-2B are graphs showing endotoxin binding. The figures depict the competitive displacement of BC from LPS/LTA by the peptides. 5 µM of each peptide was incubated with 10 µM BC and 10 µg/mL LPS from E. coli (0111:B4) or LTA from S. aureus. Fluorescence intensity was measured at excitation=580 nm and emission=620 nm. 10 µM BC without endotoxin was used as 100% displacement while 10 µM BC with 10 µg/mL LPS/LTA without any peptide as 0% displacement and the % displacement of BC by each peptide was calculated accordingly. PMN had been used as a positive control. The horizontal dotted line coincides with the % displacement of BC by ATRA1 on the y-axis.
Figure 2B:
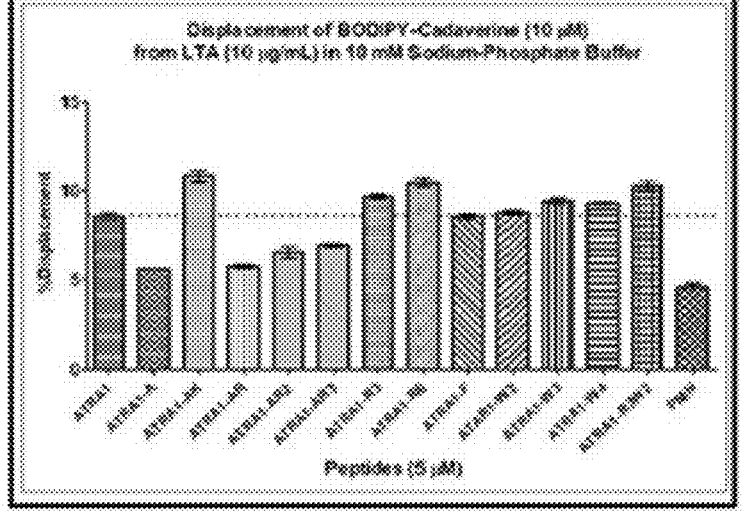

The endotoxin binding properties of the peptides were evaluated by their ability to competitively inhibit binding of BODIPY TR-Cadaverine (BC) to LPS and LTA. BC contains two functional moieties: BODIPY (boron-dipyrromethene) and cadaverine connected via a carboxamide. BODIPY is the fluorophore of BC and fluoresces in the free state in solution but loses fluorescence when bound to LPS/LTA. The competitive displacement of BC from LPS/LTA by AMPs and thus regeneration of the fluorescence has frequently been used to estimate the binding strength of AMPs with LPS/LTA. In the present studies, 5 μM of each peptide was used to displace BC from LPS/LTA. Substitution of $Phe_3$ with Ala, as in ATRA1-A, resulted in decreased LPS binding relative to ATRA1 (FIG. 2). Substitution of Arginines with Lys in ATRA1-AK resulted in ATRA1-AK, which displayed the highest LPS binding among all the peptides, whereas substitution of arginine for the Lys residue at the $9^{th}$ position afforded ATRA1-AR, which showed the lowest LPS binding of all of the peptides tested. Such observation contradicts the initial assumption that substitution of Lys with arginine would result in increased efficiency of LPS binding. However, with sequential substitutions of Lys with arginine, starting with ATRA1-AR, peptide variants show increased LPS binding with each additional arginine substitution. In terms of LPS binding: ATRA1-AR<ATRA1-AR2<ATRA1-AR3. In ATRA1-R3, the lysine residues at $9^{th}$, $5^{th}$ and $1^{st}$ positions of ATRA1 were substituted with arginine. In ATRA1-R6 all of the lysine residues were replaced with arginine. ATRA1-R3 demonstrated higher LPS binding than ATRA1, and ATRA1-R6 bound LPS more effectively than ATRA1-R3. These results supported the rational assumption that substitution of lysine with arginine can increase the LPS binding competence in ATRA1-based peptides.

The importance of the hydrophobicity of the non-polar residues were tested by substituting those residues with other non-polar residues with different degrees of hydrophobicity. When the $Phe_3$ of ATRA1 was substituted with less hydrophobic Ala, the LPS binding decreased significantly. But when $Leu_{10}$ was substituted with more hydrophobic Phe, the LPS binding also decreased relative to ATRA1 and comparable binding was not achieved until all three of the Trp-substitutions for non-polar residues had been incorporated. Such observations contradict the simple assumption that replacement of non-polar residues with more hydrophobic ones will automatically increase the LPS binding efficiency relative to the parent peptide. However, such substitutions did increase the LPS-binding efficiency when ATRA1-A, ATRA1-F, ATRA1-W2, ATRA1-W3 and ATRA1-W4 were compared, with the trend indicating that substitutions of non-polar residues by more hydrophobic ones increased the LPS binding efficiency within this series of peptides. In ATRA1-W4, all the non-polar residues were replaced with Trp, and this peptide alone demonstrated higher efficacy to bind LPS than the parent ATRA1. ATRA1-R3W2, with three arginine substitutions at the $1^{st}$, $5^{th}$ and $9^{th}$ positions and two tryptophan substitutions at the $3^{rd}$ and $10^{th}$ positions, was expected to be more effective in LPS binding than either of ATRA1-R3 and ATRA1-W2, which ended up being the case. Based on these observations, it can be generally inferred, that substituting arginine for lysine residues and tryptophan for other non-polar residues within short helical AMPs, such as ATRA1, can result in increased LPS binding efficiency. However, BC does not bind LPS effectively in high ionic-strength conditions, therefore there is no change in fluorescence associated with peptide binding. Therefore, BC displacement cannot be used to monitor LPS binding under high ionic-strength conditions. As a result, the LPS-binding effectiveness of the peptides could not be obtained in high/physiological saline conditions. The lack of ability to assess LPS-binding results in near physiological ionic conditions using BODIPY imparts limitations to this study. Despite this limitation, the study provides clues into how the cationic nature and hydrophobicity of residues impact the LPS binding properties of short AMPs such as ATRA1.

LTA from *S. aureus* was used to evaluate the LTA binding properties of the peptides. All the peptides showed low LTA binding characteristic. However, the general trend of LPS binding among the peptides was approximately maintained for LTA binding. ATRA1-AK showed the highest LTA binding. ATRA1-A showed significantly lower LTA binding than ATRA1. LTA binding increased with additional arginine substitutions, whereas, hydrophobic substitutions afforded marginal differences in LTA binding. ATRA1-

R3W2 proved to be far effective than ATRA1 in binding LTA. All of these results indicate that while certain differences exist in the parameters that determine the binding of the two endotoxins, LPS and LTA, combined substitutions by arginine and tryptophan was found to enhance binding of both the endotoxins.

Example 4

Antimicrobial Efficacies

The antimicrobial efficacies of the peptides were first tested against the model Gram-negative bacteria, E. coli ATCC 25922, in different phosphate buffers having varied ionic strengths and compositions. The phosphate buffers that were used included 10 mM sodium phosphate (calculated ionic strength~25 mM), PBS and DPBS. The PBS used sodium dihydrogen-phosphate and potassium mono-hydrogen phosphate as buffering salts, whereas, added chloride salts of sodium and potassium made the ionic strength of the buffer approximately 160 mM (calculated). The concentrations of sodium and potassium in PBS was comparable to their respective concentrations in serum. DPBS is essentially PBS supplemented with comparatively minute amounts divalent cations such as calcium (~0.9 mM) and magnesium (~0.45 mM) as chloride salts. Divalent cations are instrumental in imparting stability to the LPS outer membrane surface in Gram-negative bacteria. PBS is comparable to blood serum in terms of ionic strength, whereas the concentrations of calcium and magnesium in DPBS are almost half that found in serum. However, DPBS is often used to wash and suspend mammalian cells. Therefore, DPBS provides a buffer system which is physiologically relevant in terms of ionic strength and composition. Peptides, which are expected to be antimicrobial under physiological conditions, such as in blood, should at minimum be effective in DPBS.

Figure 3:
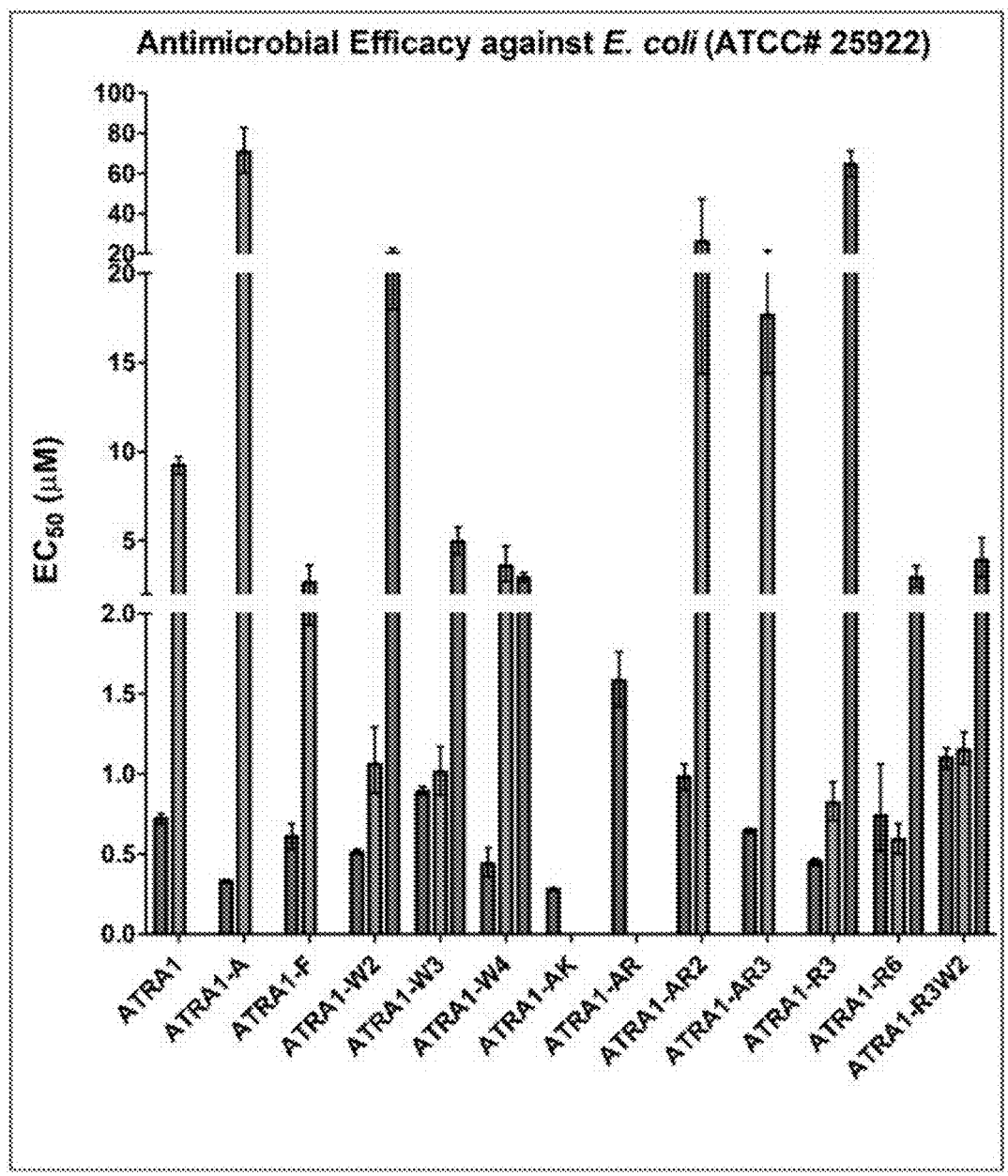
FIG. 3 is a graph showing the antimicrobial efficacy of the peptides against E. coli ATCC 25922 in three different phosphate buffers. The buffers were maintained at pH=7.4 and supplemented with 0.1% glucose prior to use. The buffers were: 10 mM sodium phosphate (blue), PBS (orange) and DPBS (green) and represented as result of triplicate. When a peptide did not display efficacy in a certain buffer condition, the results are not shown.

All the peptides demonstrated antimicrobial properties in low ionic strength conditions such as 10 mM phosphate buffer. When the ionic strength was increased, as in PBS, few of the peptides retained efficacy (FIG. 3). ATRA1-AK lost activity in PBS demonstrating the importance of the arginine residue at the $2^{nd}$ position in the ATRA-motif. Surprisingly, ATRA1-AR was completely ineffective while ATRA1-A retained some antimicrobial activity, which implies that a single lysine to arginine substitution at the $9^{th}$ position may be detrimental to ATRA peptide effectiveness. With lysine-to-arginine substitutions at the $5^{th}$ and $9^{th}$ positions, ATRA1-AR2 is more potent than ATRA1-A. Three lysine-to-arginine substitutions at the $1^{st}$, $5^{th}$ and $9^{th}$ positions improve tolerance for high ionic strength conditions, such as PBS, with ATRA1-AR3 exhibiting greater effectiveness than both ATRA1-A and ATRA1. In PBS, ATRA1-A was less powerful than ATRA1, while ATRA1-F was more effective than ATRA1, demonstrating how increasing hydrophobicity by replacing non-polar residues can contribute to salt tolerance in the ATRA peptides. The impact of increasing hydrophobicity by replacing non-polar residues with amino acids that are more hydrophobic, becomes most observable when the peptides were tested in DPBS, which contains minute amounts of divalent cations ($Ca^{++}$ and $Mg^{++}$) added to the PBS. Divalent cations are known to provide stability to the LPS outer sheaf of the OM of Gram-negative bacteria and the degree of hydrophobicity of the non-polar residues plays a critical role in modulating the antimicrobial properties exhibited by ATRA-peptides in physiologically relevant DPBS. ATRA1, ATRA1-A/AR2/AR3, which were effective in PBS, lose activity in DPBS. Similarly, ATRA1-F, in which Leu of ATRA1 was replaced with Phe, was quite effective in PBS but lost activity in DPBS. The importance of replacing of non-polar residues with Trp becomes evident as such substitutions increased ATRA-motif efficacy, with ATRA1-W4, which incorporates four Trp-substitutions, proving most effective in DPBS. The activity shown by ATRA1-R3 was significantly reduced in DPBS relative to its activity in PBS. Notably, ATRA1-R6, in which all of the lysine residues in ATRA1 had been replaced with arginine, was highly effective in DPBS. However, combining arginine and tryptophan substitutions yielded ATRA1-R3W2, which was designed as chimera combining substitutions from both ATRA1-R3 and ATRA1-W2, was more effective than either of its parent peptides against E. coli (ATCC 25922).

Figure 4:
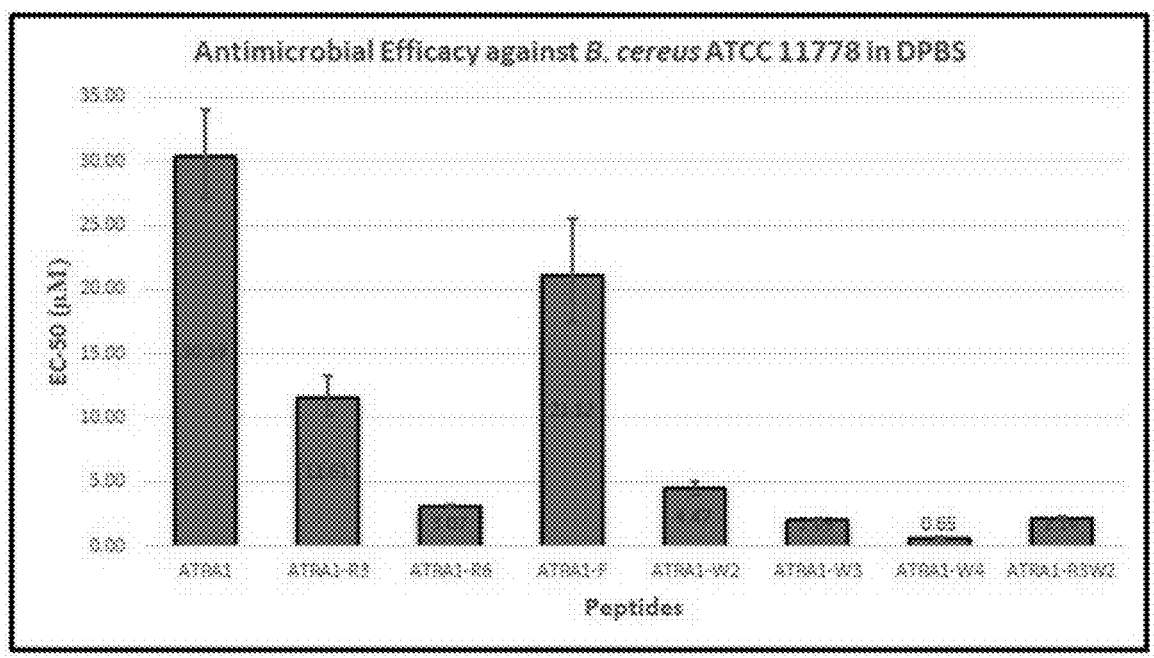
FIG. 4 is a graph showing the antimicrobial efficacy of the peptides against B. cereus ATCC 11778 in DPBS. The buffer (pH=7.4) was supplemented with 0.1% glucose prior to use.

ATRA peptide variants were then tested against B. cereus in DPBS, as model Gram-positive bacteria. The peptides were found to be more effective against B. cereus. ATRA1 and ATRA1-F, which were ineffective against E. coli, proved to be somewhat effective against B. cereus in DPBS (FIG. 4). However, ATRA1-A and its variants were not effective against B. cereus under physiologically relevant ionic conditions, while the $EC_{50}$ values of the ATRA1 variants against B. cereus were smaller in comparison to their $EC_{50}$ values against E. coli in DPBS.

Example 5

Bacterial Membrane Interactions

Some of the ATRA1-variants were further tested for their ability to disrupt outer and inner membranes to form pores or disruptions sufficiently large so as to allow enzymes to leak out of their cellular compartments (cytoplasm or periplasmic space). For this purpose, two reporter molecules were used with one being the substrate of a cytoplasmic enzyme and the other was a substrate for an enzyme residing in the periplasmic space. One of the reporters, nitrocefin was the substrate for β-lactamase, which is present in the bacterial periplasm, whereas the other molecule, ONPG, was the substrate for β-galactosidase, which resides in the cytoplasm of E. coli ML35p strain. So, detection of β-lactamase activity in supernatant, collected following incubation with peptide and subsequent removal of cells, demonstrated outer membrane disruption by formation of pores sufficiently large so as to allow the enzyme β-lactamase to escape the periplasm and enter the external aqueous environment. Similarly, β-galactosidase activity in the supernatants is evidence of inner membrane disruption and possible pore formation. When the aforesaid supernatants were tested for nitrocefin and ONPG hydrolysis, the corresponding absorbance increased with time (data not shown) indicating β-lactamase and β-galactosidase activity, respectively, and thus disruption of both the inner and outer membranes. The slopes of the increase in absorbance as a function of time provides the rate of enzyme activity. The enzyme activities in supernatants collected after incubation of bacteria with the quaternary ammonium surfactant, hexadecyltrimethylammonium bromide (HCMAB) was used as an internal reference for 100% membrane disruption. Enzyme activity for supernatants collected for cells incubated in the absence of peptide provided a reference for 0% membrane disruption. Bee venom peptide melittin was used as a positive control.

Figures 5A, 5B:
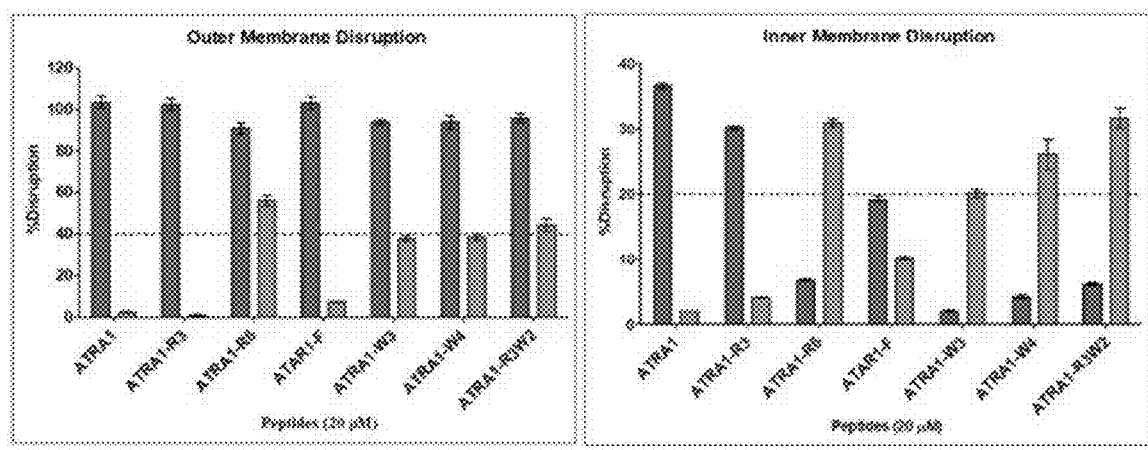
FIGS. 5A-5B are graphs showing the outer membrane (FIG. 5A) and inner membrane (FIG. 5B) disruptions of E. coli ML35p. Two different phosphate buffers were used: 10 mM sodium phosphate (blue) and DPBS (green) The activity due to HCMAB incubation was considered as 100% disruption while incubation with no-peptide was considered as 0% disruption.

The signals reporting for membrane disruption, especially that of nitrocefin hydrolysis (β-lactamase activity), reached maximum intensity very quickly for cells incubated with peptides in low ionic strength 10 mM Phosphate buffer, indicating high degrees of outer membrane disruption (over 90%) relative to HCMAB (FIG. 5). However, in physiologically relevant buffer such as DPBS, the degrees of outer membrane disruption induced by the peptides are varied. While melittin and HCMAB reached maximum signal for nitrocefin hydrolysis within approximately 15 mins, ATRA1-R6/R3W2/W3/W4 took approximately 30 mins to reach maximum absorbance. The rate of β-lactamase activity for cells treated with ATRA1-F in DPBS was intermediate, while those treated with ATRA1 exhibited the lowest activity and cells treated with ATRA1-R3 demonstrated activity that was in between those observed for ATRA1 and ATRA1-F. When the β-lactamase activities associated with the different peptides were compared (FIG. 5), substitutions of lysine residues with arginine in the ATRA1 peptides proved to lead to greater degrees of outer membrane disruption. Similarly, substitutions of non-polar residues in the ATRA1 peptides with more hydrophobic residues resulted in higher degrees of outer membrane disruption in buffer containing physiologically relevant ionic-composition. Higher outer membrane disruption was observed for ATRA1-R3W2, demonstrating enhancement of activity was achieved through simultaneous substitutions of lysine residues with arginine at the 1$^{st}$, 5$^{th}$ and 9$^{th}$ positions of ATRA1 along with replacement of the two terminal non-polar residues with tryptophan.

The trend for inner membrane disruption differs slightly from that observed for outer membrane disruption. The degree of inner membrane disruption is highest for ATRA1 in low ionic strength 10 mM phosphate buffer, and substitution of lysine residues with arginine or non-polar residues with more hydrophobic amino acids resulted in decreased activity relative to the original ATRA1 peptide (FIG. 5). However, when the low ionic buffer (10 mM phosphate) was replaced with DPBS, the arginine and hydrophobic substitutions resulted in significantly increased activities. The degree of inner membrane disruption caused by the original ATRA1 peptide fell below 10% relative to HCMAB. As seen in the other performance assays, ATRA1-R3W2 demonstrated the highest degree of inner membrane disruption.

Example 6

Bio-Informatics and Design of Peptides

The structure of NA-CATH elucidated by NMR in the presence of bacterial membrane mimetic anionic liposomes revealed an α-helical segment stretching from Phe$_3$ to Lys$_{24}$, while residues 25-34 lacked any defined stable structure. However, those structures of NA-CATH are unviable in RCSB Protein Data Bank and the I-Tasser suite utilized for predicting the secondary structures of NA-CATH and its derivatives was made to use the deposited NMR structures of crotalicidin (PDB ID: 2mwt), as alignment-template. Crotalicidin is a rattlesnake venom-gland peptide and possess high degree of primary sequence similarity with NA-CATH, which is a cobra-snake venom-gland peptide. The secondary structure predicted for NA-CATH suggested a shorter α-helical segment spanning from Phe$_3$ to Phe$_{21}$ (Table 3).

TABLE 3†

The sequence and predicted secondary structures

| Peptides | Sequences/Predicted Secondary Structure | 1 | 2 | 3 | 4 | 5 |
|---|---|---|---|---|---|---|
| Crotalicidin Sequence-Template | KRFKKFFKKVKKSVKKRLKKIFKKPMVIGVTIPF (SEQ ID NO: 52) | | | | | |
| NA-CATH Sequence | KRFKKFFKKLKNSVKKRAKKFFKKPKVIGVTFPF (SEQ ID NO: 51) | +15 | 2668 | 56 | 15 | 29 |
| Predicted Secondary Structure of NA-CATH | CCHHHHHHHHHHHHHHHHHHHCCCCCSSSSCCC | | | | | |
| NA-CATH26 Sequence | KRFKKFFKKLKNSVKKRAKKFFKKPK (SEQ ID NO: 53) | +16 | 3315 | 73 | 0 | 27 |
| Predicted Secondary Structure | CCHHHHHHHHHHHHHHHHHHHCCCCC | | | | | |
| ATRA1 Sequence | KRFKKFFKKLK (SEQ ID NO: 2) | +8 | 1497 | 64 | 0 | 36 |
| ATRA1-R3W2 Sequence | RRWKRFFKRWK (SEQ ID NO: 15) | +8 | 1693 | 64 | 0 | 36 |
| Predicted Secondary Structure | CCHHHHHHHCC | | | | | |
| ATRA1-HYD Sequence | KRFKKFFKKLK------------GGVIGVTFPF (SEQ ID NO: 38) | +9 | 1693 | 38 | 24 | 38 |

TABLE 3†-continued

The sequence and predicted secondary structures

| Peptides | Sequences/Predicted Secondary Structure | 1 | 2 | 3 | 4 | 5 |
|---|---|---|---|---|---|---|
| ATRA1-R3W2-HYD Sequence | RRWKRFFKRWK------------GGVIGVTFPF (SEQ ID NO: 50) | +9 | 2473 | 38 | 24 | 38 |
| Predicted Secondary Structure | CCHHHHHHHHC------------CCSSSSSCCC | | | | | |

†Table 3 provides the sequences and predicted secondary structures of the listed peptides along with their (calculated) molecular weights and expected charges at neutral pH. All of the peptides, except NA-CATH, were amidated at their C-terminii. The secondary structures were predicted by I-Tasser suite using the NMR structure of crotalicidin (PDB ID: 2mwt) as the template. Non-identical residues in NA-CATH and crotalicidins are shown in bold. The peptide sequences are aligned with NA-CATH and the corresponding predicted secondary structure for each residue is provided below each amino acid. C denotes Coil, H denotes Helix and S denotes Sheet as secondary structure element. Column 1: Charge; Column 2: Calculated Mol. Wt. (Da); Column 3: % Residues predicted forming α-helix; Column 4: % Residues predicted forming β-sheet; and Column 5: % Residues predicted forming random coil.

This small discrepancy may be an artifact resulting from the template sequence, crotalicidin, utilized in predicting NA-CATH secondary structure. Residues 27-34 (SEQ ID NO:17) of NA-CATH (SEQ ID NO: 51) do not contain any polar residue and is referred to as the hydrophobic C-terminal tail (-HYD). The peptides NA-CATH26 and ATRA1 were generated based on the N-terminal sequences of NA-CATH with NA-CATH26 corresponding to the first 26 residues and ATRA1, the first 11 residues. In order to confer tolerance to the ATRA1 moiety against high salt conditions, the lysines of the first cluster ($Lys_5$, $Lys_9$), along with $Lys_1$, was substituted with arginine and the two terminal non-polar residues ($Phe_3$ and $Lue_{10}$) were replaced with tryptophan, creating the new peptide variant, ATRA1-R3W2, which demonstrated higher degrees of bactericidal properties and membrane activity than parent peptide ATRA1.

To evaluate the potent contributions of the elongated hydrophobic tail of NA-CATH to the peptide's interactions with the membranes, we first generated an ATRA1 derivative in which the hydrophobic tail of NA-CATH was introduced at the C-terminus of ATRA1 by a short-GG-segment resulting in ATRA1-HYD (SEQ ID NO: 38). This peptide showed higher antimicrobial and membrane disruption activities than ATRA1. The hydrophobic tail was next introduced into the ATRA1-R3W2 in a similar fashion. Comparisons of activities of NA-CATH and NA-CATH26 demonstrated how the absence of the C-terminal elongated tail impacted the peptide activities in the context of the parent peptide. NA-CATH, ATRA1-HYD and ATRA1-R3W2-HYD (SEQ ID NO: 50) are predicted to form partial α-helical conformations. Residues $Phe_3$ to $Lys_{21}$ in NA-CATH are predicted to be helical, while the C-terminal five residues 27-31 adopt strand form, flanked by residues 22-26, and residues 32-34 forming coils. In the predicted secondary structures of ATRA1-HYD and ATRA1-R3W2-HYD, residues 3-10 are predicted to be helical, residues 11-13 random coil, residues 14-19 β-strand and the terminal 3 residues are random coil again. NA-CATH26 is predicted to form a relatively straight α-helix encompassing $Phe_3$-$Phe_{21}$, while the terminal residues $Lys_1$-$Arg_2$ and $Phe_{22}$-$Lys_{26}$ are supposed to be random coil.

The basic residues of the helical segment are predicted to interact with the anionic phosphate groups of bacterial lipids, such as LPS, while the non-polar residues on the opposite hydrophobic face are inserted into the hydrophobic interior and engage in hydrophobic interactions with the lipid acyl chains. The hydrophobic tails were also hypothesized to enhance the lipid binding, bacterial membrane disruption and consequent antimicrobial effects exerted by the peptides, akin to the methyl-octanoate segment of PMB. On the other hand, PMN which lacks the methyl-octanoate segment show very low activity.

Example 7

Endotoxin Binding

Figures 6A, 6B:
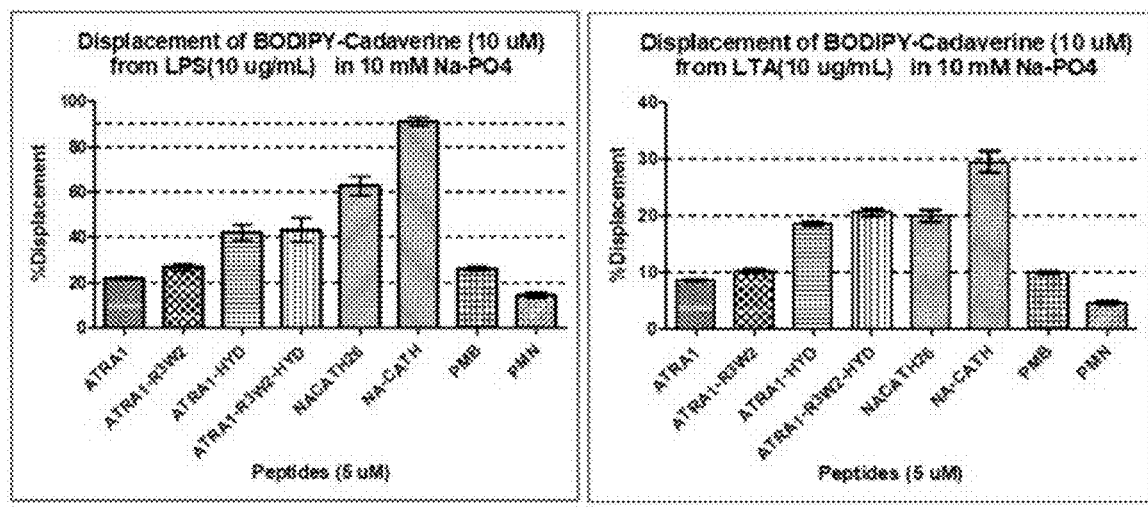
FIGS. 6A-6B are graphs showing endotoxin (LPS (FIG. 6A) and LTA (FIG. 6B)) binding. Competitive displacement of BC from LPS/LTA. In each case, 5 µM peptide was incubated with 10 µM BC and 10 µg/mL LPS from E. coli (0111:B4) or LTA from S. aureus. Fluorescence intensity was measured using excitation=580 nm and emission=620 nm. As a positive control 10 µM BC without endotoxin was used as a reference for 100% displacement while 10 µM BC with 10 µg/mL LPS/LTA without any peptide as a negative control and a reference for 0% displacement. These controls were used to calculate % BC displacement for each peptide.

LPS and LTA are abundant membrane components of Gram-negative and Gram-positive bacterial membranes and are among the first molecules that peptides encounter before destabilizing the bacterial membranes. Hence the peptides were evaluated for their ability to bind endotoxin by testing their competitive displacement of cationic BODIPY TR-Cadaverine (BC) from LPS/LTA. When bound to LPS/LTA, BODIPY-fluorescence is quenched, but it is restored when the BC is displaced by the peptides. The presence of the -HYD segment in ATRA1-HYD and ATRA1-R3W2-HYD resulted in a ~2-fold increase in affinity for LPS in both of the peptides compared to ATRA1 and ATRA1-R3W2 which lacked the hydrophobic tail (FIG. 6A). In the low ionic-strength (~25 mM) buffer used, ATRA1-R3W2 binds LPS marginally greater than ATRA1, whereas ATRA1-R3W2-HYD binds LPS with similar affinity as ATRA1-HYD. Deletion of the hydrophobic tail from the NA-CATH parent peptide resulted in a ~30% decrease in affinity for LPS in NA-CATH26. Similar differences in affinity were also observed for PMB and PMN. This observation suggests that deletion of the hydrophobic 6-9 carbon-length fatty acyl group[92] and a cationic Dab residue from PMB significantly decreased affinity for LPS in PMN.

The LTA binding properties of the peptides were evaluated using LTA from S. aureus (FIG. 6B). All of the peptides showed low LTA binding affinities. The general observed LPS-binding trend was also exhibited for LTA-binding. Both ATRA1-HYD and ATRA-R3W2-HYD demonstrated ~2-fold higher degrees of LTA binding than their parent peptides, ATRA-1 and ATRA1-R3W2 respectively. However, both of the peptides with arginine and tryptophan substitutions showed marginally higher LTA binding than their corresponding ATRA1 based counterparts.

NA-CATH26, which lacks the hydrophobic tail, bound LTA to a significantly lower degree than NA-CATH, which was similar the case for PMN and PMB. These observations suggest that the hydrophobic tail in both NA-CATH and the 21-residue ATRA-HYD peptides contributes to endotoxin binding.

Example 8

Antimicrobial Efficacies

Figure 7:
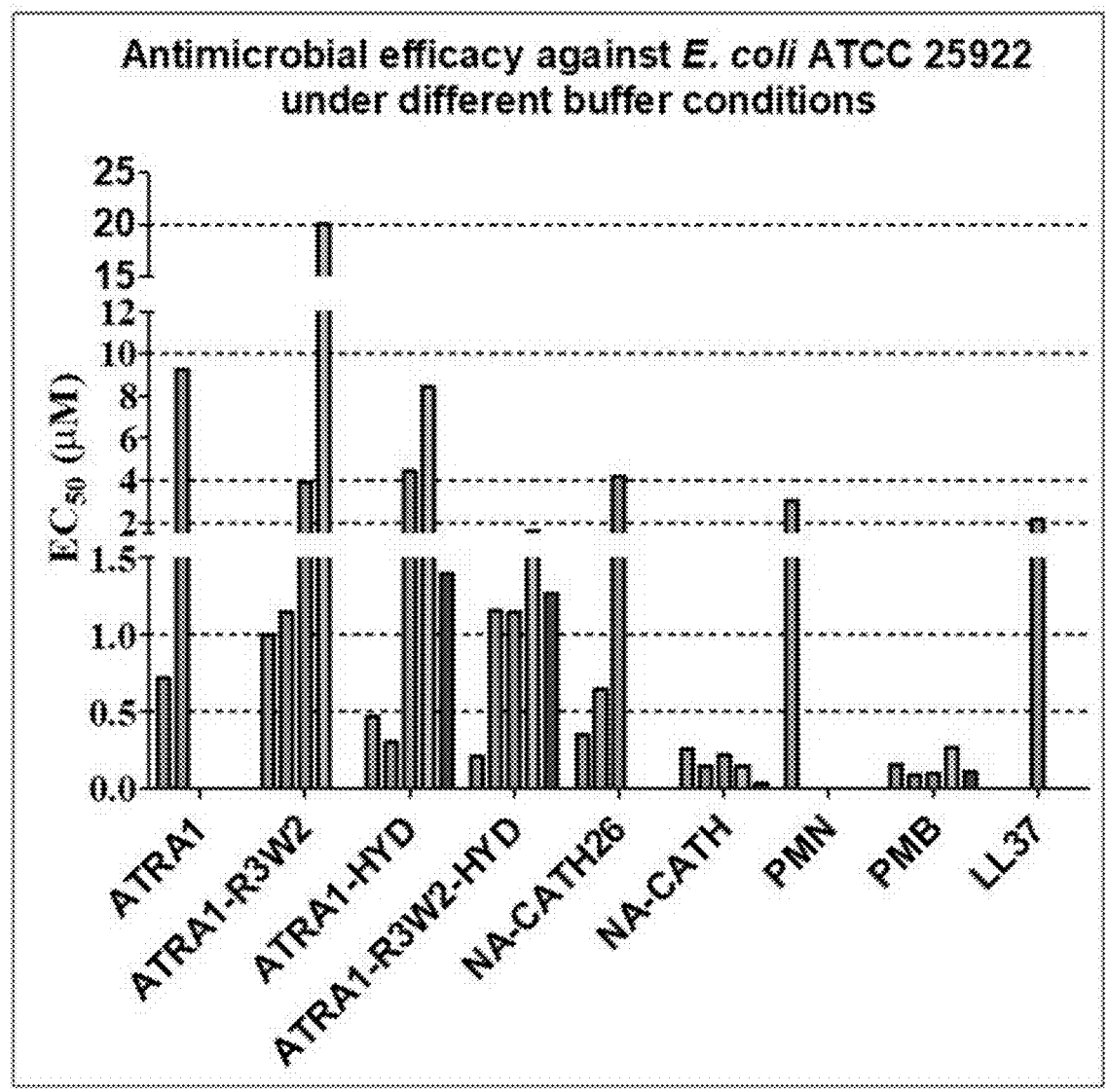
FIG. 7 is graph showing anti-microbial effectiveness against type strain E. coli (ATCC 25922) under different conditions of buffer. Various kinds of phosphate buffers were utilized: 10 mM Sodium phosphate (blue), PBS (orange), DPBS (green) and DPBS+4% bovine serum albumin (pink). The peptides were also tested against the E. coli in bovine serum (red). The results are represented as mean of triplicate. When a peptide did not display efficacy in a certain buffer condition, the results are not shown. LL37 was not tested in 10 mM sodium phosphate buffer or in PBS, and so the results are not shown for those buffers.

The antimicrobial efficacies of the peptides were first tested against model Gram-negative bacteria, E. coli ATCC 25922, in different phosphate buffers with varied ionic strengths and compositions (FIG. 7). The phosphate buffers that were used includes 10 mM sodium phosphate (calculated ionic strength~25 mM), PBS (~160 mM) and DPBS, which is PBS containing minute amounts of divalent cations, ~0.9 mM calcium chloride and ~0.45 mM magnesium chloride. Divalent cations, such as $Ca^{++}$ and $Mg^{++}$, are instrumental in imparting stability to the LPS membrane in Gram-negative bacteria. PBS is comparable to blood serum in terms of ionic strength, whereas the concentrations of calcium and magnesium in DPBS are almost half that of serum. However, DPBS is often used to wash and suspend mammalian cells. Therefore, DPBS represents a buffer system which is physiologically relevant in terms of ionic strength and composition. The peptide effectiveness was then tested in serum against multiple pathogenic bacteria, both antibiotic resistant and susceptible strains, to evaluate their potential effectiveness in vivo against bacterial infections. Peptides, which are expected to be antimicrobial in physiological conditions, should be effective in serum. When peptides performed differently in serum than they did in DPBS, we tested them in DPBS supplemented with 4% (w/v) bovine serum albumin, to assess whether the differences in performance are due to the presence of high amounts of albumin in serum.

All the peptides demonstrated significant efficacies against E. coli (ATCC 25922) under low ionic conditions (FIG. 7). However, under the physiologically relevant ionic conditions, PMN lost activity and the efficacies of NA-CATH26 and ATRA1-R3W2-HYD decreased approximately 2-fold and 5-fold respectively. With further introduction of minute amounts of divalent cations, in DPBS, ATRA1 lost antimicrobial property, whereas the efficacies of ATRA1-R3W2, ATRA1-HYD and NA-CATH26 decreased by approximately 3, 10 and 14 folds respectively relative to their respective effectiveness in 10 mM Na—$PO_4$. When tested against E. coli (ATCC 25922) under near physiological ex-vivo condition such as serum, ATRA1-R3W2 demonstrated no antimicrobial property, whereas, the ATRA1 and NA-CATH derived peptides, containing the peptide hydrophobic tail, and PMB, containing its acyl-hydrocarbon segment, retained significant antimicrobial activities. To investigate what factors may have contributed towards the failure of ATRA1-R3W2 in serum while it was active in physiologically relevant ionic conditions, we tested the peptides in a new buffer condition: DPBS supplemented with 4% (w/v) bovine serum-albumin (BSA). Serum contains serum-albumin other than inorganic salts of $Na^+$, $K^+$, $Mg^{++}$ and $Ca^{++}$. While inorganic salts maintain the ionic strength, the serum-albumin, which is a major component (~4 g/dL in humans) of serum, contributes towards the viscosity of the blood, maintenance of colloidal osmotic pressure, binding of various compounds and contributing significantly in plasma antioxidant activity and is often used as a blocker to inhibit non-specific binding in immunochemistry. Serum-albumin possesses a strong net negative-charge and property to bind hydrophobic molecules. It may competitively sequester short amphipathic cationic peptides and thus limit their antimicrobial activities. In the presence of albumin in DPBS, the $EC_{50}$ values of ATRA1-R3W2, PMB and ATRA1-HYD increased approximately by 5, 3 and 2-folds respectively relative to their $EC_{50}$ values in DPBS against E. coli (ATCC 25922). On the contrary, ATRA1-R3W2-HYD and NA-CATH did not demonstrate significant changes in $EC_{50}$ values in presence of serum-albumin in DPBS. Thus, the presence of serum-albumin partially explains the loss of activity by short 11-residue ATRA1-R3W2 in serum. These results signify the importance of presence of hydrophobic segments in peptides for their antimicrobial activities in near phycological conditions. The new non-natural variant, ATRA1-R3W2-HYD, demonstrated significant antimicrobial effectiveness against type strain, E. coli (ATCC 25922), and was further tested for therapeutic relevance against different microbial pathogens.

Figure 8:
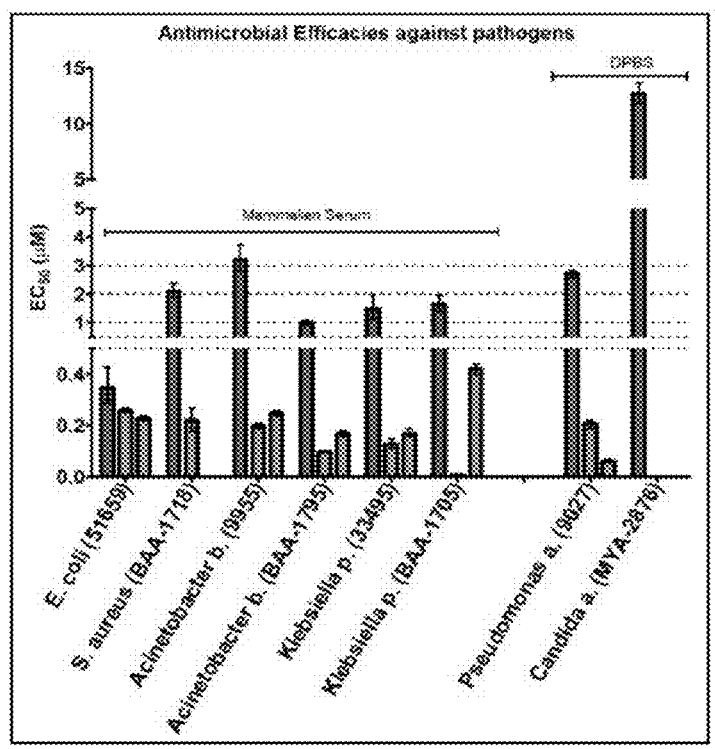
FIG. 8 is a graph showing antimicrobial efficacies of ATRA1-R3W2-HYD (blue), NA-CATH (dark orange) and PMB (green) against selected members of ESKAPE (*Enterococcus faecium, Staphylococcus aureus, Klebsiella pneumoniae, Acinetobacter baumannii, Pseudomonas aeruginosa*, and *Enterobacter*) pathogens. Both susceptible and drug-resistant strains were used. All the bacteria, except *Pseudomonas aeruginosa*, were tested under mammalian serum. *P. aeruginosa* results were obtained from testing in DPBS. The results are presented as mean of tests in triplicate with error-bars depicting the 95% confidence interval of the mean.

ATRA1-R3W2-HYD, NA-CATH and PMB were evaluated for their effectiveness in mammalian serum conditions against pathogenic bacteria of both normal and drug-resistant strains. The main objective of this study was to evaluate the therapeutic potency of the three peptides under near physiological ex-vivo conditions. PMB has been adapted in present times as a last resort drug against antibiotic resistant infections despite its significant in-vivo cytotoxicity and can serve as a reference for evaluating new peptide drug-candidates. The peptides were tested against members of the ESKAPE pathogens, which have earned considerable notoriety for causing small molecule antibiotic-resistant infections and consequent deaths. It is to be noted that the drug-resistant strains were grown in the presence of some of the respective drugs against which they are resistant and tested the peptides on them. The results are summarized in FIG. 8. As such, NA-CATH and the new derived variant, ATRA1-R3W2-HYD did not demonstrate antimicrobial effectiveness against Pseudomonas aeruginosa in serum but exhibited good bactericidal properties under physiologically relevant ionic conditions (DPBS). Only PMB was effective against P. aeruginosa in mammalian serum (results not shown). However, ATRA1-R3W2-HYD and NA-CATH were highly effective, though in lower degree than PMB, when tested against all the other pathogens. Some of the notable pathogens against which ATRA1-R3W2-HYD and NA-CATH were effective in mammalian serum include multi-drug resistant (MDR) Acinetobacter baumannii (ATCC BAA-1795) and Klebsiella pneumoniae (ATCC BAA-1705). In every instance, ATRA1-R3W2-HYD was effective in a lesser degree than NA-CATH, which may be in part due to decreased net cationic-charge and sequence-length. Nevertheless, these results signify the clinical relevance of rationally designed shorter variant ATRA1-R3W2-HYD, which contains the hydrophobic tail of NA-CATH, in combating against MDR bacteria.

Example 9

Bacterial Membrane Disruptions

Peptides were further evaluated for their ability to disrupt bacterial outer and inner membranes and their ability to create pores large enough to allow enzymes to leak out of the cells. In order to distinguish between inner and outer membrane disruption, we assessed for the release of two enzymes, β-lactamase and β-galactosidase, which are located in different compartments in E. coli ML35p. This strain produces β-galactosidase in the cytoplasm, but the absence of permease prevents lactose transportation across membranes and its fermentation in the cytoplasm. Transformation of E. coli ML35 with pBR322 gives rise to the ampicillin-resistant E. coli ML35p strain. The pBR322 plasmid includes a gene for β-lactamase and E. coli ML35p produced the ampicillin degrading enzyme β-lactamase, which is localized to the bacterial periplasmic space. Thus, β-lactamase and β-galactosidase leakage following incubation with peptides provide indicators of outer-membrane and inner-membrane disruptions, respectively, by formation of openings, pores, in the membranes large enough to allow passage of these enzymes. In this assay, the bacteria, E. coli ML35p, were first incubated in buffer that contained peptides and the cells were then separated by centrifugation and the supernatants were tested for β-lactamase and β-galactosidase activities separately utilizing their respective substrates Nitrocefin, (chromogenic cephalosporin) and ONPG (lactose analogue). If the peptides disrupted either membrane, absorbances resulting from enzyme activities on these substrates would increase with time and the rate of increase would provide a measure of the rate of enzyme activity. The enzyme activities in the supernatant collected following incubation of the bacteria in the presence of a quaternary ammonium surfactant, Hexadecyltrimethylammonium bromide (HCMAB), provided an internal reference for 100% membrane disruptions. The bee venom peptide melittin also provided a positive control.

Figure 9:
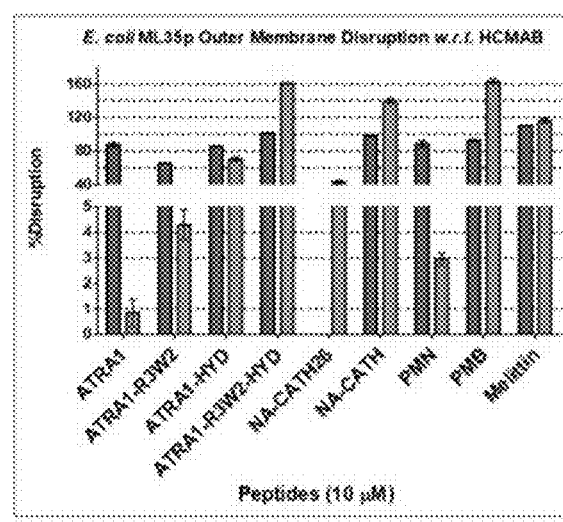
FIG. 9 is a graph showing the *E. coli* outer membrane disruption in phosphate buffers with varying ionic composition. Low ionic strength 10 mM sodium phosphate (blue) and (physiologically relevant ionic conditions) DPBS (green). The activity due to HCMAB incubation was considered as 100% disruption while incubation with no-peptide was considered as 0% disruption and the results are displayed as mean of duplicate studies.

The signals for Nitrocefin hydrolysis reached their maximum very quickly (within ~15 min) for peptides incubated in low ionic-strength 10 mM phosphate buffer, and they exhibited similar absorbance slopes over time (data not shown), indicating high degrees of outer membrane disruptions. When the degrees of outer membrane disruption were compared to that of HCMAB, ATRA1 displayed a higher degree of disruption than ATRA1-R3W2, but a degree of disruption similar to that observed for ATRA1-HYD (FIG. 9). The other peptides ATRA1-R3W2-HYD, NA-CATH, PMN, PMB and melittin demonstrated similar high degrees of membrane disruption (90-110% w.r.t HCMAB). However, the rates of nitrocefin hydrolysis for peptides incubated under physiologically relevant ionic strength conditions such as DPBS varied widely suggesting diverse degrees of outer membrane disruption under these conditions (data not shown). Membrane disruption by ATRA1 decreased to less than 1% in DPBS HCAMAB), while that of ATRA-R3W2 decreased to approximately 4%. Peptide variants that included the hydrophobic tail exhibited higher degrees of outer membrane disruption, with ATRA1-R3W2-HYD demonstrating 160% membrane-disruption w.r.t. the quaternary-ammonium surfactant HCMAB. PMB demonstrated outer membrane disruption similar to that of ATRA1-R3W2-HYD, while NA-CATH and melittin afforded slightly lower degrees of membrane-disruption. Under physiologically relevant ionic strength conditions, absence of the hydrophobic segment resulted in reduced outer membrane disruption, with both PMN and NA-CATH26 exhibiting significantly lower degrees of β-lactamase leakage than observed for PMB and NA-CATH respectively. (However, NA-CATH26 was not tested for outer membrane disruption in low ionic-strength conditions due to the limited amount of peptide that was available).

Example 10

Cytotoxicity

Figure 10A:
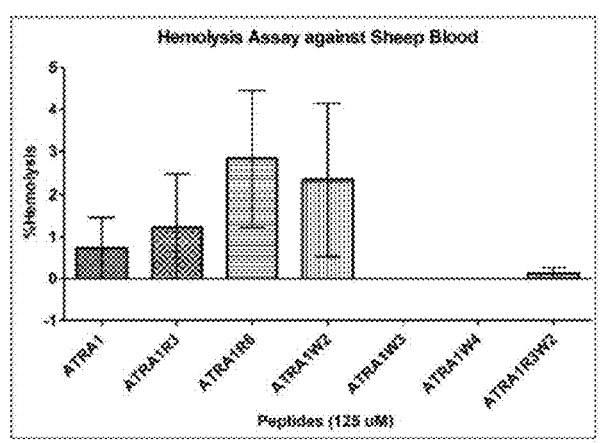
FIGS. 10A-10B are graphs showing the hemolysis activity of NA-CATH derived peptide variants and PMB against sheep erythrocytes. Peptides were incubated at 125 μM against 10% suspension of sheep blood cells in DPBS for 1 hour at 37° C. where, DPBS alone served as negative control and 1% TritonX-100 served as 100% lysis. After incubation, the cells and the debris were pelleted by centrifugation (1000 r.p.m, 5 min) and the supernatant was transferred to a microplate and absorbance read at 540 nm was conducted. Each peptide was tested in triplicate.
Figure 10B:
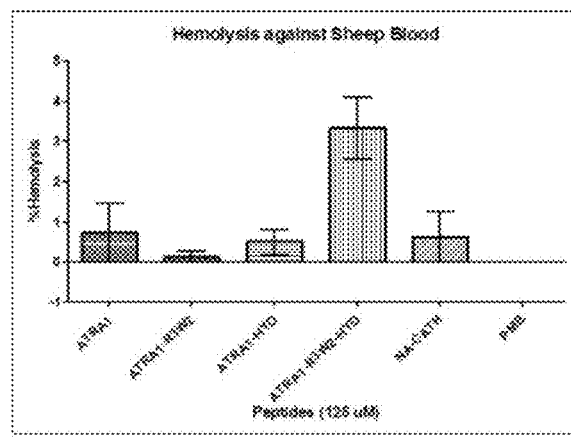

The hemolytic activities of the peptides were tested as an initial measure of potential cytotoxicity. The hemolytic properties of the peptides were tested using sheep erythrocytes and a high peptide concentration (125 μM). Even at this high concentration, the peptides demonstrated very low (<5% w.r.t. 1% TritonX-100) or negligible degrees of hemolysis (FIG. 10).

Example 11

Toxicity Against Human Lung Epithelial Cells

Figures 11A, 11B:
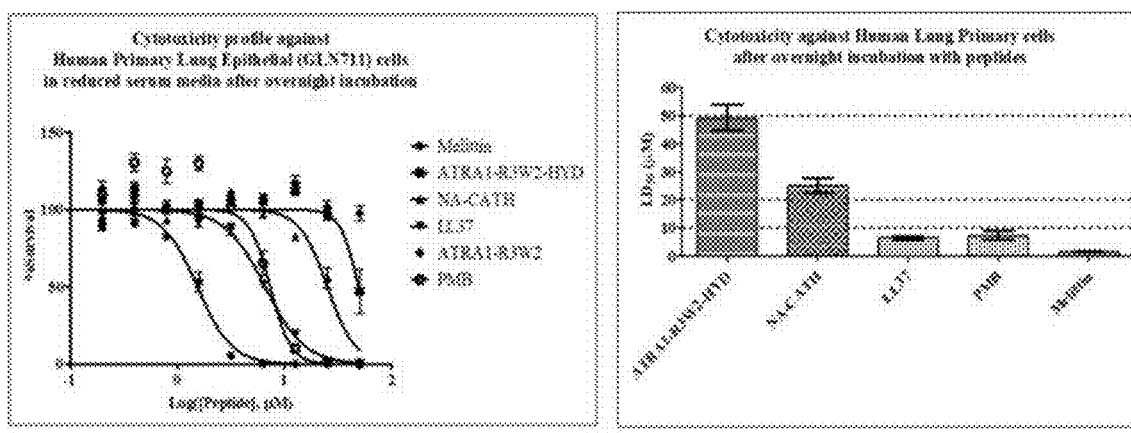
FIGS. 11A-11B are graphs showing cytotoxicity against primary lung epithelium cells in serum-free condition. Cells were seeded in complete growth medium (Minimal essential medium supplemented with 10% fetal bovine serum) at near-confluence into a 96-well plate and allowed to settle for 24-hours. Media was then replaced to OptiMEM I reduced serum medium containing peptide or vehicle alone (DBPS) and cells were incubated overnight (16 hours). A resazurin based dye (Alamar blue) was added directly to media and conversion of resazurin to resorufin was evaluated following two hours. % Survival represents the proportion of viable cells in peptide treated cells relative to cells treated with vehicle alone. Linear regression was performed to identify the concentration to achieve 50% lethality ($LD_{50}$) for each toxic peptide. Each peptide was tested in triplicate.
Figure 12:
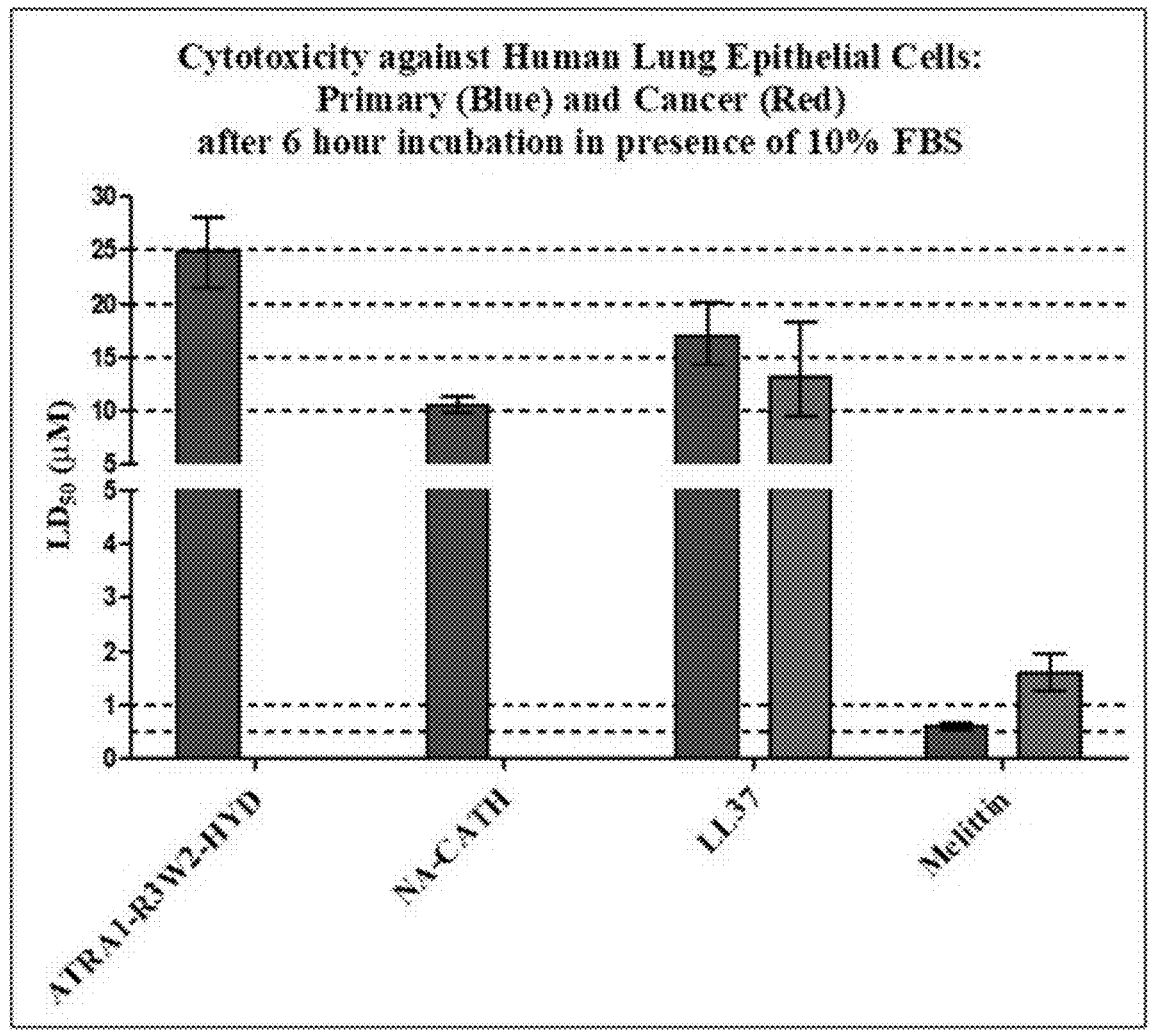
FIG. 12 is a graph showing comparison of toxicities against Lung Primary Epithelial cells and Lung Cancerous Epithelial Cells, derived from H358 cell-line. Non-linear regression analysis of six-hour cytotoxicity data was performed to identify the concentration to achieve 50% lethality ($LD_{50}$) for each toxic peptide. Each peptide was tested in triplicate.

The NA-CATH derived peptides and PMB were tested against human lung epithelial cells to evaluate the therapeutic potential of the peptides. Bee venom peptide, melittin, and human cathelicidin, LL37, were used as reference peptides for comparison. Melittin is known to be cytotoxic against both normal and cancer cells whereas, LL37 possess tissue specific activity on cancer/tumor cells and proliferates growth in certain human lung cancer cell lines. The peptides were incubated for a prolonged period of ~16 hours (overnight) under reduced serum conditions, as presence of serum may hinder killing. Results are shown in FIG. 11. The degree of resazurin reduction by the cells, after incubation with the peptides were compared with the degree of resazurin reduction by (control) cells, which were not incubated with any peptide (100% survival) and were regarded as the % survival after incubation with the respective peptide. Incubation with ATRA1-R3W2-HYD decreased the degree of resazurin reduction in the primary cells by 50% w.r.t. the control cells at a concentration ~50 μM, while NA-CATH did the same at ~25 μM. All the other peptides, including LL37, demonstrated higher degrees of cytotoxicity. Melittin killed the cells at the highest degree. Over 10 μM concentration LL37 revealed significant cytotoxicity. Even though unexpected, LL37 had demonstrated significant cytotoxicity against leucocytes and T-cells at the concentrations of 13-25 μM. Significant cytotoxicity of LL37 was observed against cultured lung primary epithelial cells in the similar concentration range and almost 100% killing at over ~25 μM concentrations. PMB exhibit significant in vivo and in vitro toxicities and had found initial application in topical medications only. However, emergence of antibiotic resistant bacterial infections has made PMB as one of the drugs of last resort despite its toxicity. We observed significant toxicity of PMB over ~6 μM concentration against the lung primary cells in vitro. The $LD_{50}$ of PMB, LL37 and Melittin were all below 10 μM. On the contrary, toxicity of NA-CATH was significant over ~25 μM concentration and of ATRA-R3W2-HYD at ~50 μM. All these results suggest NA-CATH and the derived non-natural variant, ATRA1-R3W2-HYD, may be clinically more favorable therapeutics with less toxicity.

Example 12

Toxicity Against Primary and Cancer-Derived Human Lung Epithelial Cells

The peptides were tested against both primary and cancer-derived human lung epithelial cells. H-358 cells were used as model lung epithelial cancer cells. The cells were exposed to the peptides for a brief period of time (~6 hours) in presence of 10% fetal bovine serum, which is conducive to proliferation of both the cell types. Under similar conditions of buffer and exposure time, the NA-CATH derived peptides demonstrated no cytotoxicity against the primary cells, whereas, LL37 exhibited toxicity over ~10 μM concentration and melittin over ~1 μM (FIG. 52). On the other hand, all the peptides, including LL37 demonstrated various degrees of killing of the cancer cells. LL37 exhibited toxicity against the H-358 cancer cell line with a $LD_{50}$~17 μM. NA-CATH exhibited higher toxicity ($LD_{50}$~10.5 μM) against the cancer cells in comparison to ATRA1-R3W2-HYD ($LD_{50}$~24.5 μM). All these results suggest significant selective toxicity of NA-CATH and its derivative ATRA1-R3W2-HYD against human lung cancer epithelial cells even in a brief exposure time under physiologically relevant growth conditions of the cells.

Example 13

Perturbation of Cell Membranes

When peptides partition from the bulk aqueous environment to the cellular membranes, they may cause small defects in the membrane organization, a signature of adsorption of the peptides into the membranes. Such small defects are called membrane perturbations and can be evaluated by utilizing molecular probes. One such molecular probe is NPN, which is a hydrophobic molecule and is usually repelled to enter the hydrophobic interiors of the membrane by the polar headgroups of membrane-lipids. However, when small defects and gaps are caused during the adsorption of the peptides into the membranes, NPN can enter through those defects and in the hydrophobic environment of the membrane interior the molecule fluoresces, which can be measured for quantification of the extent of membrane-perturbation and peptide adsorption in the cellular membrane.

Figure 13:
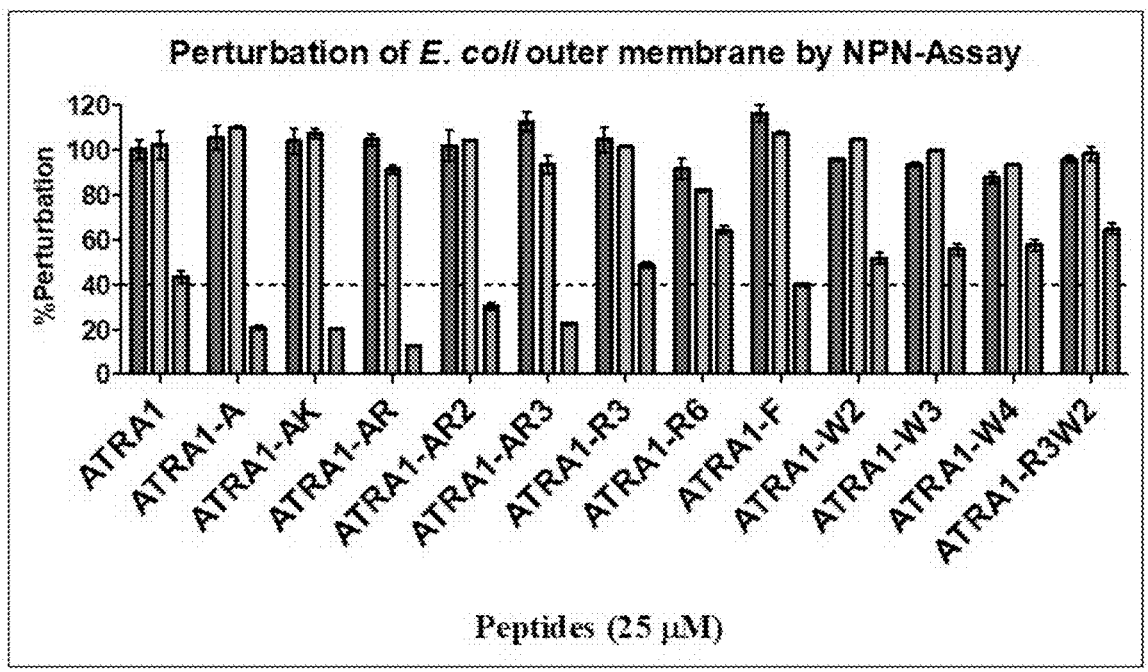
FIG. 13 is a graph showing perturbation of *E. Coli* out membrane by NPN-Assay.

The effects of ionic strengths and compositions on the abilities of the peptides to perturb membrane integrity (FIG. 13) were studied by monitoring NPN translocation into E. coli membranes (using fluorescence) in presence and absence of peptide under varied buffer conditions. The extent of membrane perturbation caused by a peptide was normalized with respect to 25 μM PMB, which was assumed to afford 100% membrane perturbation. At low ionic strength, 10 mM phosphate buffer, all of the peptides showed substantial perturbation of the outer membrane of E. coli. The extent of membrane perturbation inflicted by a few peptides, such as ATRA1-AR, ATRA1-R6 and ATRA1-F, decreased slightly in high ionic strength PBS, but in general remained similar to their performance in 10 mM phosphate buffer. Dramatic changes in membrane perturbation were observed when the peptides were evaluated in DPBS. The presence of the divalent cations in high ionic conditions blunted membrane perturbation substantially for all the peptides tested. The ATRA1-A variants were particularly sensitive to the presence of divalent ions (perturbation below 40% with respect to PMB). ATRA1-R3/R6/W2/W3/W4/R3W2 exhibited higher OM perturbation than ATRA1 in DPBS. ATRA1-R6 showed greater degrees of perturbation than ATRA1-R3, and ATRA1-W2/W3/W4 show higher perturbation than ATRA1-F. As was observed for LPS binding, ATRA1-A proved less effective at perturbing the outer membrane than ATRA-1. These observations demonstrate how substitution of lysine residue residues with arginine along with replacing nonpolar residues with more hydrophobic amino acids can impact the ability of ATRA peptides to perturb bacterial outer membrane and adsorption of the peptides in the membranes under physiologically relevant ionic conditions.

Figure 14:
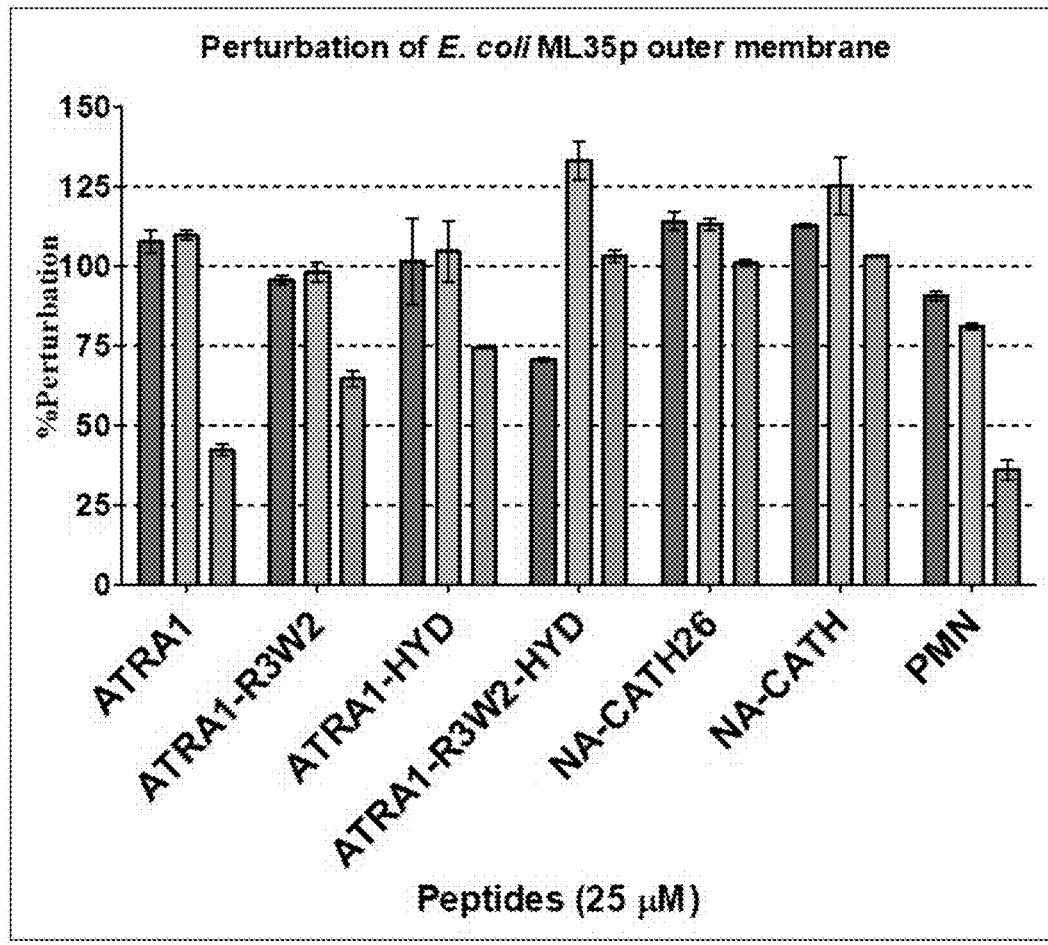
FIG. 14 is a graph showing perturbation of *E. Coli* ML35p out membrane.

The effect of the C-terminal hydrophobic tail in the peptides on the perturbation of membranes were evaluated and compared with the hydrophobic acyl segment of Polymyxin (FIG. 14). The extent of membrane perturbation by the peptide was normalized with respect to 25 μM PMB, which was used as a scale causing 100% membrane perturbation. In low ionic-strength buffer (10 mM Na—PO4), all the peptides demonstrated significant membrane perturbations. PMN displayed a little less membrane perturbation while NA-CATH26 and NA-CATH demonstrated higher degree of membrane perturbations than PMB. Interestingly, membrane perturbation by ATRA-R3W2-HYD was significantly less (75% with respect to PMB) at low ionic conditions but becomes significantly high and comparable to PMB at physiological ionic-strength conditions. In PBS, Both NA-CATH26 and NA-CATH also perturbed outer membrane greater than PMB, while ATRA1, ATRA1-R3W2, ATRA1-R3W2 perturbed comparable to PMB and the degree of membrane perturbation by PMN got decreased to ~75%. However, striking differences among the degrees of membrane perturbation by the peptides were observed on supplementing minute amounts of divalent cations to physiological ionic-strength conditions. In DPBS, degree of membrane perturbation by ATRA1 decreased significantly (less than 50%), while that of ATRA-R3W2 was ~65%, demonstrating that the combination of arginine and tryptophan-substitutions introduced elevated degree of membrane perturbation in 11-residue ATRA-motif. The degrees of membrane perturbation were further increased by addition of the hydrophobic tail to the ATRA1-variants and ATRA1-HYD and ATRA-R3W2-HYD demonstrated ~75% and ~100% membrane perturbation w.r.t PMB respectively. However, NA-CATH26 and NA-CATH displayed similar degrees of membrane perturbation, suggesting that deletion of the hydrophobic tail from NA-CATH did not result in a decrease in membrane-perturbation activity. On the other hand, PMN showed significantly lower membrane perturbation in DPBS (~35% with respect to PMB). It is worth noting that even though ATRA1 is a linear peptide and PMN is cyclic, they are both short peptides: ATRA1 is 11-residue long while PMN is 9-residue. The results suggest that apart from the presence of hydrophobic tail, the peptide length may also influence the degree of membrane perturbation and adsorption in the membrane.

We claim:

1. A peptide comprising the amino acid sequence set forth in SEQ ID NO: 7, 8, 9, 11, 12, 13, 14, or 15.

2. The peptide of claim 1 further comprising a linked segment having a linked segment amino acid sequence of SEQ ID NO: 17 or 20.

3. A polynucleotide encoding the peptide of claim 1.

4. A composition comprising the peptide of claim 1 or a polynucleotide encoding the peptide.

5. An article of manufacture or kit comprising the peptide of claim 1.

6. A conjugate comprising the peptide of claim 1 conjugated to an agent, wherein the peptide is connected to the agent directly or through a linker segment, the agent being connected to the peptide or the linker segment through a stable or cleavable bond, wherein the conjugate carries and facilitates the delivery of the conjugated agent to a microbe or a cancer cell or a tumor cell.

* * * * *